United States Patent
Serina et al.

(10) Patent No.: US 10,625,047 B2
(45) Date of Patent: *Apr. 21, 2020

(54) ANCHOR DEPLOYMENT DEVICES AND RELATED METHODS

(71) Applicant: Ancora Heart, Inc., Santa Clara, CA (US)

(72) Inventors: Eugene Serina, Fremont, CA (US); Stephen C. Meier, San Francisco, CA (US); Shih-Hsiung Albert Yuan, Sunnyvale, CA (US); Mariel Fabro, San Francisco, CA (US)

(73) Assignee: Ancora Heart, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/474,877

(22) Filed: Mar. 30, 2017

(65) Prior Publication Data

US 2018/0043132 A1    Feb. 15, 2018

Related U.S. Application Data

(63) Continuation of application No. 14/052,593, filed on Oct. 11, 2013, now Pat. No. 9,616,197, which is a
(Continued)

(51) Int. Cl.
*A61B 17/04*    (2006.01)
*A61M 25/00*    (2006.01)
(Continued)

(52) U.S. Cl.
CPC ..... *A61M 25/0043* (2013.01); *A61B 1/00078* (2013.01); *A61B 6/12* (2013.01);
(Continued)

(58) Field of Classification Search
CPC ............ A61B 17/0057; A61B 17/0401; A61B 17/07207; A61B 17/064; A61B 2017/0409; A61B 2017/00668
See application file for complete search history.

(56) References Cited

U.S. PATENT DOCUMENTS 3,656,185 A    4/1972  Carpentier
3,773,034 A    11/1973 Burns et al.
(Continued)

FOREIGN PATENT DOCUMENTS

EP    0 637 431 A1    2/1995
EP    0 669 101 A1    8/1995
(Continued)

OTHER PUBLICATIONS

De Simone, R. et al. (Apr. 1, 1994). "Adjustable Annuloplasty for Tricuspid Insufficiency with External Control," *Reader's Comments and Reply, Am. J. Cardiol.* 73(9):721-722.
(Continued)

*Primary Examiner* — Shaun L David
*Assistant Examiner* — Christina C Lauer
(74) *Attorney, Agent, or Firm* — Cooley LLP

(57) ABSTRACT

Described here are devices, methods, and kits for the deployment of tissue anchors. In some variations, the devices may comprise a shaft defining a lumen for housing at least one anchor therein and a mechanism for deploying the anchor distally from the lumen. In certain variations, the devices may comprise one or more stop elements. For example, a device may comprise a stop element that limits the advancement of the device through an opening in a wall portion or at the distal end of another device.

13 Claims, 40 Drawing Sheets

Related U.S. Application Data continuation of application No. 12/657,422, filed on Jan. 19, 2010, now abandoned.

(60) Provisional application No. 61/178,938, filed on May 15, 2009, provisional application No. 61/178,910, filed on May 15, 2009, provisional application No. 61/160,670, filed on Mar. 16, 2009, provisional application No. 61/160,230, filed on Mar. 13, 2009, provisional application No. 61/145,964, filed on Jan. 20, 2009.

(51) Int. Cl.

| | | |
|---|---|---|
| *A61B 1/00* | (2006.01) | |
| *A61B 6/12* | (2006.01) | |
| *A61B 8/12* | (2006.01) | |
| *A61B 17/00* | (2006.01) | |
| *A61B 6/00* | (2006.01) | |
| *A61B 1/313* | (2006.01) | |
| *A61B 17/32* | (2006.01) | |
| *A61B 17/72* | (2006.01) | |
| *A61M 25/04* | (2006.01) | |

(52) U.S. Cl.
CPC .............. *A61B 6/481* (2013.01); *A61B 6/485* (2013.01); *A61B 8/12* (2013.01); *A61B 17/0057* (2013.01); *A61B 17/00234* (2013.01); *A61M 25/0041* (2013.01); *A61B 1/3137* (2013.01); *A61B 17/320016* (2013.01); *A61B 17/7208* (2013.01); *A61B 2017/00243* (2013.01); *A61M 25/04* (2013.01); *A61M 2210/127* (2013.01)

(56) References Cited

U.S. PATENT DOCUMENTS

| | | |
|---|---|---|
| 3,961,419 A | 6/1976 | Schwartz |
| 3,976,079 A | 8/1976 | Samuels et al. |
| 4,014,492 A | 3/1977 | Rothfuss |
| 4,034,473 A | 7/1977 | May |
| 4,042,979 A | 8/1977 | Angell |
| 4,043,504 A | 8/1977 | Hueil et al. |
| 4,044,765 A | 8/1977 | Kline |
| 4,053,979 A | 10/1977 | Tuthill et al. |
| 4,055,861 A | 11/1977 | Carpentier et al. |
| 4,069,825 A | 1/1978 | Akiyama |
| 4,273,127 A | 6/1981 | Auth et al. |
| 4,290,151 A | 9/1981 | Massana |
| 4,384,406 A | 5/1983 | Tischlinger |
| 4,445,509 A | 5/1984 | Auth |
| 4,445,892 A | 5/1984 | Hussein et al. |
| 4,489,446 A | 12/1984 | Reed |
| 4,494,542 A | 1/1985 | Lee |
| 4,576,772 A | 3/1986 | Carpenter |
| 4,619,247 A | 10/1986 | Inoue et al. |
| 4,681,093 A | 7/1987 | Ono et al. |
| 4,700,250 A | 10/1987 | Kuriyama |
| 4,726,371 A | 2/1988 | Gibbens |
| 4,758,221 A | 7/1988 | Jureidini |
| 4,784,133 A | 11/1988 | Mackin |
| 4,817,613 A | 4/1989 | Jaraczewski et al. |
| 4,845,851 A | 7/1989 | Warthen |
| 4,848,341 A | 7/1989 | Ahmad |
| 4,850,354 A | 7/1989 | McGurk-Burleson et al. |
| 4,898,577 A | 2/1990 | Badger et al. |
| 4,898,591 A | 2/1990 | Jang et al. |
| 4,906,230 A | 3/1990 | Maloney et al. |
| 4,961,738 A | 10/1990 | Mackin |
| 4,969,893 A | 11/1990 | Swor |
| 4,976,710 A | 12/1990 | Mackin |
| 5,037,404 A | 8/1991 | Gold et al. |
| 5,053,047 A | 10/1991 | Yoon |
| 5,057,092 A | 10/1991 | Webster, Jr. |
| 5,064,431 A | 11/1991 | Gilbertson et al. |
| 5,084,058 A | 1/1992 | Li |
| 5,103,804 A | 4/1992 | Abele et al. |
| 5,125,909 A | 6/1992 | Heimberger |
| 5,133,723 A | 7/1992 | Li et al. |
| 5,152,744 A | 10/1992 | Krause et al. |
| 5,195,990 A | 5/1993 | Weldon |
| 5,221,255 A | 6/1993 | Mahurkar et al. |
| 5,242,456 A | 9/1993 | Nash et al. |
| 5,242,457 A | 9/1993 | Akopov et al. |
| 5,254,107 A | 10/1993 | Soltesz |
| 5,257,975 A | 11/1993 | Foshee |
| D345,419 S | 3/1994 | Horrigan et al. |
| 5,312,341 A | 5/1994 | Turi |
| 5,314,407 A | 5/1994 | Auth et al. |
| 5,324,298 A | 6/1994 | Phillips et al. |
| 5,344,439 A | 9/1994 | Otten |
| 5,346,500 A | 9/1994 | Suchart |
| 5,358,479 A | 10/1994 | Wilson |
| 5,364,407 A | 11/1994 | Poll |
| 5,366,479 A | 11/1994 | McGarry et al. |
| 5,368,564 A | 11/1994 | Savage |
| 5,368,591 A | 11/1994 | Lennox et al. |
| 5,381,782 A | 1/1995 | DeLaRama et al. |
| 5,383,905 A | 1/1995 | Golds et al. |
| 5,399,164 A | 3/1995 | Snoke et al. |
| 5,403,348 A | 4/1995 | Bonutti |
| 5,409,483 A | 4/1995 | Campbell et al. |
| 5,415,666 A | 5/1995 | Gourlay et al. |
| 5,417,700 A | 5/1995 | Egan |
| 5,423,837 A | 6/1995 | Mericle et al. |
| 5,437,680 A | 8/1995 | Yoon |
| 5,439,470 A | 8/1995 | Li |
| 5,445,625 A | 8/1995 | Voda |
| 5,450,860 A | 9/1995 | O'Connor |
| 5,452,513 A | 9/1995 | Zinnbauer et al. |
| 5,474,572 A | 12/1995 | Hayhurst |
| 5,507,725 A | 4/1996 | Savage et al. |
| 5,520,702 A | 5/1996 | Sauer et al. |
| 5,522,873 A | 6/1996 | Jackman et al. |
| 5,524,630 A | 6/1996 | Crowley |
| 5,527,323 A | 6/1996 | Jervis et al. |
| 5,542,924 A | 8/1996 | Snoke et al. |
| 5,545,134 A | 8/1996 | Hilaire et al. |
| 5,545,168 A | 8/1996 | Burke |
| 5,565,122 A | 10/1996 | Zinnbauer et al. |
| 5,569,218 A | 10/1996 | Berg |
| 5,571,215 A | 11/1996 | Sterman et al. |
| 5,591,194 A | 1/1997 | Berthiaume |
| 5,624,397 A | 4/1997 | Snoke et al. |
| 5,626,614 A | 5/1997 | Hart |
| 5,630,824 A | 5/1997 | Hart |
| 5,640,955 A | 6/1997 | Ockuly et al. |
| 5,643,289 A | 7/1997 | Sauer et al. |
| 5,669,917 A | 9/1997 | Sauer et al. |
| 5,674,197 A | 10/1997 | Van Muiden et al. |
| 5,674,279 A | 10/1997 | Wright et al. |
| 5,690,655 A | 11/1997 | Hart et al. |
| 5,695,505 A | 12/1997 | Yoon |
| 5,701,905 A | 12/1997 | Esch |
| 5,709,695 A | 1/1998 | Northrup, III |
| 5,713,950 A | 2/1998 | Cox |
| 5,716,370 A | 2/1998 | Williamson, IV et al. |
| 5,718,725 A | 2/1998 | Sterman et al. |
| 5,725,542 A | 3/1998 | Yoon |
| 5,735,290 A | 4/1998 | Sterman et al. |
| 5,741,260 A | 4/1998 | Songer et al. |
| 5,741,301 A | 4/1998 | Pagedas |
| 5,752,518 A | 5/1998 | McGee et al. |
| 5,752,964 A | 5/1998 | Mericle |
| 5,752,966 A | 5/1998 | Chang |
| 5,755,730 A | 5/1998 | Swain et al. |
| 5,766,189 A | 6/1998 | Matsuno |
| 5,766,240 A | 6/1998 | Johnson |
| 5,769,812 A | 6/1998 | Stevens et al. |
| 5,769,830 A | 6/1998 | Parker |
| 5,779,673 A | 7/1998 | Roth et al. |
| 5,779,718 A | 7/1998 | Green et al. |

(56) References Cited

U.S. PATENT DOCUMENTS

| | | | |
|---|---|---|---|
| 5,807,403 A | 9/1998 | Beyar et al. |
| 5,810,848 A | 9/1998 | Hayhurst |
| 5,810,853 A | 9/1998 | Yoon |
| 5,817,107 A | 10/1998 | Schaller |
| 5,827,171 A | 10/1998 | Dobak, III et al. |
| 5,833,632 A | 11/1998 | Jacobsen et al. |
| 5,843,169 A | 12/1998 | Taheri |
| 5,848,969 A | 12/1998 | Panescu et al. |
| 5,849,035 A | 12/1998 | Pathak et al. |
| 5,860,992 A | 1/1999 | Daniel et al. |
| 5,860,993 A | 1/1999 | Thompson et al. |
| 5,861,003 A | 1/1999 | Latson et al. |
| 5,868,733 A | 2/1999 | Ockuly et al. |
| 5,879,371 A | 3/1999 | Gardiner et al. |
| 5,885,238 A | 3/1999 | Stevens et al. |
| 5,888,240 A | 3/1999 | Carpentier et al. |
| 5,897,537 A | 4/1999 | Berg et al. |
| 5,902,321 A | 5/1999 | Caspari et al. |
| 5,904,651 A | 5/1999 | Swanson et al. |
| 5,904,657 A | 5/1999 | Unsworth et al. |
| 5,906,579 A | 5/1999 | Vander Salm et al. |
| 5,911,715 A | 6/1999 | Berg et al. |
| 5,916,147 A | 6/1999 | Boury |
| 5,919,208 A | 7/1999 | Valenti |
| 5,935,149 A | 8/1999 | Ek |
| 5,947,983 A | 9/1999 | Solar et al. |
| 5,961,440 A | 10/1999 | Schweich, Jr. et al. |
| 5,961,539 A | 10/1999 | Northrup, III et al. |
| 5,971,975 A | 10/1999 | Mills et al. |
| 5,972,004 A | 10/1999 | Williamson, IV et al. |
| 5,976,120 A | 11/1999 | Chow et al. |
| 5,984,933 A | 11/1999 | Yoon |
| 5,989,284 A | 11/1999 | Laufer |
| 5,991,650 A | 11/1999 | Swanson et al. |
| 6,010,531 A | 1/2000 | Donlon et al. |
| 6,013,083 A | 1/2000 | Bennet |
| 6,015,428 A | 1/2000 | Pagedas |
| 6,029,671 A | 2/2000 | Stevens et al. |
| 6,050,936 A | 4/2000 | Schweich, Jr. et al. |
| 6,056,743 A | 5/2000 | Ellis et al. |
| 6,059,715 A | 5/2000 | Schweich, Jr. et al. |
| 6,066,160 A | 5/2000 | Colvin et al. |
| 6,074,401 A | 6/2000 | Gardiner et al. |
| 6,077,214 A | 6/2000 | Mortier et al. |
| 6,077,989 A | 6/2000 | Kandel et al. |
| 6,080,182 A | 6/2000 | Shaw et al. |
| 6,099,553 A | 8/2000 | Hart et al. |
| 6,110,184 A * | 8/2000 | Weadock ............ A61B 17/0057 148/213 |
| 6,125,852 A | 10/2000 | Stevens et al. |
| 6,149,658 A | 11/2000 | Gardiner et al. |
| 6,156,044 A | 12/2000 | Kammerer et al. |
| 6,159,187 A | 12/2000 | Park et al. |
| 6,162,168 A | 12/2000 | Schweich, Jr. et al. |
| 6,165,183 A | 12/2000 | Kuehn et al. |
| 6,168,588 B1 | 1/2001 | Wilson |
| 6,183,469 B1 | 2/2001 | Thapliyal et al. |
| 6,197,017 B1 | 3/2001 | Brock et al. |
| 6,199,262 B1 | 3/2001 | Martin |
| 6,203,531 B1 | 3/2001 | Ockuly et al. |
| 6,210,432 B1 | 4/2001 | Solem et al. |
| 6,228,096 B1 | 5/2001 | Marchand |
| 6,250,308 B1 | 6/2001 | Cox |
| 6,254,620 B1 | 7/2001 | Koh et al. |
| 6,258,118 B1 | 7/2001 | Baum et al. |
| 6,260,552 B1 | 7/2001 | Mortier et al. |
| 6,269,819 B1 | 8/2001 | Oz et al. |
| 6,283,993 B1 | 9/2001 | Cosgrove et al. |
| 6,306,149 B1 | 10/2001 | Meade |
| 6,312,447 B1 | 11/2001 | Grimes |
| 6,328,727 B1 | 12/2001 | Frazier et al. |
| 6,332,893 B1 | 12/2001 | Mortier et al. |
| 6,355,030 B1 | 3/2002 | Aldrich et al. |
| 6,378,289 B1 | 4/2002 | Trudeau et al. |
| 6,391,048 B1 | 5/2002 | Ginn et al. |
| 6,406,420 B1 | 6/2002 | McCarthy et al. |
| 6,409,743 B1 | 6/2002 | Fenton, Jr. |
| 6,423,088 B1 | 7/2002 | Fenton, Jr. |
| 6,428,562 B2 | 8/2002 | Bonutti |
| 6,432,123 B2 | 8/2002 | Schwartz et al. |
| 6,461,327 B1 | 10/2002 | Addis et al. |
| 6,491,689 B1 | 12/2002 | Ellis et al. |
| 6,514,265 B2 | 2/2003 | Ho et al. |
| 6,524,338 B1 | 2/2003 | Gundry |
| 6,533,753 B1 | 3/2003 | Haarstad et al. |
| 6,540,755 B2 | 4/2003 | Ockuly et al. |
| 6,551,332 B1 | 4/2003 | Nguyen et al. |
| 6,575,971 B2 | 6/2003 | Hauck et al. |
| 6,589,160 B2 | 7/2003 | Schweich, Jr. et al. |
| 6,591,472 B1 | 7/2003 | Noone et al. |
| 6,595,983 B2 | 7/2003 | Voda |
| 6,602,288 B1 | 8/2003 | Cosgrove et al. |
| 6,602,289 B1 | 8/2003 | Colvin et al. |
| 6,607,541 B1 | 8/2003 | Gardiner et al. |
| 6,610,087 B1 | 8/2003 | Zarbatany et al. |
| 6,613,059 B2 | 9/2003 | Schaller et al. |
| 6,619,291 B2 | 9/2003 | Hlavka et al. |
| 6,626,899 B2 | 9/2003 | Houser et al. |
| 6,629,534 B1 | 10/2003 | St. Goar et al. |
| 6,641,593 B1 | 11/2003 | Schaller et al. |
| 6,645,160 B1 | 11/2003 | Heesch |
| 6,648,874 B2 | 11/2003 | Parisi et al. |
| 6,648,903 B1 | 11/2003 | Pierson, III |
| 6,651,671 B1 | 11/2003 | Donlon et al. |
| 6,655,386 B1 | 12/2003 | Makower et al. |
| 6,669,687 B1 | 12/2003 | Saadat |
| 6,676,702 B2 | 1/2004 | Mathis |
| 6,689,164 B1 | 2/2004 | Seguin |
| 6,695,793 B2 | 2/2004 | Brennan et al. |
| 6,699,263 B2 | 3/2004 | Cope |
| 6,702,826 B2 | 3/2004 | Liddicoat et al. |
| 6,716,243 B1 | 4/2004 | Colvin et al. |
| 6,718,985 B2 | 4/2004 | Hlavka et al. |
| 6,723,038 B1 | 4/2004 | Schroeder et al. |
| 6,723,107 B1 | 4/2004 | Skiba et al. |
| 6,733,509 B2 | 5/2004 | Nobles et al. |
| 6,746,471 B2 | 6/2004 | Mortier et al. |
| 6,749,560 B1 | 6/2004 | Konstorum et al. |
| 6,752,813 B2 | 6/2004 | Goldfarb et al. |
| 6,790,231 B2 | 9/2004 | Liddicoat et al. |
| 6,793,618 B2 | 9/2004 | Schweich, Jr. et al. |
| 6,818,001 B2 | 11/2004 | Wulfman et al. |
| 6,849,077 B2 | 2/2005 | Ricci |
| 6,908,424 B2 | 6/2005 | Mortier et al. |
| 6,923,818 B2 | 8/2005 | Muramatsu et al. |
| 6,932,792 B1 | 8/2005 | St. Goar et al. |
| 6,951,557 B2 | 10/2005 | Ellis et al. |
| 6,976,995 B2 | 12/2005 | Mathis et al. |
| 6,986,775 B2 | 1/2006 | Morales et al. |
| 6,989,025 B2 | 1/2006 | Burgmeier et al. |
| 6,991,643 B2 | 1/2006 | Saadat |
| 6,997,931 B2 | 2/2006 | Sauer et al. |
| 7,004,958 B2 | 2/2006 | Adams et al. |
| 7,037,334 B1 | 5/2006 | Hlavka et al. |
| 7,048,754 B2 | 5/2006 | Martin et al. |
| 7,090,683 B2 | 8/2006 | Brock et al. |
| 7,101,395 B2 | 9/2006 | Tremulis et al. |
| 7,125,421 B2 | 10/2006 | Tremulis et al. |
| 7,166,127 B2 | 1/2007 | Spence et al. |
| 7,186,262 B2 | 3/2007 | Saadat |
| 7,189,199 B2 | 3/2007 | McCarthy et al. |
| 7,214,230 B2 | 5/2007 | Brock et al. |
| 7,226,467 B2 | 6/2007 | Lucatero et al. |
| 7,232,422 B2 | 6/2007 | Gibson et al. |
| 7,235,086 B2 | 6/2007 | Sauer et al. |
| 7,241,310 B2 | 7/2007 | Taylor et al. |
| 7,257,450 B2 | 8/2007 | Auth et al. |
| 7,276,062 B2 | 10/2007 | McDaniel et al. |
| 7,306,585 B2 | 12/2007 | Ross |
| 7,326,231 B2 | 2/2008 | Phillips et al. |
| 7,331,972 B1 | 2/2008 | Cox |
| 7,344,544 B2 | 3/2008 | Bender et al. |
| 7,452,325 B2 | 11/2008 | Schaller |
| 7,534,204 B2 | 5/2009 | Starksen et al. |

(56) References Cited

U.S. PATENT DOCUMENTS

| | | |
|---|---|---|
| 7,588,582 B2 | 9/2009 | Starksen et al. |
| 7,618,449 B2 | 11/2009 | Tremulis et al. |
| 7,632,308 B2 | 12/2009 | Loulmet |
| 7,666,193 B2 | 2/2010 | Starksen et al. |
| 7,722,523 B2 | 5/2010 | Mortier et al. |
| 7,740,638 B2 | 6/2010 | Hyde |
| 7,753,858 B2 | 7/2010 | Starksen et al. |
| 7,753,924 B2 | 7/2010 | Starksen et al. |
| 7,766,812 B2 | 8/2010 | Schroeder et al. |
| 7,776,812 B2 | 8/2010 | Lang et al. |
| 7,832,406 B2 | 11/2010 | Ellis et al. |
| 7,850,600 B1 | 12/2010 | Piskun |
| 7,883,538 B2 | 2/2011 | To et al. |
| 7,918,787 B2 | 4/2011 | Saadat |
| 8,096,985 B2 | 1/2012 | Legaspi et al. |
| 8,343,173 B2 | 1/2013 | Starksen et al. |
| 8,388,680 B2 | 3/2013 | Starksen et al. |
| 8,882,713 B1 | 11/2014 | Call et al. |
| 9,173,646 B2 | 11/2015 | Fabro |
| 9,616,197 B2 | 4/2017 | Serina et al. |
| 10,058,321 B2 | 8/2018 | Sampson et al. |
| 2001/0005787 A1 | 6/2001 | Oz et al. |
| 2001/0014800 A1 | 8/2001 | Frazier et al. |
| 2001/0023332 A1 | 9/2001 | Hahnen |
| 2001/0031979 A1 | 10/2001 | Ricci |
| 2001/0041821 A1 | 11/2001 | Wilk |
| 2001/0047165 A1 | 11/2001 | Makower et al. |
| 2002/0007190 A1 | 1/2002 | Wulfman et al. |
| 2002/0013571 A1 | 1/2002 | Goldfarb et al. |
| 2002/0013621 A1 | 1/2002 | Stobie et al. |
| 2002/0026201 A1 | 2/2002 | Foerster et al. |
| 2002/0029080 A1 | 3/2002 | Mortier et al. |
| 2002/0035361 A1 | 3/2002 | Houser et al. |
| 2002/0035393 A1 | 3/2002 | Lashinksi et al. |
| 2002/0042621 A1 | 4/2002 | Liddicoat et al. |
| 2002/0065536 A1 | 5/2002 | Hart et al. |
| 2002/0072757 A1 | 6/2002 | Ahmed et al. |
| 2002/0077524 A1 | 6/2002 | Schweich, Jr. et al. |
| 2002/0087048 A1 | 7/2002 | Brock et al. |
| 2002/0087049 A1 | 7/2002 | Brock et al. |
| 2002/0087148 A1 | 7/2002 | Brock et al. |
| 2002/0087169 A1 | 7/2002 | Brock et al. |
| 2002/0095167 A1 | 7/2002 | Liddicoat et al. |
| 2002/0095175 A1 | 7/2002 | Brock et al. |
| 2002/0133092 A1 | 9/2002 | Oslund et al. |
| 2002/0138044 A1 | 9/2002 | Streeter et al. |
| 2002/0156526 A1 | 10/2002 | Hlavka et al. |
| 2002/0161378 A1 | 10/2002 | Downing |
| 2002/0165486 A1 | 11/2002 | Bertolero et al. |
| 2002/0173841 A1 | 11/2002 | Ortiz et al. |
| 2002/0183787 A1 | 12/2002 | Wahr et al. |
| 2002/0183835 A1 | 12/2002 | Taylor et al. |
| 2002/0193815 A1 | 12/2002 | Foerster et al. |
| 2002/0198536 A1 | 12/2002 | Trout, III et al. |
| 2003/0009196 A1 | 1/2003 | Peterson |
| 2003/0014060 A1 | 1/2003 | Wilson |
| 2003/0018358 A1 | 1/2003 | Saadat |
| 2003/0032979 A1 | 2/2003 | Mortier et al. |
| 2003/0033006 A1 | 2/2003 | Phillips et al. |
| 2003/0045893 A1 | 3/2003 | Ginn |
| 2003/0060813 A1 | 3/2003 | Loeb et al. |
| 2003/0069577 A1 | 4/2003 | Vaska et al. |
| 2003/0069593 A1 | 4/2003 | Tremulis et al. |
| 2003/0074012 A1 | 4/2003 | Nguyen et al. |
| 2003/0078465 A1 | 4/2003 | Pai et al. |
| 2003/0078601 A1 | 4/2003 | Shikhman et al. |
| 2003/0078603 A1 | 4/2003 | Schaller et al. |
| 2003/0093118 A1 | 5/2003 | Ho et al. |
| 2003/0105520 A1 | 6/2003 | Alferness et al. |
| 2003/0125739 A1 | 7/2003 | Bagga et al. |
| 2003/0125767 A1 | 7/2003 | Collier et al. |
| 2003/0130731 A1 | 7/2003 | Vidlund et al. |
| 2003/0144697 A1 | 7/2003 | Mathis et al. |
| 2003/0158464 A1 | 8/2003 | Bertolero |
| 2003/0158581 A1 | 8/2003 | Levinson |
| 2003/0167062 A1 | 9/2003 | Gambale et al. |
| 2003/0167071 A1 | 9/2003 | Martin et al. |
| 2003/0171736 A1 | 9/2003 | Bon |
| 2003/0171776 A1 | 9/2003 | Adams et al. |
| 2003/0199974 A1 | 10/2003 | Lee et al. |
| 2003/0220685 A1 | 11/2003 | Hlvaka et al. |
| 2003/0225420 A1 | 12/2003 | Wardle |
| 2003/0233105 A1 | 12/2003 | Gayton |
| 2003/0233142 A1 | 12/2003 | Morales et al. |
| 2003/0236535 A1 | 12/2003 | Onuki et al. |
| 2004/0003819 A1 | 1/2004 | St. Goar et al. |
| 2004/0019378 A1 | 1/2004 | Hlavka et al. |
| 2004/0024414 A1 | 2/2004 | Downing |
| 2004/0030382 A1 | 2/2004 | St. Goar et al. |
| 2004/0039442 A1 | 2/2004 | St. Goar et al. |
| 2004/0092962 A1 | 5/2004 | Thornton et al. |
| 2004/0093024 A1 | 5/2004 | Lousararian et al. |
| 2004/0093044 A1 | 5/2004 | Rychnovsky et al. |
| 2004/0097788 A1 | 5/2004 | Mourlas et al. |
| 2004/0118415 A1 | 6/2004 | Hall et al. |
| 2004/0122450 A1 | 6/2004 | Oren et al. |
| 2004/0138683 A1 | 7/2004 | Shelton et al. |
| 2004/0148020 A1 | 7/2004 | Vidlund et al. |
| 2004/0152947 A1 | 8/2004 | Schroeder et al. |
| 2004/0172046 A1 | 9/2004 | Hlavka et al. |
| 2004/0181238 A1 | 9/2004 | Zarbatany et al. |
| 2004/0186378 A1 | 9/2004 | Gesswein |
| 2004/0186486 A1 | 9/2004 | Roue et al. |
| 2004/0193191 A1 | 9/2004 | Starksen et al. |
| 2004/0204724 A1 | 10/2004 | Kissel et al. |
| 2004/0210238 A1 | 10/2004 | Nobles et al. |
| 2004/0236372 A1 | 11/2004 | Anspach, III et al. |
| 2004/0236419 A1 | 11/2004 | Milo |
| 2004/0243102 A1 | 12/2004 | Berg et al. |
| 2004/0243227 A1 | 12/2004 | Starksen et al. |
| 2004/0260317 A1 | 12/2004 | Bloom et al. |
| 2005/0054919 A1 | 3/2005 | Spear et al. |
| 2005/0055052 A1 | 3/2005 | Lombardo et al. |
| 2005/0055087 A1 | 3/2005 | Starksen |
| 2005/0065550 A1 | 3/2005 | Starksen et al. |
| 2005/0075654 A1 | 4/2005 | Kelleher |
| 2005/0075723 A1 | 4/2005 | Schroeder et al. |
| 2005/0080454 A1 | 4/2005 | Drews et al. |
| 2005/0107810 A1 | 5/2005 | Morales et al. |
| 2005/0107811 A1 | 5/2005 | Starksen et al. |
| 2005/0107812 A1 | 5/2005 | Starksen et al. |
| 2005/0119523 A1 | 6/2005 | Starksen et al. |
| 2005/0119673 A1 | 6/2005 | Gordon et al. |
| 2005/0119734 A1 | 6/2005 | Spence et al. |
| 2005/0119735 A1 | 6/2005 | Spence et al. |
| 2005/0137689 A1 | 6/2005 | Salahieh et al. |
| 2005/0184122 A1 | 8/2005 | Hlavka et al. |
| 2005/0192629 A1 | 9/2005 | Saadat et al. |
| 2005/0197694 A1 | 9/2005 | Pai et al. |
| 2005/0209690 A1 | 9/2005 | Mathis et al. |
| 2005/0216078 A1 | 9/2005 | Starksen et al. |
| 2005/0228452 A1 | 10/2005 | Mourlas et al. |
| 2005/0251157 A1 | 11/2005 | Saadat et al. |
| 2005/0251159 A1 | 11/2005 | Ewers et al. |
| 2005/0251166 A1 | 11/2005 | Vaughan et al. |
| 2005/0251177 A1 | 11/2005 | Saadat et al. |
| 2005/0251205 A1 | 11/2005 | Ewers et al. |
| 2005/0251207 A1 | 11/2005 | Flores et al. |
| 2005/0251208 A1 | 11/2005 | Elmer et al. |
| 2005/0251209 A1 | 11/2005 | Saadat et al. |
| 2005/0251210 A1 | 11/2005 | Westra et al. |
| 2005/0273128 A1 | 12/2005 | Reil |
| 2005/0273138 A1 | 12/2005 | To et al. |
| 2005/0277966 A1 | 12/2005 | Ewers et al. |
| 2005/0277981 A1 | 12/2005 | Maahs et al. |
| 2005/0277983 A1 | 12/2005 | Saadat et al. |
| 2006/0025750 A1 | 2/2006 | Starksen et al. |
| 2006/0025784 A1 | 2/2006 | Starksen et al. |
| 2006/0025787 A1 | 2/2006 | Morales et al. |
| 2006/0058817 A1 | 3/2006 | Starksen et al. |
| 2006/0069429 A1 | 3/2006 | Spence et al. |
| 2006/0089618 A1 | 4/2006 | McFerran et al. |
| 2006/0122633 A1 | 6/2006 | To et al. |
| 2006/0129188 A1 | 6/2006 | Starksen et al. |

(56) References Cited

U.S. PATENT DOCUMENTS

| | | |
|---|---|---|
| 2006/0155363 A1 | 7/2006 | LaDuca et al. |
| 2006/0161040 A1 | 7/2006 | McCarthy et al. |
| 2006/0161177 A1 | 7/2006 | Worley et al. |
| 2006/0178682 A1 | 8/2006 | Boehlke |
| 2006/0184203 A1 | 8/2006 | Martin et al. |
| 2006/0190030 A1 | 8/2006 | To et al. |
| 2006/0229697 A1* | 10/2006 | Gerdts ............... A61F 2/95 623/1.11 |
| 2006/0229708 A1 | 10/2006 | Powell et al. |
| 2006/0241340 A1 | 10/2006 | Schroeder et al. |
| 2006/0241656 A1 | 10/2006 | Starksen et al. |
| 2006/0264975 A1 | 11/2006 | Pipenhagen et al. |
| 2006/0270976 A1 | 11/2006 | Savage et al. |
| 2006/0271101 A1 | 11/2006 | Saadat et al. |
| 2006/0287661 A1 | 12/2006 | Bolduc et al. |
| 2007/0005081 A1 | 1/2007 | Findlay, III et al. |
| 2007/0005394 A1 | 1/2007 | Bleyendaal et al. |
| 2007/0010852 A1 | 1/2007 | Blaeser et al. |
| 2007/0010857 A1 | 1/2007 | Sugimoto et al. |
| 2007/0016250 A1 | 1/2007 | Blaeser et al. |
| 2007/0016287 A1 | 1/2007 | Cartledge et al. |
| 2007/0032820 A1 | 2/2007 | Chin-Chen et al. |
| 2007/0038293 A1 | 2/2007 | St. Goar et al. |
| 2007/0049942 A1 | 3/2007 | Hindrichs et al. |
| 2007/0051377 A1 | 3/2007 | Douk et al. |
| 2007/0055206 A1 | 3/2007 | To et al. |
| 2007/0060880 A1 | 3/2007 | Gregorich et al. |
| 2007/0066994 A1 | 3/2007 | Blaeser et al. |
| 2007/0093805 A1 | 4/2007 | Auth et al. |
| 2007/0100356 A1 | 5/2007 | Lucatero et al. |
| 2007/0112244 A1 | 5/2007 | McCarthy et al. |
| 2007/0112422 A1 | 5/2007 | Dehdashtian |
| 2007/0112424 A1 | 5/2007 | Spence et al. |
| 2007/0112425 A1 | 5/2007 | Schaller et al. |
| 2007/0135830 A1 | 6/2007 | Schaeffer |
| 2007/0250042 A1 | 10/2007 | Kiemeneij |
| 2008/0045977 A1 | 2/2008 | To et al. |
| 2008/0045982 A1 | 2/2008 | To et al. |
| 2008/0045983 A1 | 2/2008 | To et al. |
| 2008/0051703 A1 | 2/2008 | Thornton et al. |
| 2008/0051810 A1 | 2/2008 | To et al. |
| 2008/0051832 A1 | 2/2008 | To et al. |
| 2008/0051837 A1 | 2/2008 | To et al. |
| 2008/0058765 A1 | 3/2008 | Jais et al. |
| 2008/0058868 A1 | 3/2008 | To et al. |
| 2008/0065156 A1 | 3/2008 | Hauser et al. |
| 2008/0097489 A1 | 4/2008 | Goldfarb et al. |
| 2008/0103439 A1 | 5/2008 | Torrance et al. |
| 2008/0114364 A1 | 5/2008 | Goldin et al. |
| 2008/0119882 A1 | 5/2008 | Cox |
| 2008/0177380 A1 | 7/2008 | Starksen et al. |
| 2008/0228032 A1 | 9/2008 | Starksen et al. |
| 2008/0234701 A1 | 9/2008 | Morales et al. |
| 2008/0234702 A1 | 9/2008 | Morales et al. |
| 2008/0234704 A1 | 9/2008 | Starksen et al. |
| 2008/0234728 A1 | 9/2008 | Starksen et al. |
| 2008/0234815 A1 | 9/2008 | Starksen et al. |
| 2008/0243150 A1 | 10/2008 | Starksen et al. |
| 2008/0287828 A1 | 11/2008 | Burbank et al. |
| 2008/0294177 A1 | 11/2008 | To et al. |
| 2008/0314394 A9 | 12/2008 | Ellis et al. |
| 2009/0012541 A1* | 1/2009 | Dahl ............... A61B 17/0401 606/151 |
| 2009/0182417 A1 | 7/2009 | Tremulis et al. |
| 2009/0198216 A1 | 8/2009 | Muni et al. |
| 2009/0222083 A1 | 9/2009 | Nguyen et al. |
| 2009/0234318 A1 | 9/2009 | Loulmet et al. |
| 2009/0276038 A1 | 11/2009 | Tremulis et al. |
| 2010/0023056 A1 | 1/2010 | Johansson et al. |
| 2010/0049213 A1 | 2/2010 | Serina et al. |
| 2010/0076408 A1 | 3/2010 | Krever et al. |
| 2010/0076548 A1 | 3/2010 | Konno |
| 2010/0082098 A1 | 4/2010 | Starksen et al. |
| 2010/0094213 A1 | 4/2010 | Horn et al. |
| 2010/0094314 A1 | 4/2010 | Hernlund et al. |
| 2010/0121349 A1 | 5/2010 | Meier et al. |
| 2010/0145267 A1 | 6/2010 | Bishop et al. |
| 2010/0185172 A1 | 7/2010 | Fabro |
| 2010/0198056 A1 | 8/2010 | Fabro et al. |
| 2010/0198192 A1 | 8/2010 | Serina et al. |
| 2010/0198208 A1 | 8/2010 | Napp et al. |
| 2012/0029535 A1 | 2/2012 | Swain |
| 2012/0101442 A1 | 4/2012 | Legaspi et al. |
| 2012/0232565 A1 | 9/2012 | Kveen et al. |
| 2013/0030178 A1 | 1/2013 | Rodriguez |
| 2013/0304093 A1 | 11/2013 | Serina et al. |
| 2016/0220785 A1 | 8/2016 | Fabro |
| 2017/0361065 A1 | 12/2017 | Legaspi et al. |
| 2018/0043132 A1 | 2/2018 | Serina et al. |
| 2019/0008505 A1 | 1/2019 | Sampson et al. |

FOREIGN PATENT DOCUMENTS

| | | |
|---|---|---|
| EP | 1 920 795 A1 | 5/2008 |
| EP | 2433571 A2 | 3/2012 |
| JP | 6-237939 A | 8/1994 |
| JP | 9-289989 A | 11/1997 |
| JP | 10-506812 A | 7/1998 |
| JP | 11-318910 A | 11/1999 |
| JP | 2000-505336 A | 5/2000 |
| JP | 2001-500749 A | 1/2001 |
| JP | 2003-500121 A | 1/2003 |
| JP | 2004-500170 A | 1/2004 |
| JP | 2004-321343 A | 11/2004 |
| JP | 2005-021576 A | 1/2005 |
| WO | WO-94/03227 A1 | 2/1994 |
| WO | WO-95/15715 A1 | 6/1995 |
| WO | WO-96/08208 A1 | 3/1996 |
| WO | WO-96/10365 A1 | 4/1996 |
| WO | WO-96/39942 A1 | 12/1996 |
| WO | WO-97/27799 A1 | 8/1997 |
| WO | WO-97/27807 A1 | 8/1997 |
| WO | WO-97/29709 A1 | 8/1997 |
| WO | WO-97/30638 A1 | 8/1997 |
| WO | WO-98/07375 A1 | 2/1998 |
| WO | WO-98/46142 A1 | 10/1998 |
| WO | WO-99/59477 A1 | 11/1999 |
| WO | WO-00/60995 A2 | 10/2000 |
| WO | WO-00/60995 A3 | 10/2000 |
| WO | WO-00/67640 A2 | 11/2000 |
| WO | WO-00/67640 A3 | 11/2000 |
| WO | WO-00/71195 A1 | 11/2000 |
| WO | WO-01/19256 A1 | 3/2001 |
| WO | WO-01/26586 A1 | 4/2001 |
| WO | WO-01/37742 A2 | 5/2001 |
| WO | WO-01/37742 A3 | 5/2001 |
| WO | WO-01/54618 A1 | 8/2001 |
| WO | WO-02/00099 A2 | 1/2002 |
| WO | WO-02/00099 A3 | 1/2002 |
| WO | WO-02/03892 A1 | 1/2002 |
| WO | WO-2002/030310 A1 | 4/2002 |
| WO | WO-02/051329 A1 | 7/2002 |
| WO | WO-02/053011 A2 | 7/2002 |
| WO | WO-02/053011 A3 | 7/2002 |
| WO | WO-02/085251 A1 | 10/2002 |
| WO | WO-02/085252 A1 | 10/2002 |
| WO | WO-03/073913 A2 | 9/2003 |
| WO | WO-03/088875 A1 | 10/2003 |
| WO | WO-03/105667 A2 | 12/2003 |
| WO | WO-03/105667 A3 | 12/2003 |
| WO | WO-03/105670 A2 | 12/2003 |
| WO | WO-03/105670 A3 | 12/2003 |
| WO | WO-2004/037317 A2 | 5/2004 |
| WO | WO-2004/037317 A3 | 5/2004 |
| WO | WO-2004/082523 A2 | 9/2004 |
| WO | WO-2004/082523 A3 | 9/2004 |
| WO | WO-2004/082538 A2 | 9/2004 |
| WO | WO-2004/082538 A3 | 9/2004 |
| WO | WO-2004/112658 A1 | 12/2004 |
| WO | WO-2005/025644 A2 | 3/2005 |
| WO | WO-2005/062931 A2 | 7/2005 |
| WO | WO-2005/062931 A3 | 7/2005 |
| WO | WO-2005/102181 A1 | 11/2005 |
| WO | WO-2006/034243 A2 | 3/2006 |

(56) References Cited

FOREIGN PATENT DOCUMENTS

| | | | |
|---|---|---|---|
| WO | WO-2006/034243 A3 | 3/2006 |
| WO | WO-2006/037073 A2 | 4/2006 |
| WO | WO-2006/037073 A3 | 4/2006 |
| WO | WO-2006/097931 A2 | 9/2006 |
| WO | WO-2006/097931 A3 | 9/2006 |
| WO | WO-2006/116558 A2 | 11/2006 |
| WO | WO-2006/116558 A3 | 11/2006 |
| WO | WO-2006/116558 C2 | 11/2006 |
| WO | WO-2007/005495 A1 | 1/2007 |
| WO | WO-2007/021564 A1 | 2/2007 |
| WO | WO-2007/021834 A1 | 2/2007 |
| WO | WO-2007/035449 A2 | 3/2007 |
| WO | WO-2007/056502 A1 | 5/2007 |
| WO | WO-2007/059233 A2 | 5/2007 |
| WO | WO-2007/059233 A3 | 5/2007 |
| WO | WO-2007/100409 A2 | 9/2007 |
| WO | WO-2007/100409 A3 | 9/2007 |
| WO | WO-2008/028135 A2 | 3/2008 |
| WO | WO-2008/028135 A3 | 3/2008 |
| WO | WO-2008/042987 A2 | 4/2008 |
| WO | WO-2008/042987 A3 | 4/2008 |
| WO | WO-2008/048626 A2 | 4/2008 |
| WO | WO-2010/085456 A1 | 7/2010 |
| WO | WO-2010/085457 A1 | 7/2010 |

OTHER PUBLICATIONS

De Simone, R. et al. (Apr. 15, 1993). "Adjustable Tricuspid Valve Annuloplasty Assisted by Intraoperative Transesophageal Color Doppler Echocardiography," *Am. J. Cardiol.* 71(11):926-931.

Downing, S.W. et al. (2002). "Feasibility of Off-Pump ASD Closure Using Real-Time 3-D Echocardiography," *The Heart Surgery Forum* 5(2):96-99, Abstract 7025.

Extended European Search Report dated May 10, 2012, for EP Application No. 10 733 791.7, filed on Aug. 19, 2011, 9 pages.

Final Office Action dated Dec. 26, 2007, for U.S. Appl. No. 10/776,682, filed Feb. 10, 2004, 6 pages.

Final Office Action dated Jan. 12, 2009, for U.S. Appl. No. 10/776,682, filed Feb. 10, 2004, 8 pages.

Final Office Action dated May 8, 2009, for U.S. Appl. No. 11/201,949, filed Aug. 10, 2005, 10 pages.

Final Office Action dated Apr. 15, 2010, for U.S. Appl. No. 11/201,949, filed Aug. 10, 2005, 8 pages.

Final Office Action dated Oct. 22, 2010, for U.S. Appl. No. 10/776,682, filed Feb. 10, 2004, 10 pages.

Final Office Action dated Jun. 6, 2011, for U.S. Appl. No. 11/201,949, filed Aug. 10, 2005, 10 pages.

Final Office Action dated Nov. 28, 2011, for U.S. Appl. No. 11/201,949, filed Aug. 10, 2005, 8 pages.

Non-Final Office Action dated Jun. 22, 2012, for U.S. Appl. No. 12/657,390, filed Jan. 19, 2010, 10 pages.

Final Office Action dated Jan. 24, 2014, for U.S. Appl. No. 11/201,949, filed Aug. 10, 2005, 10 pages.

Final Office Action dated Apr. 14, 2014, for U.S. Appl. No. 13/619,331, filed Sep. 14, 2012, 7 pages.

Final Office Action dated Aug. 5, 2014, for U.S. Appl. No. 10/776,682, filed Feb. 10, 2004, 7 pages.

Final Office Action dated Jun. 7, 2017, for U.S. Appl. No. 15/061,748, filed Mar. 4, 2016, 18 pages.

Final Office Action dated Aug. 1, 2017, for U.S. Appl. No. 14/868,290, filed Sep. 28, 2015, 9 pages.

Final Office Action dated Aug. 11, 2016, for U.S. Appl. No. 14/052,593, filed Oct. 11, 2013, 9 pages.

International Search Report dated Apr. 2, 2007, for PCT Application No. PCT/US2006/043597, filed Nov. 8, 2006, 7 pages.

International Search Report dated Dec. 8, 2006, for PCT Application No. PCT/US2006/030260, filed Aug. 2, 2006, 3 pages.

International Search Report dated Dec. 19, 2006, for PCT Application No. PCT/US2006/031190, filed Aug. 10, 2006, 3 pages.

International Search Report dated Mar. 9, 2010, for PCT Patent Application No. PCT/US2010/021440, filed on Jan. 19, 2010, 1 page.

International Search Report dated Mar. 19, 2010, for PCT Patent Application No. PCT/US2010/021437, filed on Jan. 19, 2010, 1 page.

International Search Report and Written Opinion dated May 19, 2016, for PCT Application No. PCT/US2016/021065 filed on Mar. 4, 2016, 2 pages.

Nagy, Z.L. et al. (Dec. 2000). "Mitral Annuloplasty with a Suture Technique," *European Journal of Cardio-thoracic Surgery* 18(6):739-740.

Non-Final Office Action dated Oct. 23, 2006, for U.S. Appl. No. 10/776,682, filed Feb. 10, 2004, 14 pages.

Non-Final Office Action dated Nov. 30, 2006, for U.S. Appl. No. 10/776,682, filed Feb. 10, 2004, 14 pages.

Non-Final Office Action dated Aug. 6, 2008, for U.S. Appl. No. 10/776,682, filed Feb. 10, 2004, 7 pages.

Non-Final Office Action dated Nov. 26, 2008, for U.S. Appl. No. 11/201,949, filed Aug. 10, 2005, 7 pages.

Non-Final Office Action dated Jul. 6, 2009, for U.S. Appl. No. 10/776,682, filed Feb. 10, 2004, 9 pages.

Non-Final Office Action dated Oct. 1, 2009, for U.S. Appl. No. 11/201,949, filed Aug. 10, 2005, 10 pages.

Non-Final Office Action dated Apr. 15, 2010, for U.S. Appl. No. 10/776,682, filed Feb. 10, 2004, 9 pages.

Non-Final Office Action dated Sep. 14, 2010, for U.S. Appl. No. 11/201,949, filed Aug. 10, 2005, 10 pages.

Non-Final Office Action dated Oct. 18, 2011, for U.S. Appl. No. 10/776,682, filed Feb. 10, 2004, 7 pages.

Non-Final Office Action dated Mar. 15, 2012, for U.S. Appl. No. 12/690,109, filed Jan. 19, 2010, 7 pages.

Non-Final Office Action dated Apr. 11, 2013, for U.S. Appl. No. 12/657,422, filed Jan. 19, 2010, 8 pages.

Non-Final Office Action dated Jun. 21, 2013, for U.S. Appl. No. 11/201,949, filed Aug. 10, 2005, 8 pages.

Non-Final Office Action dated Oct. 3, 2013, for U.S. Appl. No. 10/776,682, filed Feb. 10, 2004, 7 pages.

Non-Final Office Action dated Dec. 18, 2014, for U.S. Appl. No. 13/619,331, filed Sep. 14, 2012, 7 pages.

Non-Final Office Action dated Sep. 15, 2015, for U.S. Appl. No. 14/052,593, filed Oct. 11, 2013, 8 pages.

Non-Final Office Action dated Dec. 19, 2016, for U.S. Appl. No. 15/061,748, filed Mar. 4, 2016, 14 pages.

Non-Final Office Action dated Sep. 28, 2017, for U.S. Appl. No. 15/061,748, filed Mar. 4, 2016, 16 pages.

Non-Final Office Action dated Jan. 5, 2017, for U.S. Appl. No. 14/868,290, filed Sep. 28, 2015, 8 pages.

Non-Final Office Action dated Mar. 29, 2018, for U.S. Appl. No. 14/868,290, filed Sep. 28, 2015, 9 pages.

Notice of Allowance dated Jun. 19, 2015, for U.S. Appl. No. 13/619,331, filed Sep. 14, 2012, 7 pages.

Notice of Allowance dated Feb. 23, 2017, for U.S. Appl. No. 14/052,593, filed Oct. 11, 2013, 9 pages.

Notice of Allowance dated May 22, 2018, for U.S. Appl. No. 15/061,748, filed Mar. 4, 2016, 12 pages.

Shumway, S.J. et al. (Dec. 1988). "A 'Designer' Annuloplasty Ring for Patients with Massive Mitral Annular Dilatation," *Ann. Thorac. Surg.* 46(6):695-696.

Supplementary European Search Report dated Apr. 27, 2012, for EP Patent Application No. 10 733 791.7, filed on Aug. 19, 2011, 4 pages.

Towne, W.D. (1973). "Letter to the Editor: Classification of Chordae Tendineae," *Circulation* 47:209.

U.S. Appl. No. 61/083,109, filed Jul. 23, 2008, by Johansson, Peter.
U.S. Appl. No. 61/104,681, filed Oct. 10, 2008, by Serina et al.
U.S. Appl. No. 61/104,686, filed Oct. 10, 2008, by To et al.
U.S. Appl. No. 61/145,964, filed Jan. 20, 2009, by Fabro, Mariel.
U.S. Appl. No. 61/160,018, filed Mar. 13, 2009, by Johansson, Peter.
U.S. Appl. No. 61/160,230, filed Mar. 13, 2009, by Meier et al.
U.S. Appl. No. 61/160,670, filed Mar. 16, 2009, by Fabro et al.
U.S. Appl. No. 61/178,910, filed May 15, 2009, by Serina et al.
U.S. Appl. No. 61/178,938, filed May 15, 2009, by Fabro, Mariel.

(56) References Cited

OTHER PUBLICATIONS

U.S. Appl. No. 62/128,628, filed Mar. 5, 2015, by Russel Sampson.
Written Opinion of the International Searching Authority dated Dec. 8, 2006, for PCT Application No. PCT/US2006/030260, filed Aug. 2, 2006, 7 pages.
Written Opinion of the International Searching Authority dated Mar. 9, 2010, for PCT Patent Application No. PCT/US/2010/021440, filed on Jan. 19, 2010, 5 pages.
Written Opinion of the International Searching Authority dated Mar. 19, 2010, for PCT Patent Application No. PCT/US/2010/021437, filed on Jan. 19, 2010, 8 pages.
Extended European Search Report dated Jan. 2, 2019 for EP Patent Application No. 16759631.1, filed on Mar. 4, 2016, 6 pages.
Final Office Action dated Dec. 4, 2018, for U.S. Appl. No. 14/868,290, filed Sep. 28, 2015, 9 pages.

\* cited by examiner

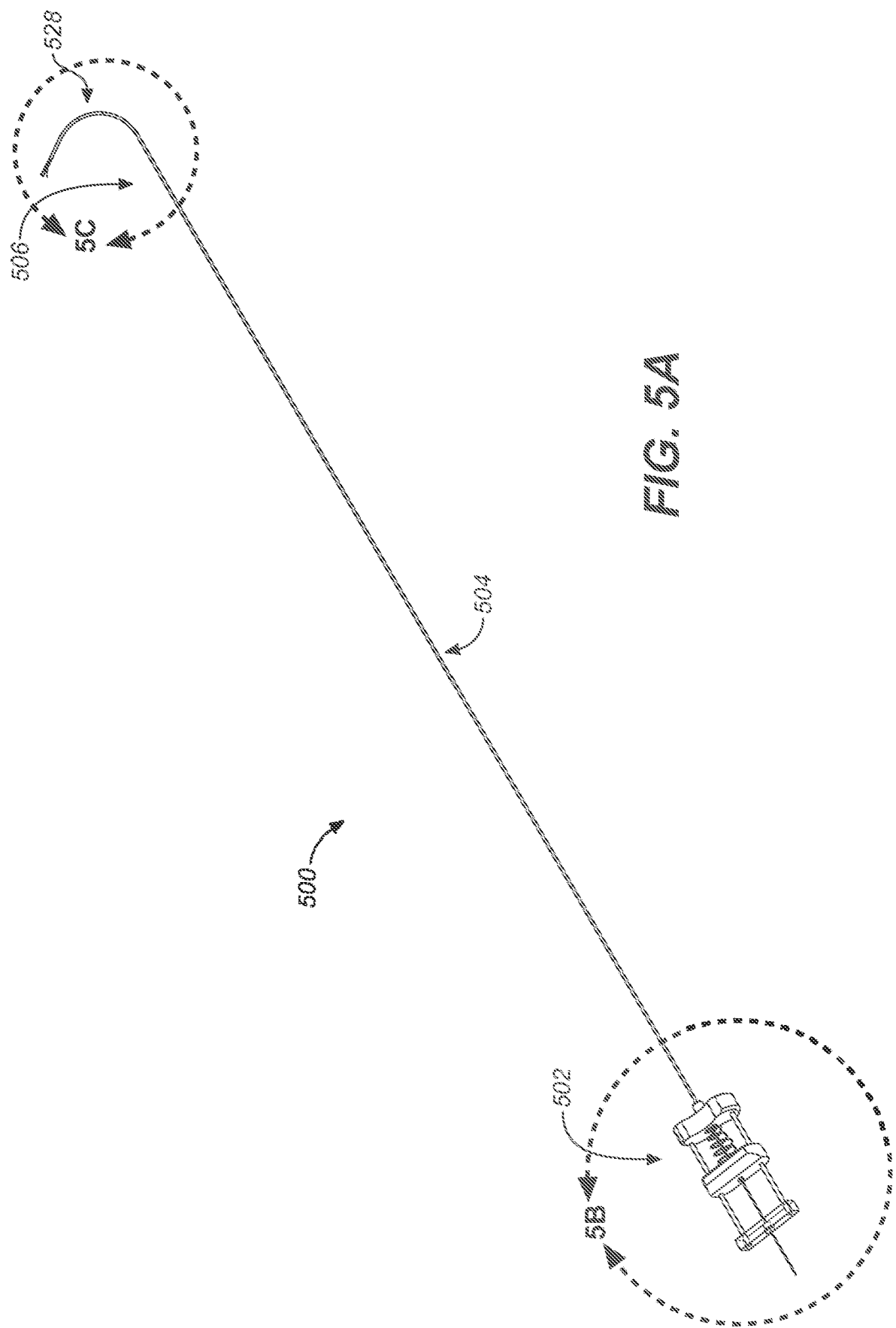

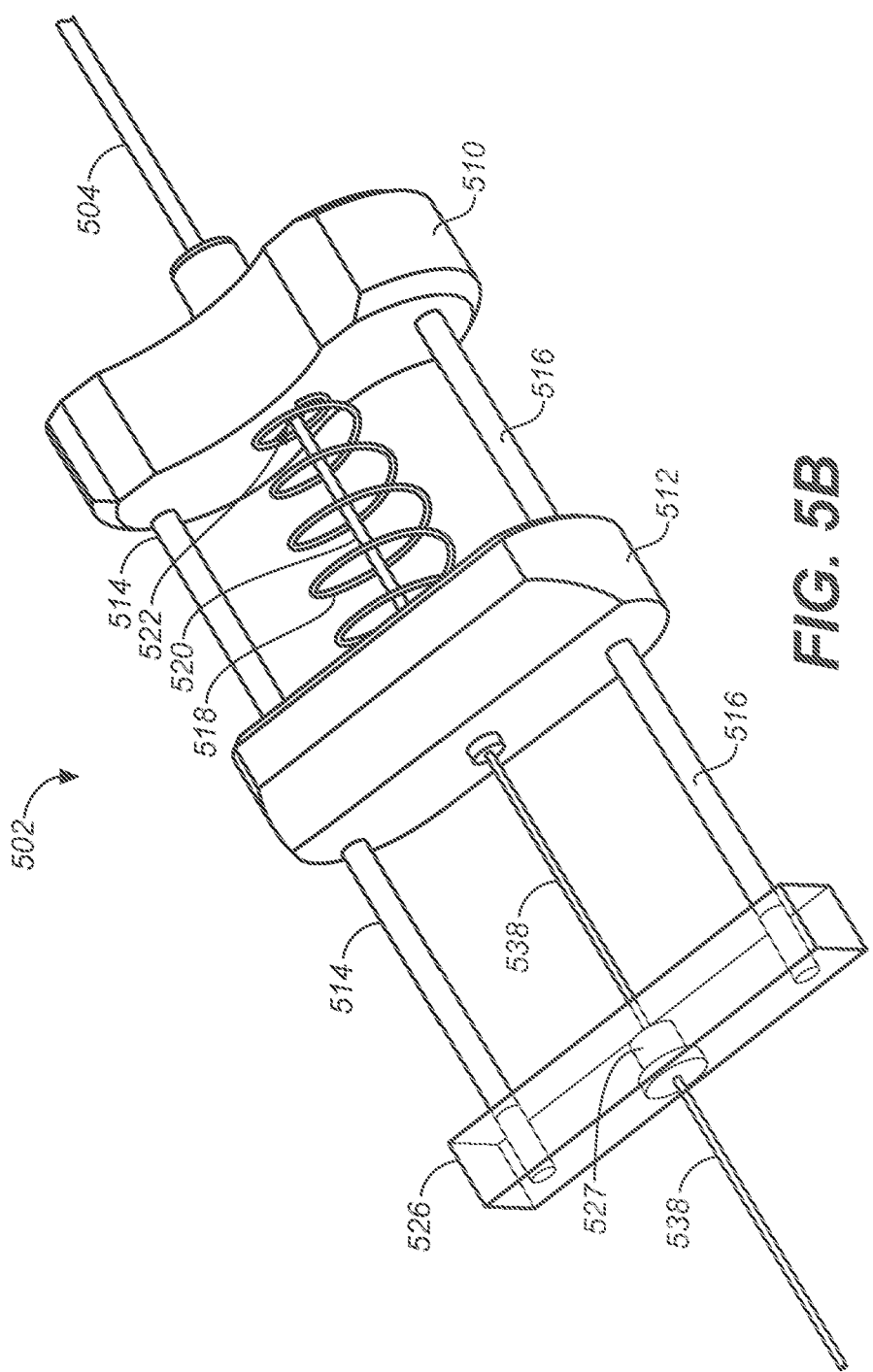

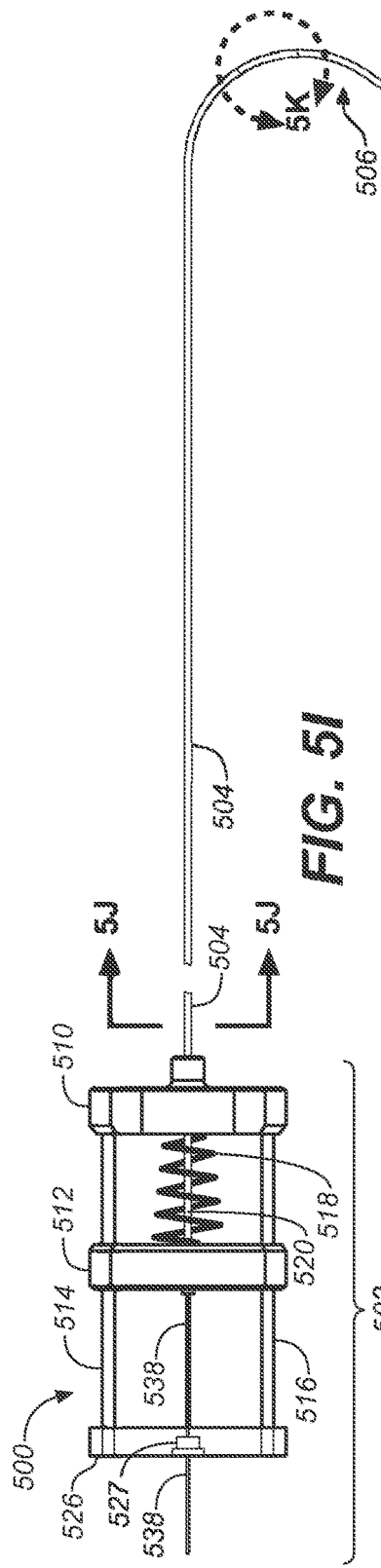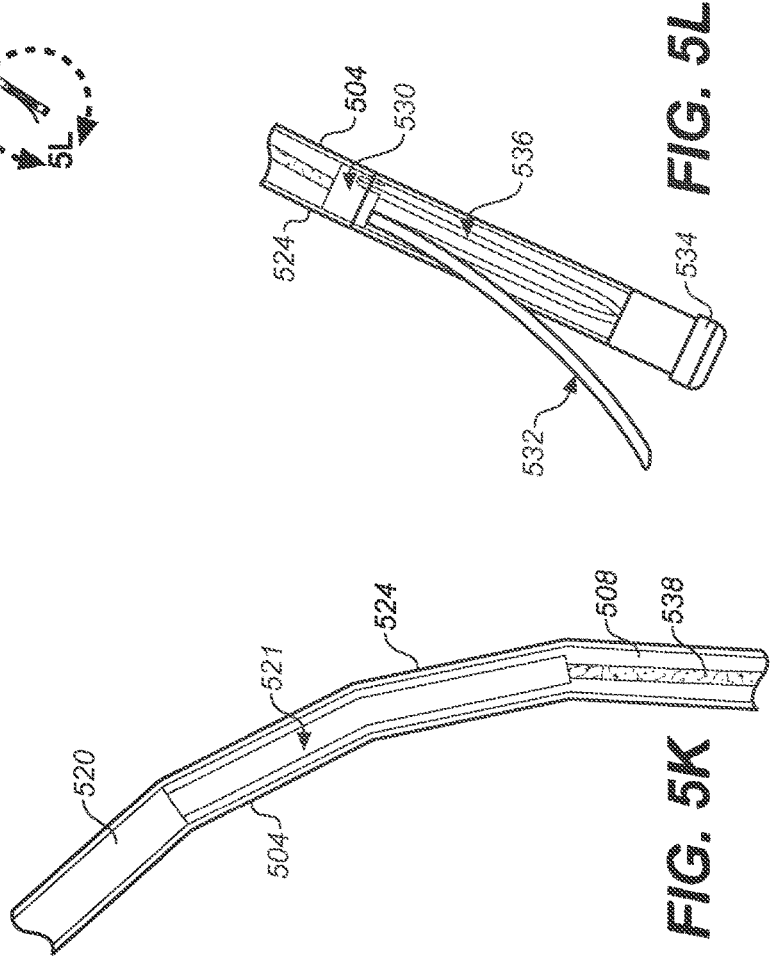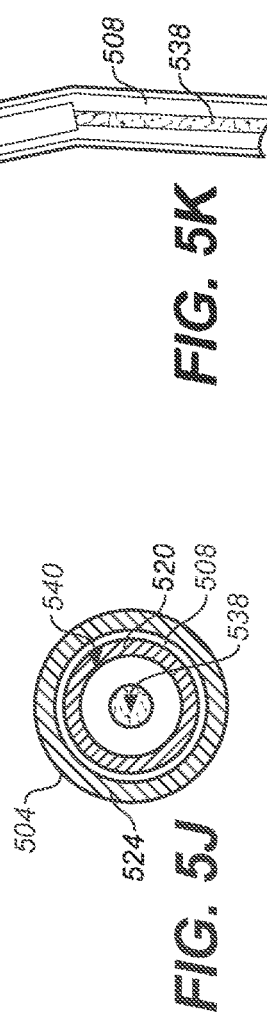

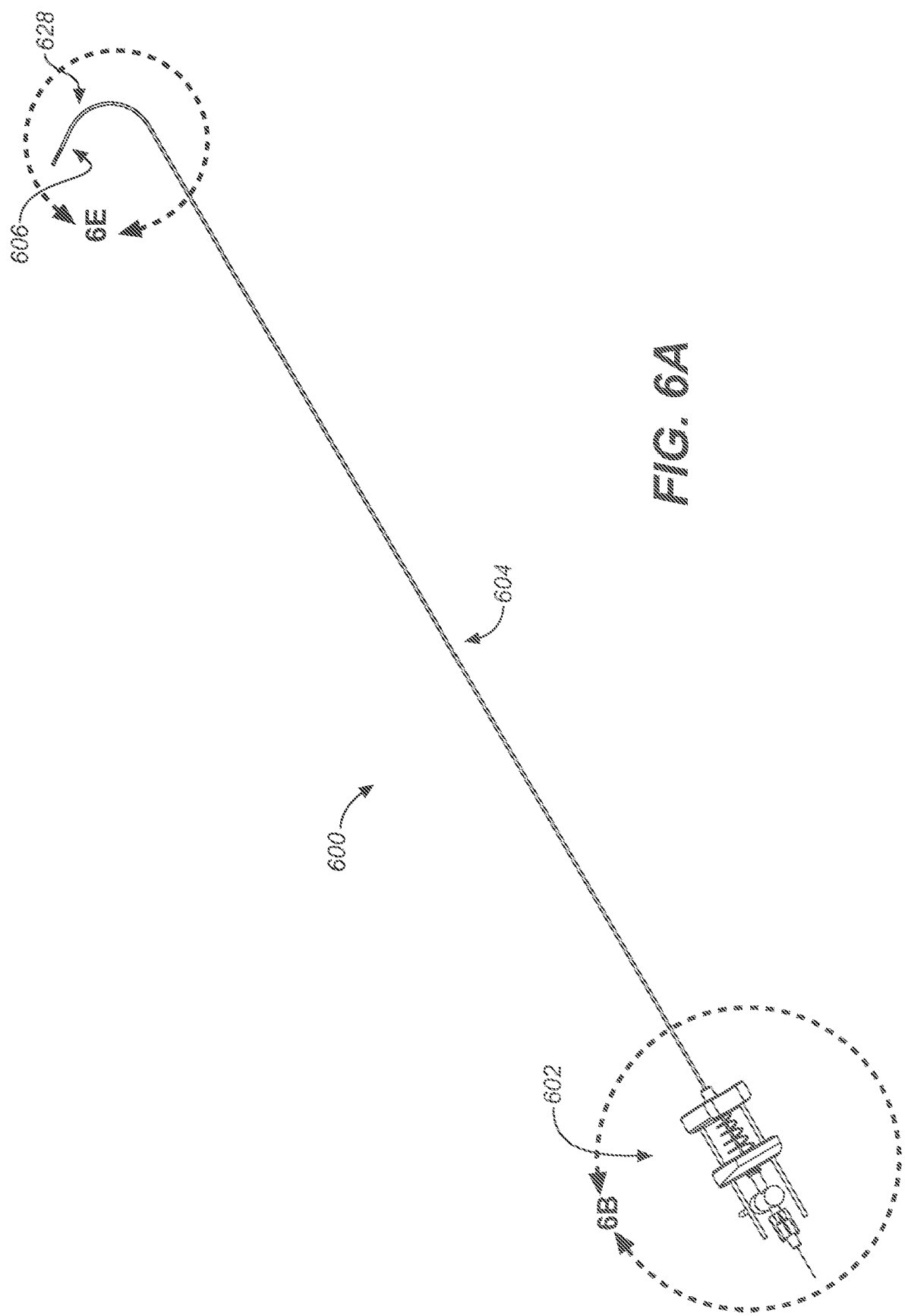

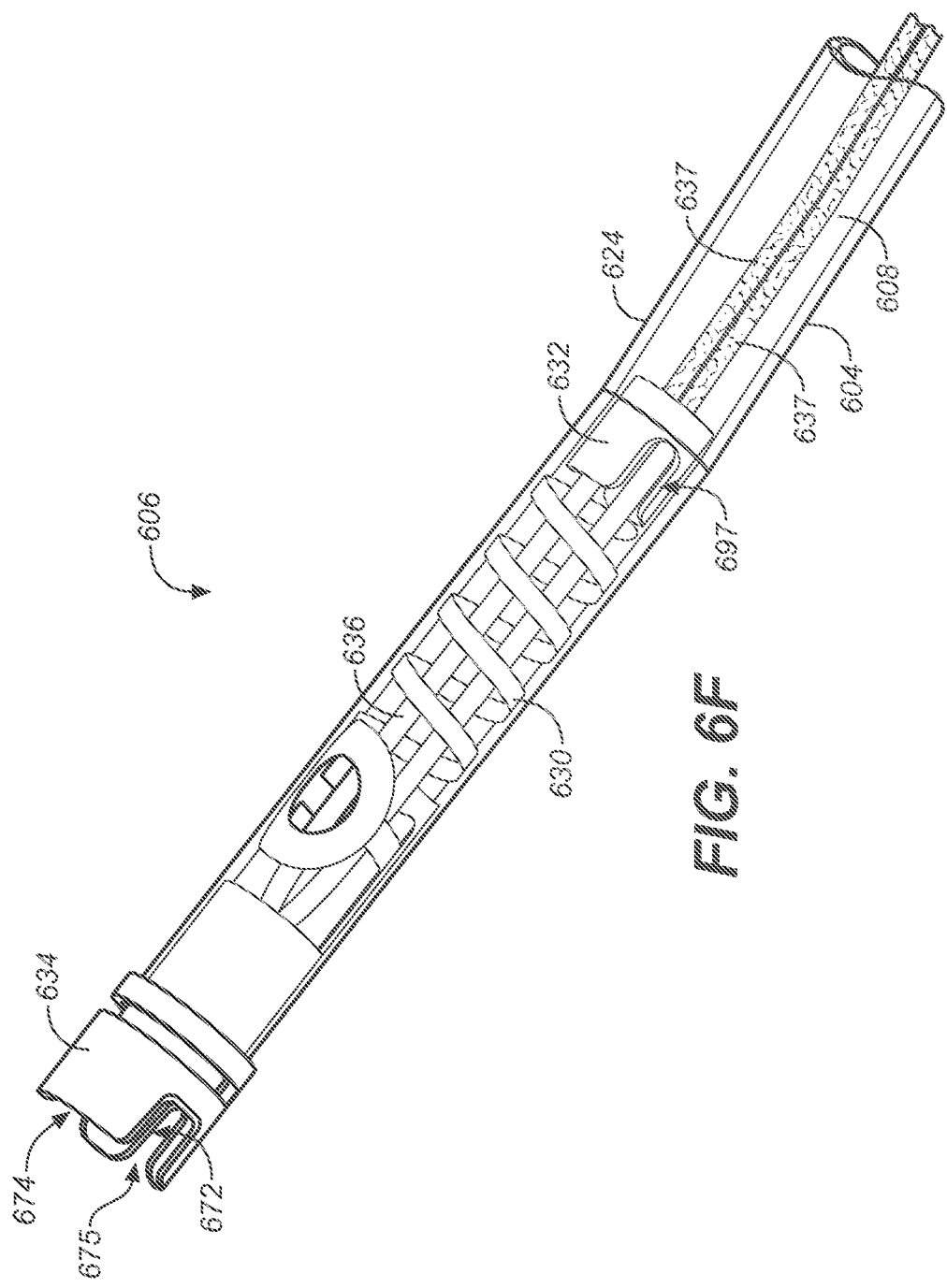

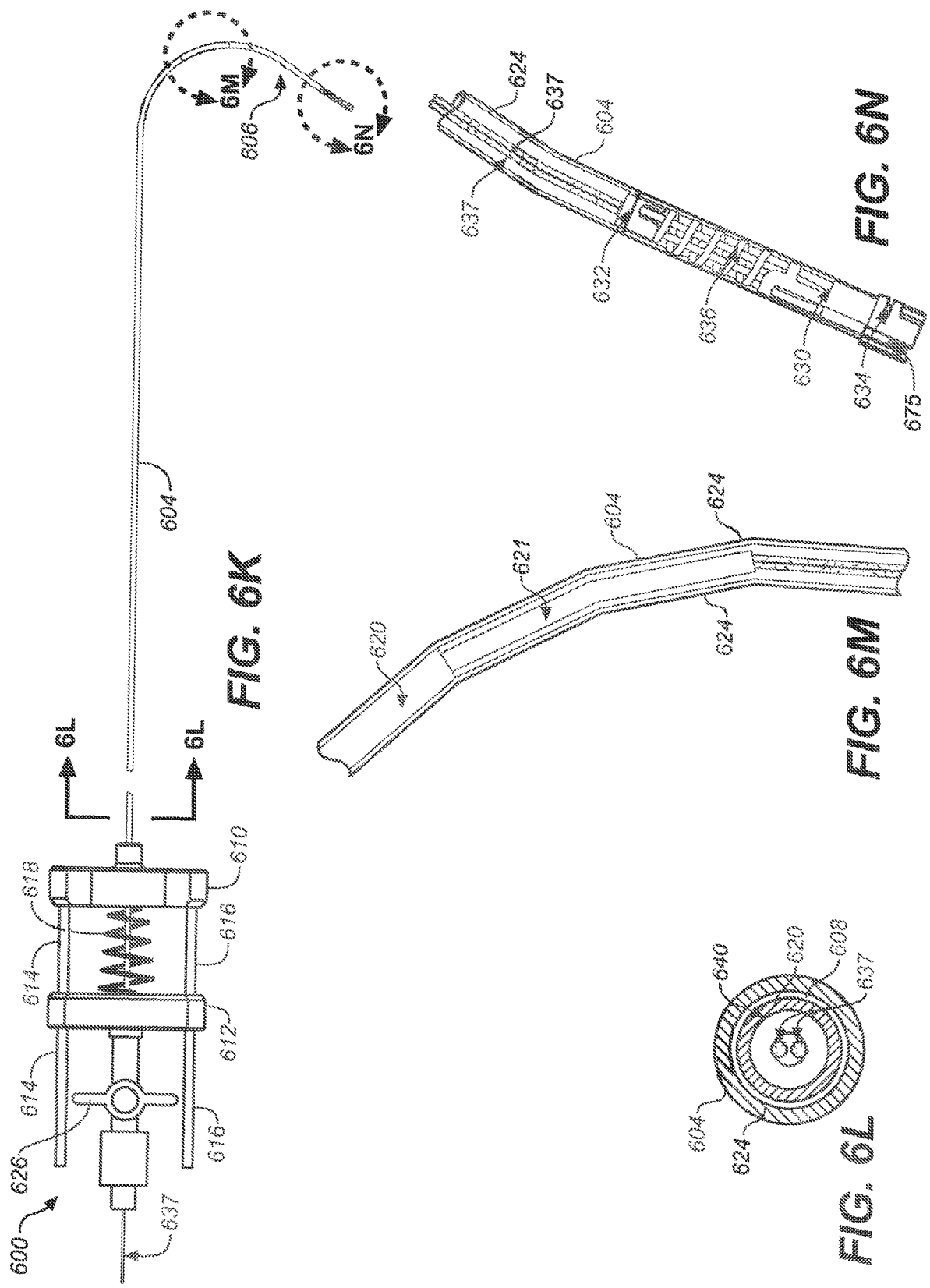

ANCHOR DEPLOYMENT DEVICES AND RELATED METHODS

CROSS-REFERENCE TO RELATED APPLICATIONS

This application is a continuation of U.S. application Ser. No. 14/052,593, filed on Oct. 11, 2013, now U.S. Pat. No. 9,616,197, which is a continuation application of U.S. application Ser. No. 12/657,422, filed on Jan. 19, 2010, now abandoned, which claims the benefit of U.S. Provisional Application No. 61/145,964, filed on Jan. 20, 2009, U.S. Provisional Application No. 61/160,230, filed on Mar. 13, 2009, U.S. Provisional Application No. 61/160,670, filed on Mar. 16, 2009, U.S. Provisional Application No. 61/178,910, filed on May 15, 2009, and U.S. Provisional Application No. 61/178,938, filed on May 15, 2009, the disclosures of all of which are incorporated herein by reference in their entirety.

TECHNICAL FIELD

The devices, methods, and kits described herein relate generally to the deployment of one or more implants into a body of a subject. More specifically, the devices, methods, and kits described herein relate to the deployment of one or more anchors into tissue of a subject, such as heart tissue.

BACKGROUND

Many different medical procedures involve the use of implants, such as anchors. Anchors may be used to modify tissue (e.g., by changing the configuration of the tissue), to fasten one piece of tissue to another, to fasten tissue to material, and the like. Anchors range in design from simple staples or T-bars, to more complex designs having hooks or barbs, to any of a number of other different types of designs. In some cases, anchors that are connected to each other by a tether may be implanted into tissue, and the tether may then be tensioned to tighten or compress the tissue (e.g., by bringing two pieces or sections of the tissue together). As an example, in some cases, a mitral valve that is experiencing mitral regurgitation may be repaired by deploying tethered anchors into tissue in the vicinity of the valve, and tensioning the tether. Tensioning the tether can provide a cinching effect that brings the anchors closer together, thereby reducing the circumference of the valve and alleviating the mitral regurgitation. Devices and methods for mitral valve repair are described, for example, in U.S. patent application Ser. No. 11/232,190 (published as US 2006/0190030 A1), Ser. No. 11/270,034 (published as US 2006/0122633 A1), and Ser. No. 11/583,627 (published as US 2008/0172035 A1), all of which are hereby incorporated by reference in their entirety.

It would be desirable to provide devices, methods, and kits for deploying implants (e.g., tissue anchors) for use in any of a variety of procedures, such as percutaneous procedures and/or surgical procedures. It would also be desirable to provide devices that are relatively easy to use and/or that allow for enhanced control over the deployment of implants. Similarly, it would be desirable to provide devices that are capable of reaching tissues that are not easily accessible.

SUMMARY

Described here are devices, methods, and kits for deploying one or more implants, such as one or more anchors, into a target site (e.g., heart tissue) of a subject. These devices, methods, and kits may be used in a variety of procedures, such as percutaneous procedures or surgical procedures. In some variations, the devices may comprise one or more stop elements which may be used to control the advancement of the devices during use, and/or which may be used to control the advancement of one or more components within the devices. As an example, an anchor deployment catheter may comprise one or more external stop elements that may be used to help control the advancement of the catheter through another device (e.g., another catheter). Alternatively or additionally, the anchor deployment catheter may comprise one or more internal stop elements (e.g., disposed within a lumen of the anchor deployment catheter). The internal stop elements may, for example, be used to control advancement of a pushing member within the lumen. For example, an internal stop element may be used to prevent a pushing member from being inadvertently pushed out of an anchor deployment catheter (e.g., when the pushing member is being used to deploy an anchor from the catheter). While internal and external stop elements are described herein with reference to anchor deployment catheters, they may be used with any other types of catheters or devices for which their use is appropriate.

Some variations of the devices described here may comprise a catheter comprising a tubular elongated member defining a proximal portion, a distal portion, and a lumen therethrough. The catheter may also comprise a first stop element comprising an elongated flap. A first portion of the first stop element may be disposed within the lumen of the tubular elongated member, and/or a second portion of the first stop element may extend through an opening in a wall portion of the tubular elongated member. The catheter may further comprise an anchor disposed within the lumen of the tubular elongated member. In some variations, the catheter may comprise a coupling member coupled to the anchor. In certain variations, the catheter may comprise a second stop element (e.g., a tubular member) disposed within the lumen of the tubular elongated member. The second stop element may be coupled to or integral with the first stop element, or may be separate from the first stop element. In certain variations, the catheter may further comprise a pushing member including a distal portion comprising a first region having a first cross-sectional diameter and a second region having a second cross-sectional diameter that is smaller than the first cross-sectional diameter. For example, the distal portion of the pushing member may be tapered.

Some variations of the devices described here may be anchor deployment devices comprising a catheter defining a lumen for housing an anchor therein, a pushing member at least partially disposed within the lumen, and a tubular stop element disposed within the lumen. The pushing member and the tubular stop element may be configured such that when the pushing member is advanced into the tubular stop element, the tubular stop element limits further distal advancement of the pushing member. The anchor deployment device may further comprise an anchor disposed within the lumen of the catheter. The anchor may, for example, be coupled to the tubular stop element. The pushing member may comprise a distal portion comprising a first region having a first cross-sectional diameter and a second region having a second cross-sectional diameter that is smaller than the first cross-sectional diameter. For example, the distal portion of the pushing member may be tapered. The anchor deployment device may comprise a second stop element that is coupled to or integral with the tubular stop element. The second stop element may extend through an opening in a wall portion of the catheter, and/or may be in the form of an elongated flap extending from the tubular stop element.

Certain variations of the devices described here may have shafts comprising one or more flexible materials. This may render the devices particularly useful in percutaneous procedures, for example. In such variations, the devices may, for example, have a relatively low profile, consistent with their manipulation through the vasculature. Any suitable flexible material or materials may be used. Non-limiting examples of materials which may be relatively flexible include polymers (e.g., nylon, polyethylene, polyetheretherketone (PEEK), polytetrafluoroethylene (PTFE), and copolymers such as polyether block amides and fluorinated ethylene propylene copolymer), polymer blends (e.g., nylon blends), metal alloys (e.g., nickel titanium alloys, stainless steel), and combinations thereof. In certain variations, a device may comprise one or more polymer blends with a supporting metal braid or coil.

Some variations of the devices described here may have shafts comprising one or more relatively rigid materials. This may render the devices particularly useful, for example, in open or surgical procedures, where access to the target site is achieved by incision. Non-limiting examples of materials which may be relatively rigid include metal alloys (e.g., stainless steel, nickel titanium alloys), polymers (e.g., polypropylene, high density polyethylene (HDPE)), polymer composites (e.g., carbon-filled nylon, carbon-filled polyetheretherketone), and combinations thereof.

As discussed above, certain variations of the devices described here are anchor deployment catheters. It should be understood, however, that one or more features of the anchor deployment catheters described here may be applied to other types of catheters, or even other types of devices, as appropriate. Some variations of the catheters described here are primary anchor deployment catheters configured to deploy an anchor that is fixedly coupled to a coupling member. In certain variations, a primary anchor deployment catheter may be used to deploy one or more anchors into a target site at the beginning of an anchor deployment procedure. Other variations of the catheters described here comprise secondary anchor deployment catheters configured to deploy one or more anchors over a coupling member so that the anchors are slidably coupled to the coupling member. In some variations, a primary anchor deployment catheter may be used to deploy an anchor that is fixedly coupled to a coupling member into a target site. As a result, the coupling member may be secured to the target site, and may thereby serve as a track for the advancement of one or more secondary anchor deployment catheters to the target site. The secondary anchor deployment catheters, in turn, may be used to deploy one or more anchors slidably over the coupling member. The coupling member may also be left at the target site at the completion of the anchor deployment procedure, to serve as an implant itself.

The devices described here may also comprise a shaft having at least one preformed curve. For example, the shaft may have one or more curves near its distal tip. This may help the devices to access areas that would otherwise be difficult to reach. A curve may form an arc having any suitable central angle. For example, a curve may form an arc having a central angle ranging from about 15 degrees to about 270 degrees (e.g., from about 45 degrees to about 180 degrees, from about 50 degrees to about 120 degrees). Alternatively or additionally, a curve may form an arc having an arc diameter of about 5 degrees to about 90 degrees (e.g., from about 10 degrees to about 70 degrees, from about 20 degrees to about 50 degrees).

In some variations, a device may comprise a shaft having at least one curve, and the region of the shaft that is distal to the curve may be planar relative to at least one other region of the shaft that is proximal to the curve, or even relative to the rest of the shaft. In other words, the more distal region may define the same plane as the more proximal region or as the rest of the shaft. Alternatively or additionally, a device may comprise a shaft having a curve, where a region of the shaft that is distal to the curve defines a plane that is different from a plane defined by at least one other region of the shaft that is proximal to the curve (e.g., the rest of the shaft). For example, a catheter may comprise a shaft having a substantially straight proximal region defining a first plane, a curve distal to the substantially straight proximal region, and a region distal to the curve defining a second plane that is different from the first plane. A shaft of a device may have any appropriate number of curves and planes, depending, for example, on the anatomy of the target site. Moreover, in some cases, a shaft of a device may not have any curves.

The first and second planes defined by two different regions of a shaft of a device may, for example have an angle of about 10 degrees to about 90 degrees (e.g., about 20 degrees to about 80 degrees, about 30 degrees to about 75 degrees, about 40 degrees to about 70 degrees, or about 50 degrees to about 60 degrees, such as about 50 degrees or about 60 degrees) therebetween. As an example, in some variations a primary anchor deployment catheter may comprise a shaft having a first region defining a first plane and a second region defining a second plane, where the angle between the first and second planes is about 60 degrees. As another example, in certain variations a secondary anchor deployment catheter may comprise a shaft having a first region defining a first plane and a second region defining a second plane, where the angle between the first and second planes is about 50 degrees. The angle between any two planes defined by different regions of a device shaft may be selected, for example, based on the anatomical characteristics of the target site, and/or based on other devices to be used in conjunction with the device.

In some variations, a device may comprise a shaft having multiple different regions with curves between the different regions. At least two of the regions may define the same plane, and/or at least two of the regions may define different planes.

As used herein, values and ranges provided for an angle between two planes may refer to the smaller angle between the two planes. For example, if two planes intersect to define two 30-degree angles and two 150-degree angles, then the smaller angle would be one of the 30-degree angles. Alternatively or additionally, in some variations in which a shaft comprises a first region defining a first plane, a second region defining a second plane, and a third region defining a third plane, values and ranges provided herein for an angle between two of the planes may refer to an angle located within a space defined by the three planes. In certain variations, values and ranges provided herein for an angle between two of the planes may refer to an angle located outside of a space defined by the three planes.

In some variations, the devices described here may comprise a shaft having at least one inflection point, either in addition to, or as an alternative to, having at least one preformed curve. The inflection point may, for example, be located in a distal portion of the shaft. The curves and inflection points in a catheter may be designed to help position the catheter at a desired target site, and/or to help the catheter serve a particular function (e.g., deployment of anchors into heart valve annular tissue).

In certain variations, the devices may comprise at least two shafts. This may, for example, allow the devices to deploy multiple anchors simultaneously. Similarly, a single shaft of a device comprising at least one shaft may be configured to receive at least two anchors therein, for deploying multiple anchors serially or sequentially. The devices may have any suitable mechanism for deploying the anchors from the distal end of the shaft. For example, the mechanism may be a hydraulic mechanism, or a pressurized air mechanism. In some variations, the mechanism may comprise a pushing member slidably disposed within at least a portion of a lumen in the shaft. In some such variations, the device may comprise an actuator for actuating the pushing member.

Certain variations of the methods described here may comprise advancing a first catheter through a lumen of a second catheter, and advancing a portion of the first catheter through an opening in a wall portion or at a distal end of the second catheter. The portion of the first catheter may be advanced through the opening until the wall portion of the second catheter is positioned (e.g., wedged) between a wall portion and a stop element of the first catheter. The positioning of the wall portion of the second catheter between the wall portion and stop element of the first catheter may prevent further advancement of the first catheter through the opening in the wall portion or at the distal end of the second catheter.

The stop element of the first catheter may remain within the lumen of the second catheter while the portion of the first catheter is advanced through the opening in the wall portion or at the distal end of the second catheter. Advancing the portion of the first catheter through the opening may comprise pushing the portion of the first catheter through the opening with a pushing member. Some variations of methods may comprise deploying an anchor from the first catheter after the first catheter has been advanced through the opening in the wall portion or at the distal end of the second catheter. In certain variations, the anchor may be retrieved after it has been deployed. In some variations, the portion of the first catheter may be withdrawn back into the lumen of the second catheter after the anchor has been deployed from the first catheter. The stop element may comprise an elongated flap. In certain variations, the elongated flap may extend through an opening in the wall portion of the first catheter. In some variations, the elongated flap may curve away from the wall portion of the first catheter as the wall portion of the second catheter becomes positioned between the wall portion and stop element of the first catheter.

In certain variations, a method for deploying an anchor into tissue of a subject may comprise advancing a distal portion of a pushing member into a tubular stop element disposed within a lumen of a first catheter, Where the tubular stop element is coupled to an anchor. The method may also comprise advancing the distal portion of the pushing member against the anchor to deploy the anchor from the lumen of the first catheter and into tissue of a subject. The distal portion of the pushing member and the tubular stop element may be configured to limit further distal advancement of the pushing member once the distal portion of the pushing member has been advanced into the tubular stop element. In some variations, the method may comprise using the pushing member to decouple the anchor from the tubular stop element. In certain variations, the distal portion of the pushing member may comprise a first region having a first cross-sectional diameter and a second region having a second cross-sectional diameter that is smaller than the first cross-sectional diameter. For example, the distal portion of the pushing member may be tapered. In some variations, the method may comprise advancing the first catheter through an opening in a wall portion or at a distal end of a second catheter. The tubular stop element may be coupled to or integral with a second stop element that extends through an opening in a wall portion of the first catheter. The advancement of the first catheter through the opening in the wall portion or at a distal end of the second catheter may stop when the wall portion of the second catheter becomes positioned between (e.g., wedged between) the second stop element and a wall portion of the first catheter. In certain variations, the second stop element may comprise an elongated flap extending from the tubular stop element.

Some variations of the methods described here may comprise passing a coupling member through an eyelet of an anchor, loading the coupling member and anchor into a lumen of a shaft, and deploying the anchor. Some variations of the methods described here may comprise loading an anchor within a lumen of a shaft and deploying the anchor distally from the lumen. In certain variations in which the anchor comprises an eyelet, the inner diameter of the lumen of the shaft may be the same size as, or smaller than, the diameter of the eyelet of the anchor when the anchor is in an expanded configuration. Alternatively, the inner diameter of a lumen of the shaft may be larger than the diameter of the eyelet of the anchor when the anchor is in an expanded configuration. Certain methods described here may also comprise retrieving the anchor (e.g., in the event of misplacement).

Also described here are kits for the deployment of tissue anchors. In general, the kits may comprise one or more anchor deployment devices, such as one or more anchor deployment catheters. For example, a kit may comprise a primary anchor deployment catheter and one or more secondary anchor deployment catheters. The kits may further comprise one or more guide catheters, guide tunnels, and/or termination devices, such as locking catheters and/or cutting catheters. In some variations, the kits may comprise instructions on using the kit. The components of the kit may be packaged together, or two or more of the components may be packaged separately from each other.

BRIEF DESCRIPTION OF THE DRAWINGS

FIG. 5A is a perspective view of a variation of an anchor deployment device;

FIG. 5B is an enlarged view of region 5B of FIG. 5A; FIGS. 5H and 5I are side views of the anchor deployment device of FIG. 5A; FIG. 5J is a cross-sectional view of the anchor deployment device as shown in FIG. 5I, taken along line 5J-5J; FIG. 5K is an enlarged view of region 5K of FIG. 5I; and FIG. 5L is an enlarged view of region 5L of FIG. 5I.

FIG. 6A is a perspective view of another variation of an anchor deployment device; FIG. 6F is an enlarged view of region 6F of FIG. 6E; FIGS. 6J and 6K are side views of the anchor deployment device of FIG. 6A; FIG. 6L is a cross-sectional view of the anchor deployment device as shown in FIG. 6K, taken along line 6L-6L; FIG. 6M is an enlarged view of region 6M of FIG. 6K; and FIG. 6N is an enlarged view of region 6N of FIG. 6K.

FIG. 6O depicts a tether routed through a portion of the anchor deployment device of FIG. 6A.

DETAILED DESCRIPTION

Described here are devices, methods, and kits for deploying one or more implants, such as one or more anchors, into tissue (e.g., heart tissue) of a subject. In some variations, multiple implants may be coupled to each other with a coupling member (e.g., a tether), which may be tensioned to tighten or compress tissue, such as soft tissue. Soft tissue includes, for example, muscle tissue and fat tissue, while hard tissue includes, for example, bone tissue. The devices, methods, and kits described here may be used in percutaneous procedures (where access to the anchor deployment site is achieved intravascularly), or in open surgical procedures (where access to the anchor deployment site is achieved via incision). While not so limited, the devices, methods, and kits described here may be used, for example, in the fields of general surgery, cardiology, urology, neurosurgery, gastroenterology, and the like. Exemplary procedures include repair of heart valves (e.g., mitral, tricuspid, aortic), repair or reduction of sphincters, closure of wounds, and reduction of the circumference of the gastroesophageal junction. Some variations of the devices, methods, and/or kits described here may be used in endoscopic procedures (e.g., laparoscopy and/or arthroscopy). Certain variations of the devices, methods, and/or kits described here may be used in Natural Orifice Transluminal Endoscopic Surgery ("NOTES") procedures. In general, the devices, methods, and kits may be used with any of a variety of different anchors. For example, the devices may be used with anchors of any desirable size, the size of the anchor being largely dependent upon the procedure to be carried out. Specific examples of the devices, methods, and kits will now be described in further detail below.

Figure 1A:
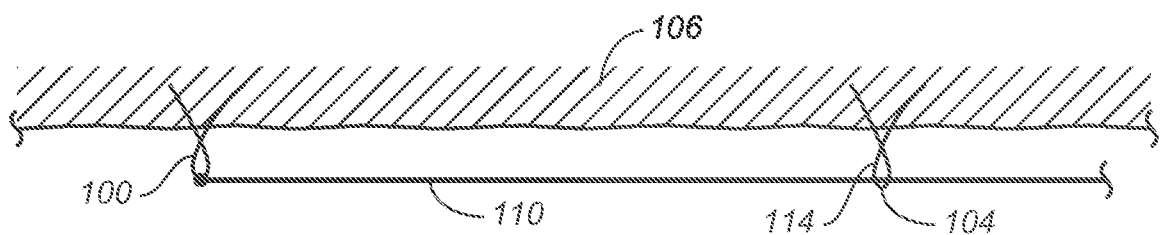
FIGS. 1A and 1B illustrate the tightening or compression of tissue of a subject using a tether.
Figure 1B:
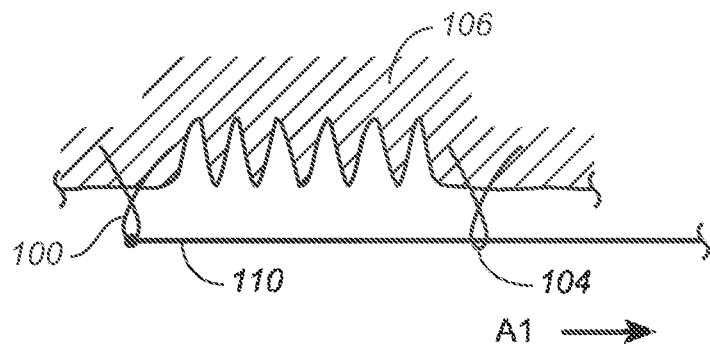

Turning now to the figures, FIG. 1A shows two anchors (100) and (104) anchored into tissue (106) of a subject. A coupling member (as shown, a tether (110)) is fixedly attached to anchor (100), and is threaded through a loop region (114) of anchor (104). As shown in FIG. 1B, when tether (110) is pulled upon in the direction of arrow (A1), a cinching effect results, such that anchors (100) and (104) are brought closer together, and the tissue length between anchors (100) and (104) is reduced. In this way, tissue (106) is compressed between anchors (100) and (104). It should be understood that while two anchors are shown in FIGS. 1A and 1B, in some cases multiple anchors may be used. After tether (110) has been tensioned by a desired amount, tether (110) may be locked to maintain the tension, and in some cases, excess portions of tether (110) may be cut and removed.

As discussed above, in some variations, one or more of the devices, methods, and/or kits described here may be used to deploy one or more anchors to tissue in the vicinity of a heart valve during a heart valve repair procedure (e.g., a mitral valve repair procedure). Heart valve repair procedures will now be discussed in further detail below.

Figure 2A:
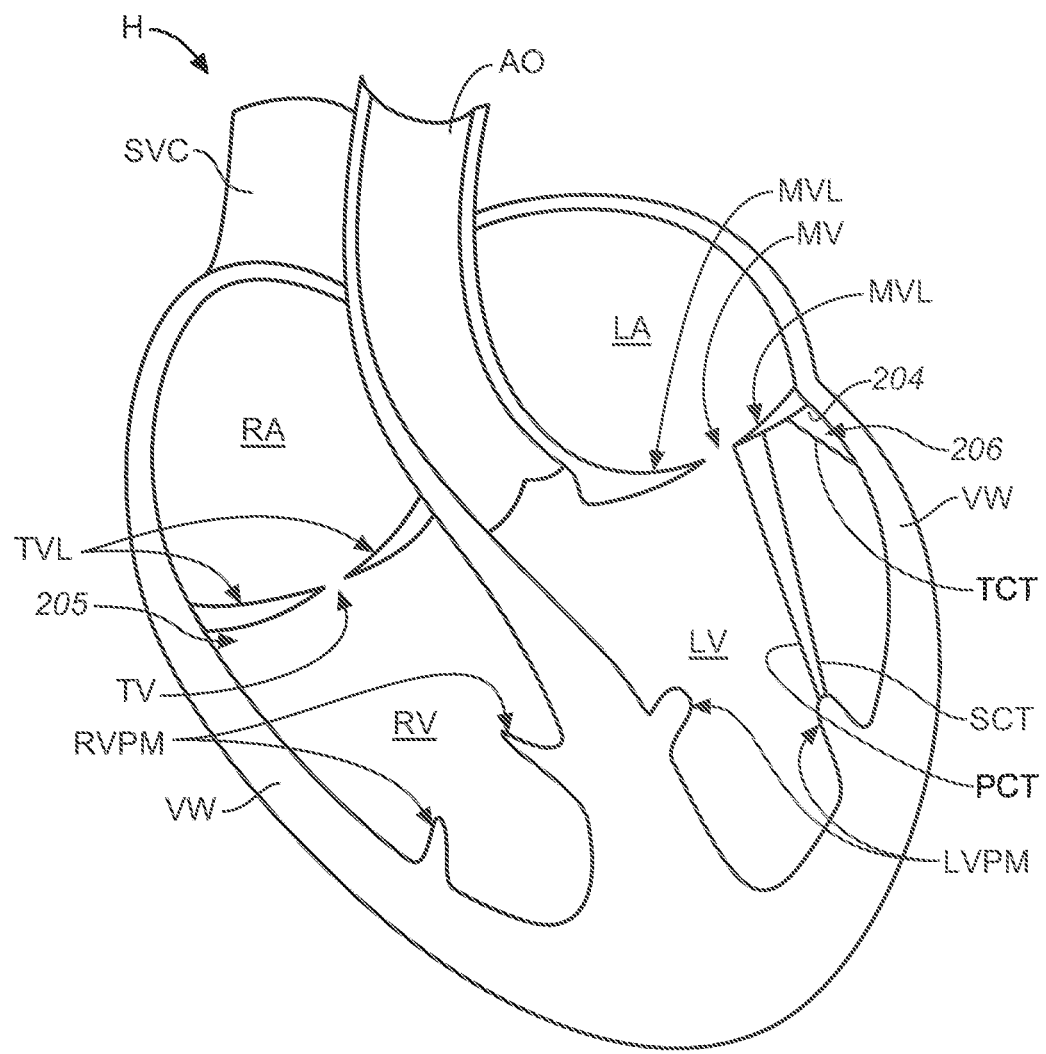
FIG. 2A is an illustrative depiction of a cross-sectional view of a heart.

FIG. 2A shows a cross-sectional view of a heart (H) including an aorta (AO), a superior vena cava (SVC), a right atrium (RA), a right ventricle (RV), a left atrium (LA), and a left ventricle (LV). As shown in FIG. 2A, a mitral valve (MV) comprising mitral valve leaflets (MVL) separates left atrium (LA) from left ventricle (LV), while a tricuspid valve (TV) comprising tricuspid valve leaflets (TVL) separates right atrium (RA) from right ventricle (RV). There are two mitral valve leaflets (MVL), the anteromedial leaflet and the posterolateral leaflet. In some cases, mitral valve leaflets (MVL) and/or tricuspid valve leaflets (TVL) may be referred to more generally herein as leaflets (L). Additionally, heart (H) includes papillary muscles in its right ventricle (RVPM), as well as papillary muscles in its left ventricle (LVPM). Both the mitral valve and the tricuspid valve comprise a valve annulus (not shown), discussed in further detail below.

FIG. 2A also shows a primary chorda tendinea (PCT), secondary chorda tendinea (SCT), and tertiary chorda tendinea (TCT) in left ventricle (LV)—of course, these are only illustrative chordae tendineae, and a heart generally has more than one of each of these different types of chordae tendineae. The chordae tendineae (also referred to herein as "chords") are tendons in the left and right ventricles of the heart, some of which connect the heart's papillary muscles to its mitral and tricuspid valves. These chords help to ensure unidirectional flow through the valve leaflets, preventing the valves from moving into the atria when the ventricles contract. Primary or first-order chords attach papillary muscles to the free edges of the valve leaflets, secondary or second-order chords attach papillary muscles to the ventricular surfaces of the valve leaflets, and tertiary or third-order chords connect the ventricular walls to the undersurfaces of the posterolateral leaflets.

As shown in FIG. 2A, right ventricle (RV) includes a subvalvular space (205), and left ventricle (LV) includes a subvalvular space (206). The subvalvular space, as used herein, generally includes the portion of the ventricular chamber that is bound peripherally by the ventricular wall (VW), superiorly by the atrio-ventricular valve leaflets, and centrally by the primary chordae tendineae (PCT), and is located along the circumference of the valve annulus. Additionally, the subannular groove region (204), as used herein, includes the space bordered by the inner surface of the ventricular wall (VW), the inferior surface of valve leaflets (MVL) or (TVL), and the tertiary chordae tendineae (TCT) connected directly to the ventricular wall (VW) and a leaflet (L). While FIG. 2A shows subannular groove region (204) in left ventricle (LV), it should be understood that right ventricle (RV) has a corresponding subannular groove region, as well. Devices and methods described here with respect to the subannular groove region in the left ventricle may, of course, be used in the subannular groove region of the right ventricle, as appropriate.

Figure 2B:
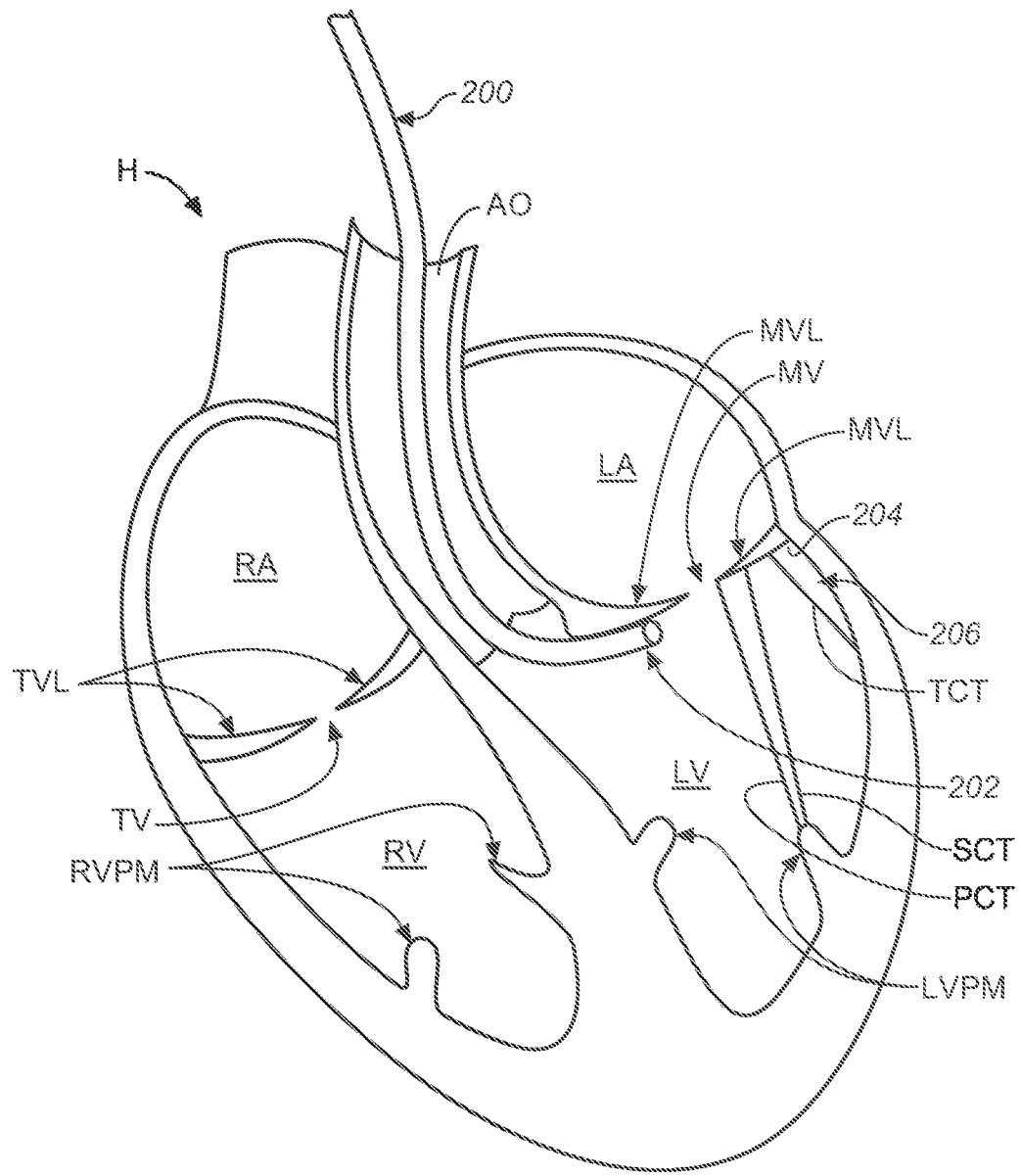
FIG. 2B is another illustrative depiction of a cross-sectional view of the heart of FIG. 2A, with a variation of a catheter advanced through the aorta and into the left ventricle.

FIG. 2B shows a cross-sectional depiction of heart (H) with one variation of a catheter (200) advanced in a retrograde direction through aorta (AO) and into left ventricle (LV) (e.g., after being inserted into the femoral artery). Catheter (200) may, for example, be a guide catheter; which will be discussed in further detail below, Retrograde, as used herein, generally refers to a direction opposite the expected flow of blood. This access route may be used to reach subvalvular space (206). The distal portion of catheter (200) may then be advanced, for example, under the posterolateral mitral valve leaflet and into subannular groove region (204). In some variations, catheter (200) may be a generally flexible elongate catheter which may have one or more curves or bends toward its distal end. The curves or bends may facilitate placement of the distal end (202) of catheter (200) at the desired location. Distal end (202) of catheter (200) may be configured to be positioned at an opening into subvalvular space (206) or within subvalvular space (206), such that subsequent devices (e.g., anchor deployment catheters) may be passed through catheter (200) and into subvalvular space (206). Although the retrograde aortic access route preferably starts from a percutaneous or peripheral access site, in some variations, aortic access may be achieved by an incision in the ascending aorta, descending aorta, aortic arch or iliac arteries, following surgical, thoracoscopic or laparoscopic access to a body cavity.

In certain variations, other spaces bound by or relating to one or more cardiac structures may be used as a target region of the heart. These structures include but are not limited to the base of the ventricle, the mitral valve, the tricuspid valve, the primary chordae tendineae, the secondary chordae tendineae, the tertiary chordae tendineae, the anterior mitral valve leaflet chordae tendineae, the posterior mitral valve leaflet chordae tendineae, the interleaflet chordae tendineae, the papillary muscle, the anterior-lateral papillary muscle, the posterior-medial papillary muscle, the ventricular apical region, and the ventricular apex. As an example, in some variations, a supra-apical space from about the base of the mitral valve leaflets to just above the ventricular apex or apical region may be the target region. As another example, in certain variations, the target region may be the peri-papillary muscle region, which includes the space about one centimeter above and about one centimeter below the level of the papillary muscle region, as well as the spaces between the papillary muscles. In some variations, the target region may be the endocardial surface abutting or accessible from the given space or cardiac structures. In still other variations, the target region may be a region located between the base and apex of a ventricle and between longitudinal borders drawn through the papillary muscles (e.g., either a posterior-lateral or an anterior-medial ventricular endocardial surface). In other variations, the target region may exclude the space along the longitudinal axis from the base of a ventricle to the apex of the ventricle (e.g., the target region may be tubular or toroidal in configuration, with an internal border relating to a chorda tendinea).

Figure 3:
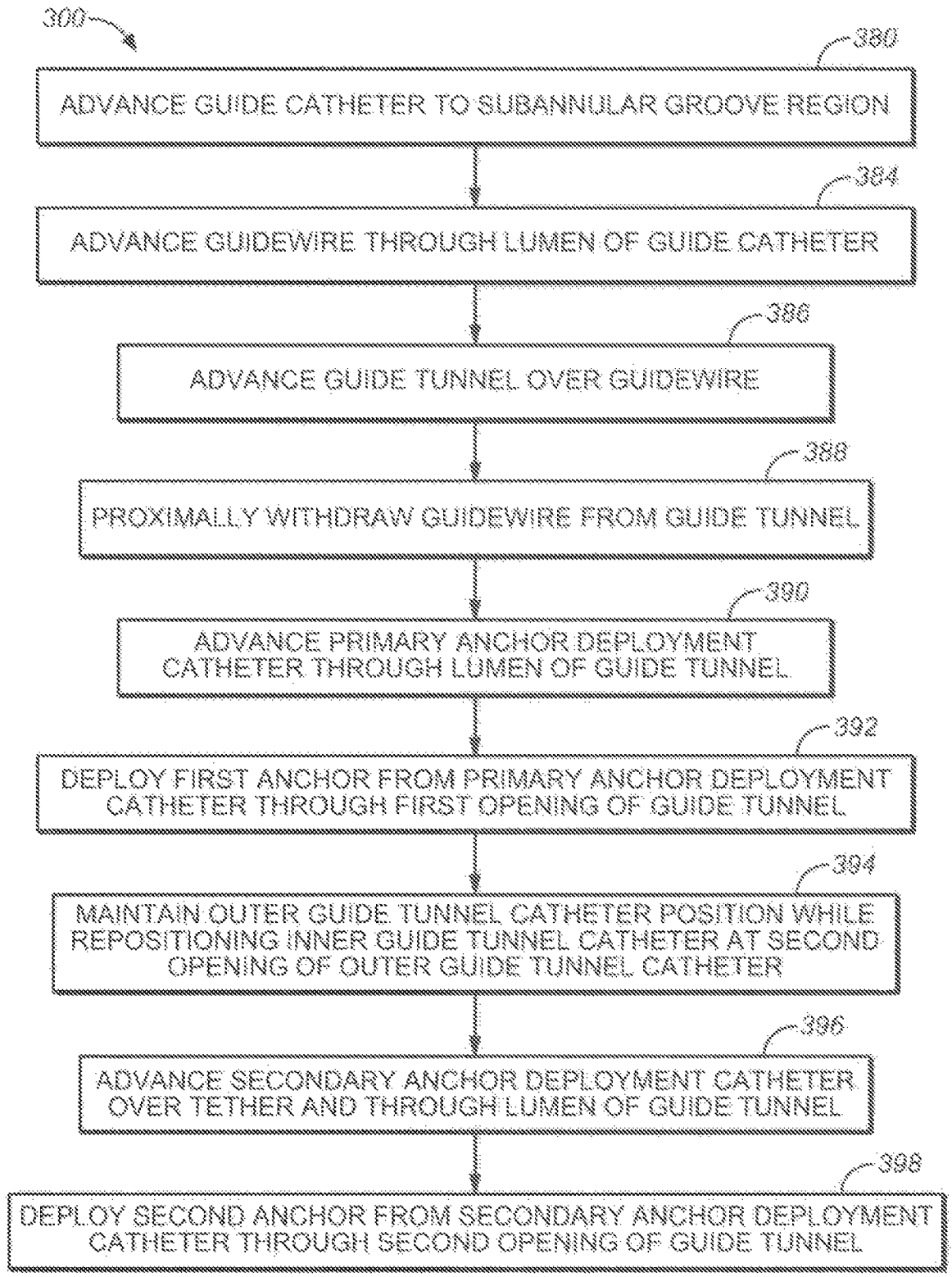
FIG. 3 is a flowchart representation of a variation of a method for deploying anchors into a subvalvular space of a heart.

FIG. 3 provides a flowchart depiction of one variation of a method (300) for deploying at least two anchors of an implant into the region of a heart valve annulus. As shown there, this illustrative method comprises advancing a guide catheter to a subannular groove region of a heart (380), advancing a guidewire through a lumen of the guide catheter (384), advancing a guide tunnel over the guidewire (386), and proximally withdrawing the guidewire from the guide tunnel (388). The guide catheter may be advanced into and positioned within the body under fluoroscopic guidance, for example. In some cases, the accessibility of the subannular groove region may be verified prior to advancement of the guide catheter to the subannular groove region using a diagnostic catheter). Devices, methods, and kits for verifying the accessibility of a target site are described, for example, in U.S. Provisional Application Ser. Nos. 61/145,964, filed on Jan. 20, 2009; 61/160,670, filed on Mar. 16, 2009; and 61/178,938, filed on May 15, 2009, all of which are hereby incorporated by reference in their entirety.

The guide tunnel may, for example, comprise an outer catheter with a passageway in which an inner catheter slidably resides. However, other appropriate variations of guide tunnels may also be used. After the guidewire has been proximally withdrawn from the guide tunnel (388), a primary anchor deployment catheter may be advanced through the lumen of the guide tunnel (390), and a first anchor may be deployed through a first opening of the guide tunnel and into a first region of the heart valve annular tissue (392). The first anchor is typically coupled or secured to a coupling member, such as a tether. In this way, after the first anchor is secured to heart tissue, the coupling member will remain coupled to the first anchor. While the coupling member may be used as a track or monorail for the advancement of additional anchor deployment catheters thereover, the coupling member is also a component of the implant that interconnects the multiple anchors. A portion of the coupling member facilitates the tightening of the implant and remains in the body with the anchors after the anchor deployment system is removed from the body.

After the first anchor has been deployed in the region of the heart valve annular tissue, the primary anchor deployment catheter may be proximally withdrawn from the guide tunnel. While maintaining the existing position of the outer catheter of the guide tunnel about the subannular groove region, the inner catheter of the guide tunnel may be repositioned at a second opening of the outer catheter (394). A secondary anchor deployment catheter may then be advanced over the coupling member through the lumen of the guide tunnel (396).

During advancement of the secondary anchor deployment catheter over the coupling member, the coupling member may enter the secondary anchor deployment catheter through an opening at its distal end, and exit the secondary anchor deployment catheter through an opening in its side wall that is proximal to its distal end. Alternatively, the coupling member may enter the secondary anchor deployment catheter through an opening at its distal end, and exit the secondary anchor deployment catheter through an opening at its proximal end, or at any other location proximal to the distal end. After the secondary anchor deployment catheter has been advanced over the coupling member through the lumen of the guide tunnel, a second anchor may be deployed from the secondary anchor deployment catheter into a second region of the heart valve annular tissue using a second opening of the guide tunnel (398). In some variations, the secondary anchor deployment catheter may be used to deploy one or more additional anchors, and/or one or more other anchor deployment catheters may be used to deploy one or more additional anchors.

While method (300) has been described above, other variations of methods may be employed, depending on the needs of the patient and operator preference. As an example, in some variations, after a first anchor has been deployed using the primary anchor deployment catheter, subsequent deployment of anchors may be achieved by removing and reloading the primary anchor deployment catheter (as an alternative to, or in addition to, using one or more secondary anchor deployment catheters). In other variations, the primary anchor deployment catheter may be loaded with a plurality of anchors and may not need to be withdrawn from the guide tunnel to deploy subsequent anchors. As another example, in certain variations, multiple (i.e., at least two) anchors may be deployed through a single window of a guide tunnel using primary and/or secondary anchor deployment catheters. For example, two or more anchors may be deployed through the first opening of a guide tunnel. In some variations, multiple anchors may be deployed through a distal-most opening in a guide tunnel, and multiple anchors may also be deployed through a proximal-most opening in the guide tunnel. This may, for example, result in enhanced stability for the overall implant. Other suitable variations of anchor deployment methods may also be used.

Figure 4A:
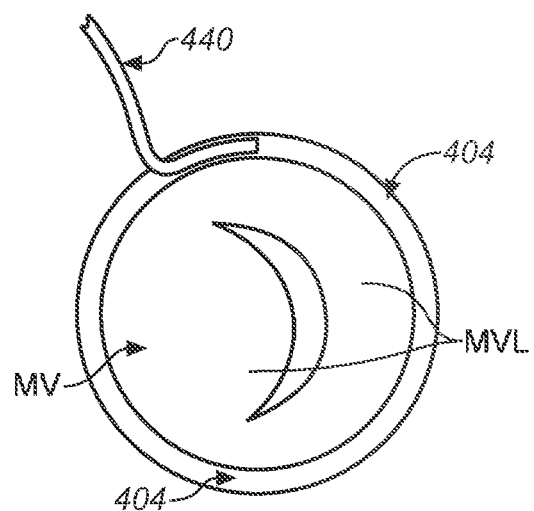
FIGS. 4A-4I schematically depict a variation of a method for deploying multiple tissue anchors into a subvalvular space of a heart.

FIGS. 4A-4I provide a more detailed depiction of the method shown in flowchart form in FIG. 3. As shown there, mitral valve (MV) is depicted schematically from an inferior perspective looking in a superior direction, but in other variations the tricuspid valve, pulmonary valve or aortic valve may be accessed. First, and as shown in FIG. 4A, a guide catheter (440) may be advanced to a subannular groove region (404) using any of the access routes (or any other suitable access routes) described herein. Guide catheter (440) may have a size of, for example, 6 Fr to 16 Fr (i.e., an outer diameter of 2 millimeters to 5.33 millimeters), such as 14 Fr (i.e., an outer diameter of 4.67 millimeters), although other suitable sizes may also be used. In some variations, guide catheter (440) may have an atraumatic tip (e.g., to limit the likelihood of damage to tissue during advancement of the guide catheter). Guide catheters are described, for example, in U.S. Provisional Application Ser. Nos. 61/145,964, filed on Jan. 20, 2009; 61/160,670, filed on Mar. 16, 2009, and 61/178,938, filed on May 15, 2009, each of which was previously incorporated by reference in its entirety.

Figure 4B:
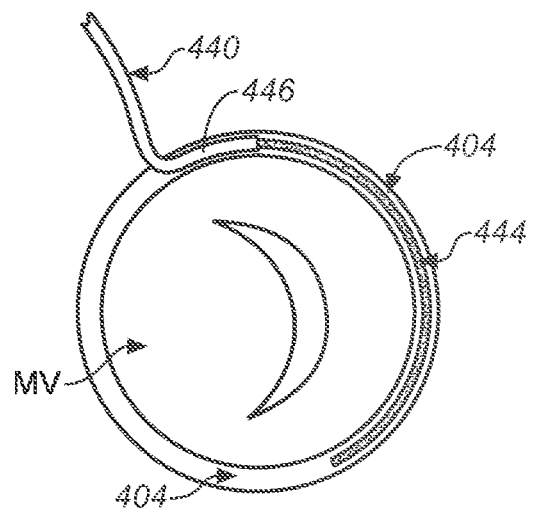

As shown in FIG. 4B, after guide catheter (440) has been positioned at the desired location in subannular groove region (404), a guidewire (444) may be advanced through a lumen of guide catheter (440). Guidewire (444) may be advanced beyond the distal end (446) of guide catheter (440), so that guidewire (444) extends farther along subannular groove region (404) than guide catheter (440), as shown in FIG. 4B.

Figure 4C:
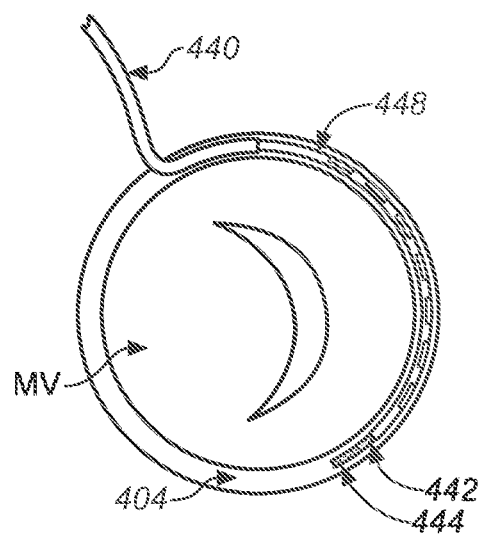

After guidewire (444) has been positioned in subannular groove region (404), a guide tunnel (448) may be advanced through guide catheter (440), over guidewire (444), as shown in FIG. 4C. Referring to FIG. 4C, a distal portion (442) of guidewire (444) extends from the distal end of guide tunnel (448). Guide tunnel (448) may be any suitable catheter, and in some instances, it may be desirable for the guide tunnel to be pre-shaped or pre-formed at its distal end, such as the guide tunnel illustrated in FIG. 4C. In certain variations, guide tunnel (448) may have a pre-shaped distal portion that is curved. In this way, the guide tunnel may more easily conform to the geometry of the atrio-ventricular valve. It should also be understood that any of the catheters or guidewires described here may be pre-shaped or pre-formed to include any number of suitable curves, angles or configurations. Of course, the guidewires and/or catheters described here may also be steerable. Guide tunnels are described, for example, in U.S. patent application Ser. No. 12/366,553 (published as US 2009/0222083 A1), which is hereby incorporated by reference in its entirety. Curved catheters are described, for example, in U.S. Provisional Application Ser. Nos. 61/145,964, filed on Jan. 20, 2009; 61/160,670, filed on Mar. 16, 2009; and 61/178,938, filed on May 15, 2009, each of which was previously incorporated by reference in its entirety.

Figure 4D:
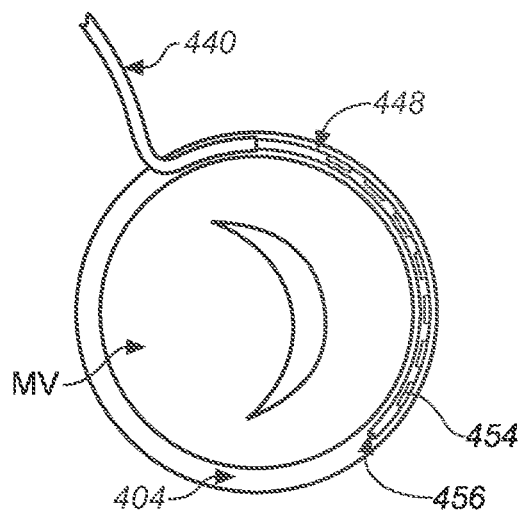

Referring now to FIG. 4D, after guide tunnel (448) has been positioned in subannular groove region (404), guidewire (444) may be withdrawn proximally. A primary anchor deployment catheter (not shown) may then be advanced through the lumen of guide tunnel (448) and toward an opening (454) at or adjacent to the distal tip (456) of guide tunnel (448).

Figure 4E:
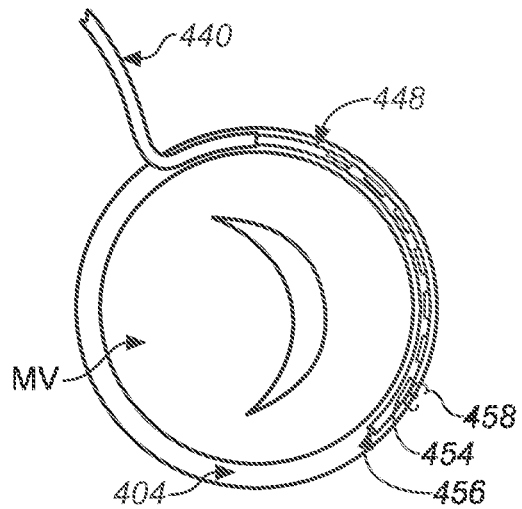

In the variation depicted in FIG. 4E, the primary anchor deployment catheter remains within guide tunnel (448), and an anchor (458) is deployed through opening (454) to attach to the body tissue. In other variations, however, the primary anchor deployment catheter may be extended through opening (454) of guide tunnel (448). While anchor deployment catheters are described herein, additional exemplary variations of anchor deployment catheters are described, for example, in U.S. patent application Ser. No. 11/583,627 (published as US 2008/0172035 A1), which is hereby incorporated by reference in its entirety, and in U.S. patent application Ser. No. 12/366,553 (published as US 2009/0222083 A1), which was previously incorporated by reference in its entirety.

In some variations, opening (454) may be the distal-most anchor deployment opening of guide tunnel (448). In certain variations, one or more openings may have a separate lumen in guide tunnel (448), so that any anchors deployed from such openings would not interfere with or restrict the deployment of subsequent tissue anchors distal to those openings. Furthermore, although FIG. 4F depicts opening (454) as a side opening of guide tunnel (448), in some variations, opening (454) may be located at distal tip (456) and may be the same opening shown with a distally protruding guidewire (444) in FIG. 4C.

Anchor (458), shown in FIG. 4E, is preferably a self-expanding design as it exits the anchor deployment catheter and guide tunnel (448) to self-secure into the annular tissue accessible from subannular groove region (404). It should be understood that one or more anchors of an implant may be deployed into the annulus directly, while other anchors may be secured to other tissue in the vicinity of subannular groove region (404). For example, one or more anchors may be secured to the tissue below the annulus. Anchor deployment may be monitored, for example, under fluoroscopy. After anchor (458) has been deployed, the primary anchor deployment catheter may be proximally withdrawn. Alternatively, in some variations, the primary anchor deployment catheter may be used to deploy one or more additional anchors through the same opening in the guide tunnel, prior to being proximally withdrawn. A tether (460), attached to anchor (458) and seen best in FIGS. 4G and 4H, may be used to facilitate the insertion of additional anchor deployment catheters toward the implantation site.

Figure 4F:
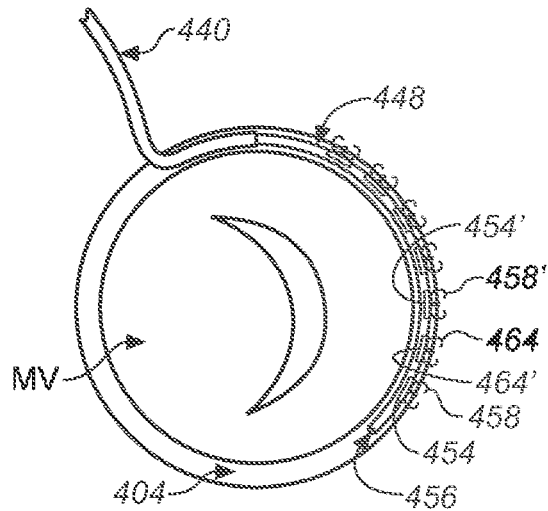
Figure 4G:
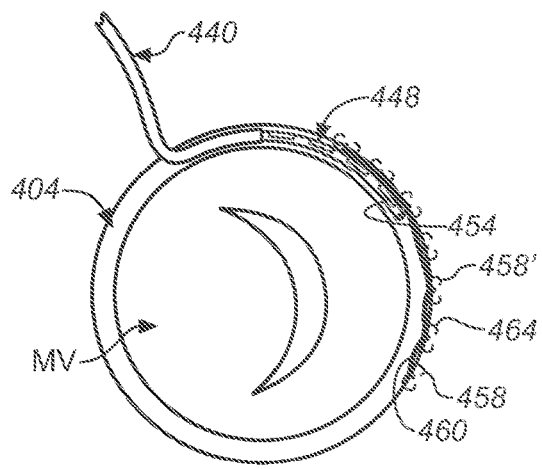

In this particular variation, as demonstrated in FIG. 4F, guide tunnel (448) is maintained in the same position while additional anchors (464) and (458') are deployed from additional openings (464') and (454') along guide tunnel (448). In some variations, one or more secondary anchor deployment catheters may be serially inserted into guide tunnel (448), using tether (460) to serially guide anchors (464) and (458') through openings (464') and (454'). While not shown here, in certain variations, multiple anchors may be deployed through a single opening in a guide tunnel (e.g., by multiple different anchor deployment catheters, or by a single anchor deployment catheter). For example, an anchor deployment catheter may be used to deploy an anchor through an opening in a guide tunnel. Then, the guide tunnel maybe moved to adjust the position of the opening relative to the anatomy. After the guide tunnel has been moved, another anchor may be deployed through the same opening in the guide tunnel, either by the same anchor deployment catheter, or by a different anchor deployment catheter. Thus, an opening in a guide tunnel may be used in the deployment of one anchor or multiple anchors, or in some cases, may not be used in the deployment of any anchors (e.g., when other openings in the guide tunnel are used instead).

In certain variations, the anchor deployment catheters may be loaded with one or more anchors at the point-of-use, while in other variations the anchor deployment catheters may be pre-loaded at the point-of-manufacture. In some variations, the anchor deployment catheters may be reloaded at the point-of-use, while in other variations, the anchor deployment catheters may be single-use devices that are discarded after anchor deployment. In certain variations, the anchor deployment catheters may be configured to hold two or more anchors (e.g., anchors (458), (458'), and (464)), and may be able to deploy multiple anchors without requiring withdrawal of the anchor deployment catheter between anchor deployments. In some variations, multi-anchor deployment catheters may be configured to deploy multiple anchors simultaneously through multiple openings of guide tunnel (448), and/or to deploy multiple anchors simultaneously through at least one individual opening of guide tunnel (448).

Anchors (e.g., anchors (458), (458') and (464)) may be deployed from the anchor deployment catheter and guide tunnel (448) in any suitable fashion, including but not limited to using a push-pull wire, a plunger or pushing member, or any other suitable actuation technique. Similarly, anchors may be coupled to tether (460) by any suitable coupling method. For example, one or more knots, welded regions, and/or adhesives may be used. In some variations, crimping and/or tying techniques may be employed. Alternate variations for anchor deployment and anchor couplings are described, for example, in U.S. patent application Ser. No. 11/583,627 (published as US 2008/0172035 A1), which is hereby incorporated by reference in its entirety.

In the variations depicted in FIGS. 4A-4I, before a secondary anchor deployment catheter is advanced through guide tunnel (448), tether (460) may be threaded into the secondary anchor deployment catheter and slidably engaged with a second anchor (464). In some variations, second anchor (464) may be preloaded into the secondary anchor deployment catheter before threading tether (460), while in other variations, the second anchor may be pre-threaded before being loaded into the secondary anchor deployment catheter. Any of a number of different methods may be used to thread a coupling member, such as tether (460), into an anchor deployment catheter, and to engage the coupling member with an anchor. Exemplary methods are described, for example, in U.S. patent application Ser. No. 11/202,474 (published as US 2005/0273138 A1), which is hereby incorporated by reference in its entirety. Additionally, threading devices are described, for example, in U.S. patent application Ser. No. 11/232,190 (published as US 2006/0190030 A1), which was previously incorporated by reference in its entirety.

Figure 4I:
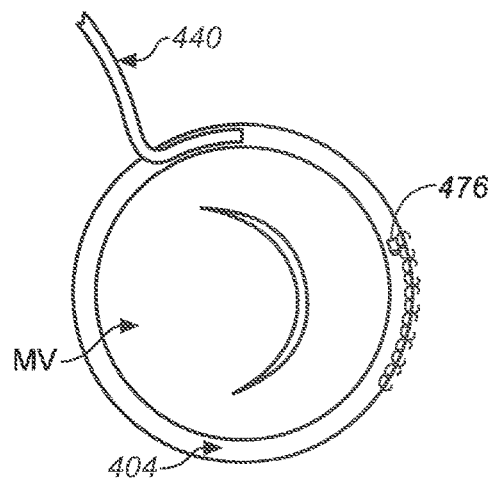
Figure 4H:
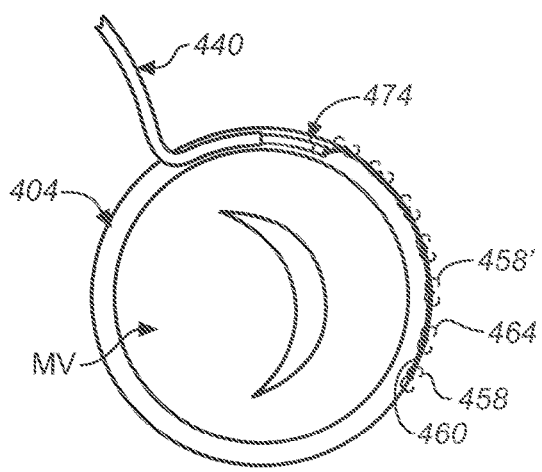

With reference to FIG. 4H, after all of anchors (458), (458') and (464) have been deployed into body tissue, guide tunnel (448) may be withdrawn from guide catheter (440). A termination catheter (474) may then be inserted through guide catheter (440), over tether (460). Termination catheter (474) may be used to facilitate tensioning of tether (460), thereby cinching anchors (458), (458') and (464) together to remodel the annular tissue. This cinching effect may be viewed, for example, using ultrasound. Termination catheter (474) may also be used to secure the cinched anchors (458), (458') and (464) with a termination member (476) that resists tether loosening or slippage, as illustrated in FIG. 4I. In other variations, termination catheter (474) may secure tether (460) to an anchor or to body tissue without the use of a termination member. Devices and methods for performing termination of cinchable implants are described, for example, in U.S. patent application Ser. No. 11/232,190 (published as US 2006/0190030 A1) and Ser. No. 11/270,034 (published as US 2006/0122633 A1), both of which were previously incorporated by reference in their entirety, and in U.S. patent application Ser. No. 12/253,885, filed on Oct. 17, 2008, and Ser. No. 12/480,568, filed on Jun. 8, 2009, both of which are hereby incorporated by reference in their entirety.

While one variation of a heart valve repair procedure has been described, other variations of heart valve repair procedures may also be used. Mitral valve repair procedures are described, for example, in U.S. patent application Ser. No. 11/232,190 (published as US 2006/0190030 A1), Ser. No. 11/270,034 (published as US 2006/0122633 A1), and Ser. No. 11/583,627 (published as US 2008/0172035 A1), all of which were previously incorporated by reference in their entirety, and in U.S. patent application Ser. No. 11/656,141 (published as US 2008/0177380 A1), which is hereby incorporated by reference in its entirety.

As described above, one or more anchor deployment catheters may be used in an anchor deployment procedure. Certain variations of anchor deployment catheters may be particularly suitable for percutaneous procedures. For example, the catheters may be made of one or more flexible materials and/or may have a relatively low profile. Other variations of anchor deployment catheters may be particularly suitable for surgical procedures. For example, the catheters may be made of one or more relatively rigid materials. Other types of anchor deployment devices may also be used, as appropriate. The devices generally are configured to deploy tissue anchors, and as such, may be useful in any variety of procedures, including those procedures mentioned above. The devices may be especially useful in deploying anchors in areas of the body that are somewhat difficult to access. Moreover, in some variations, the devices may include one or more features that allow for enhanced control over the devices and over the anchor deployment process during use.

Some of the described devices comprise a shaft having a lumen for housing at least one anchor therein, and a mechanism for deploying the anchor distally from the lumen. The corresponding anchor may comprise one or more eyelets and may have an expanded configuration and a collapsed configuration. When the anchor is in its collapsed configuration, it may have a relatively small profile, which may enable the anchor to be housed within the lumen of the device shaft. When the anchor is deployed from the lumen, however, the anchor may assume its expanded configuration as it expands and secures into tissue. In some variations, the inner diameter of the lumen may be the same size as, or smaller than, the diameter of the eyelet of the anchor to be disposed therein when the anchor is in its expanded configuration. In some such variations, the legs of the anchor may be able assume a more linear shape when the anchor initially exits the lumen. The legs of the anchor may then assume a more curved shape as full expansion occurs. This may, for example, allow the anchor to securely implant into body tissue upon deployment. In certain variations, a device may comprise a shaft having a lumen for housing at least one anchor comprising at least one eyelet, where the inner diameter of the lumen is larger than the diameter of the eyelet.

As described briefly above, in certain variations of methods, a primary anchor deployment catheter may be used to deploy one or more anchors that are fixedly coupled to a coupling member. Upon deployment of the anchor or anchors into tissue, the coupling member tray effectively become anchored to the tissue, as well. The coupling member may then be used as a track for other anchor deployment catheters to deploy additional anchors over the coupling member. Examples of such anchor deployment methods are described in U.S. patent application Ser. No. 11/583,627 (published as US 2008/0172035 A1), which was previously incorporated by reference in its entirety.

FIGS. 5A-5L provide an illustrative depiction of a variation of a primary anchor deployment catheter (500). First, and referring specifically to FIGS. 5A-5C, primary anchor deployment catheter (500) comprises a proximal operating portion (502) and an elongated shaft (504) including a distal anchor deployment portion (506). Shaft (504) defines a lumen (508) (FIG. 5C), and includes a mechanism for deploying one or more anchors distally from the lumen, which will be described in more detail below.

While lumen (508) is generally circular in cross-section (FIG. 5J), a lumen of an anchor deployment catheter may have any suitable cross-section. For example, a lumen may have an elliptical cross-section, a rectangular cross-section, or any other geometrically desirable cross-section. When referring to the "inner diameter" of the lumen in those instances in which a non-circular cross-section is used (e.g., when an elliptical cross-section is used), the maximum dimension of the cross-section is intended. Additionally, while primary anchor deployment catheter (500) is depicted as having one lumen (508), in some variations an anchor deployment catheter may have more than one lumen. As an example, in certain variations, an anchor deployment catheter may comprise a lumen configured to hold one or more anchors, and another lumen configured for delivery of one or more therapeutic agents therethrough.

Figure 5C:
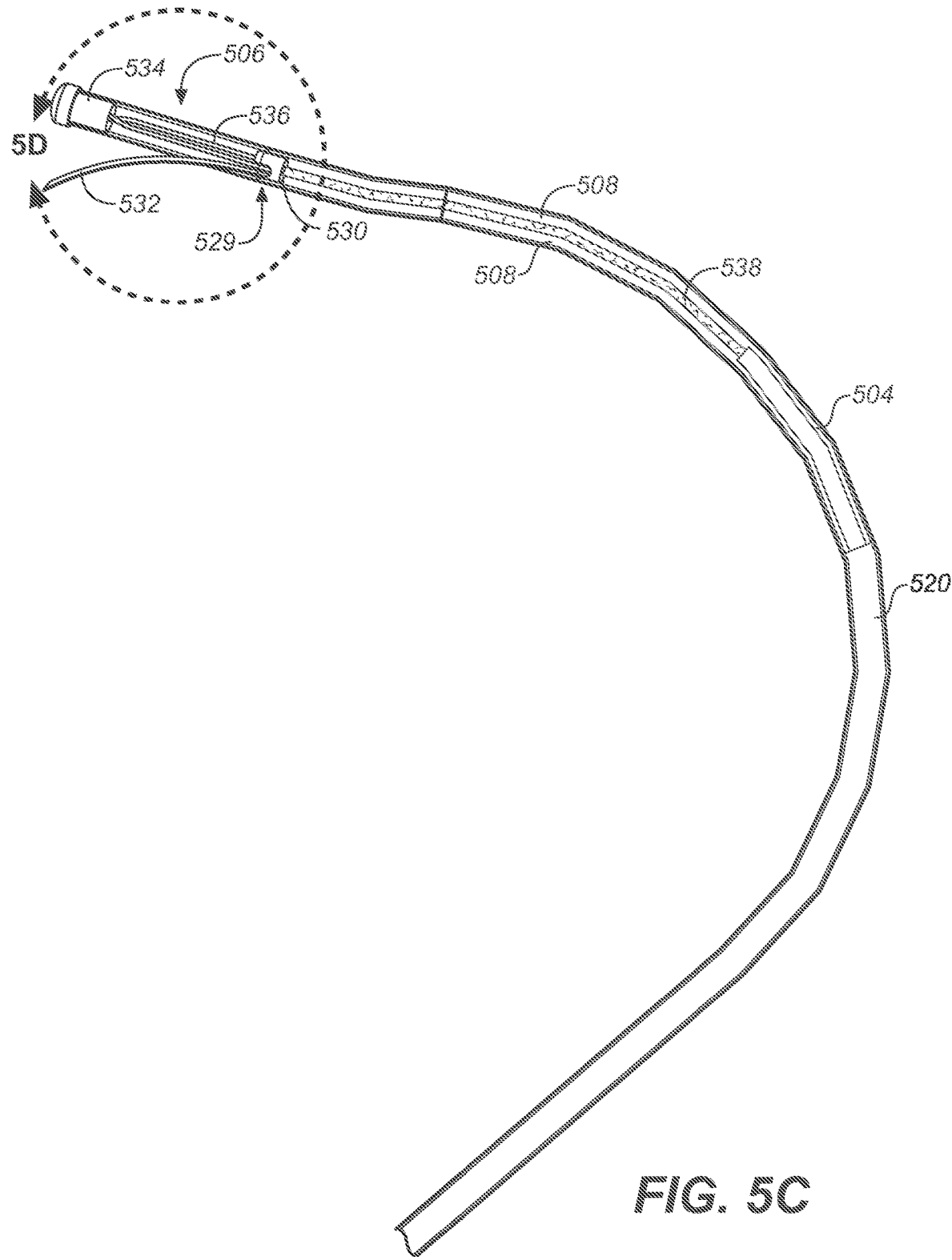
FIG. 5C is an enlarged view of region 5C of FIG. 5A.
Figure 5D:
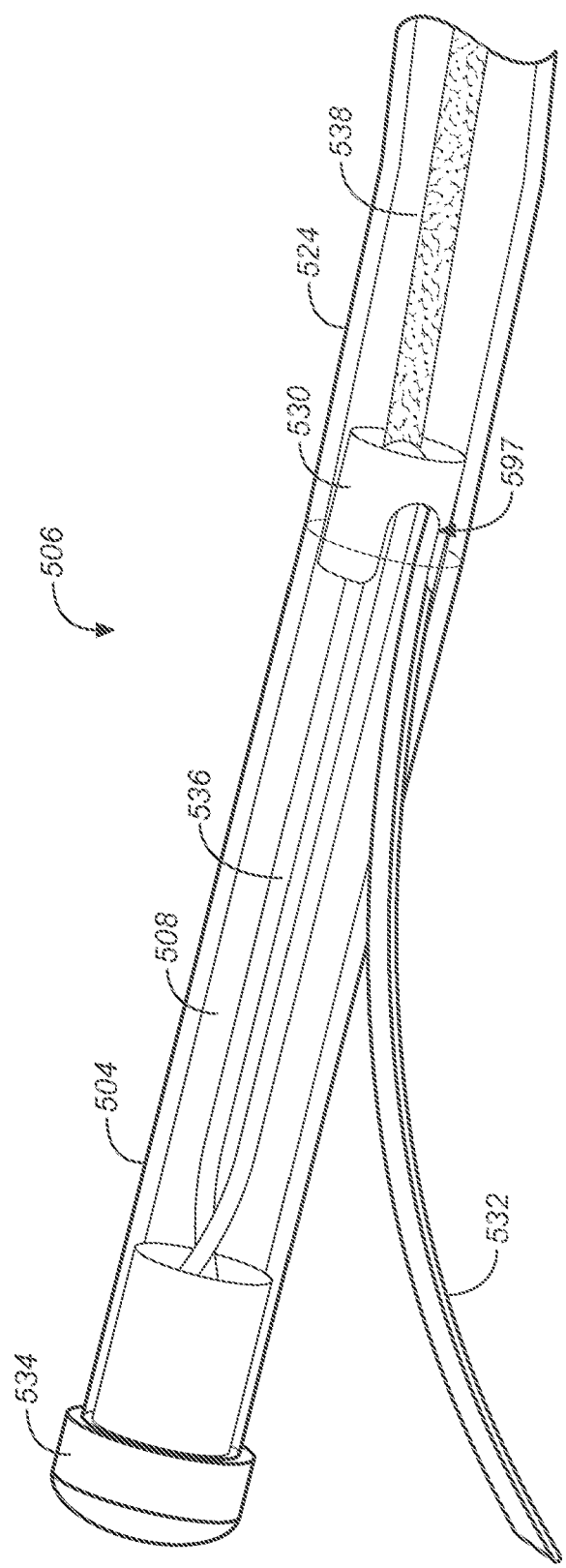
FIG. 5D is an enlarged view of region 5D of FIG. 5C.
Figures 5E, 5F:
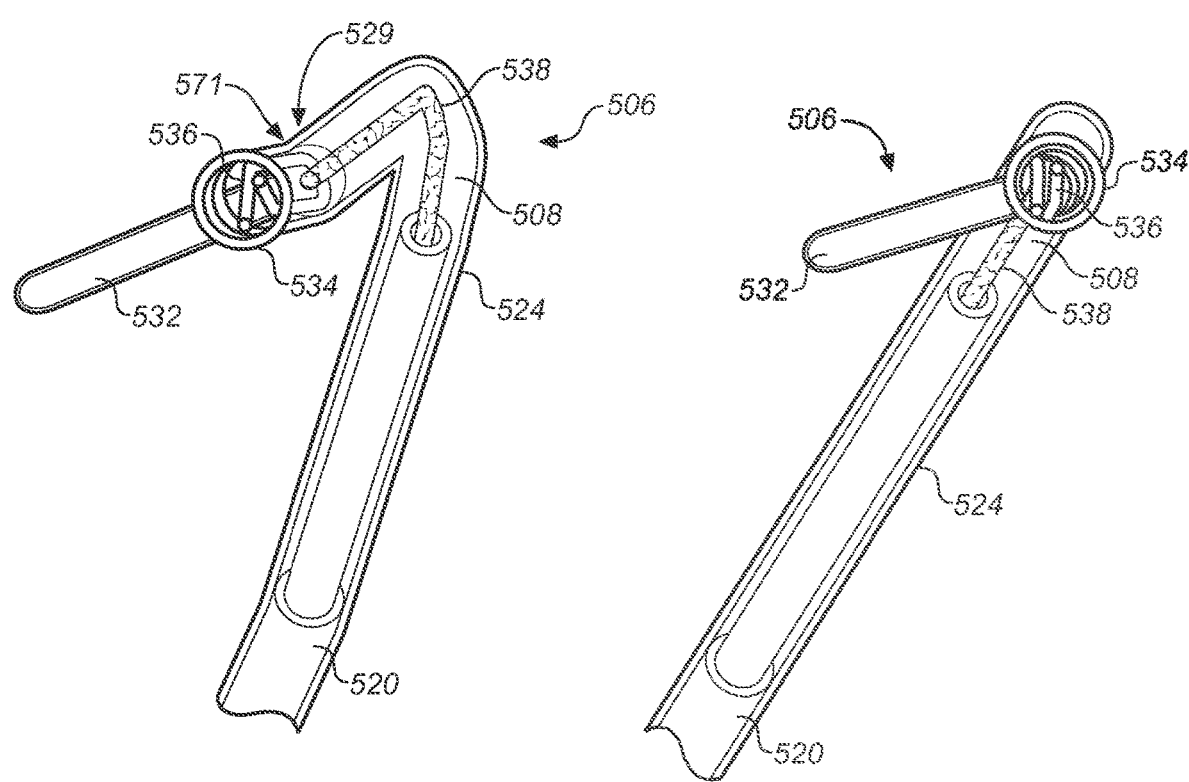
FIGS. 5E-5G are different perspective views of a distal portion of the anchor deployment device of FIG. 5A.
Figure 5G:
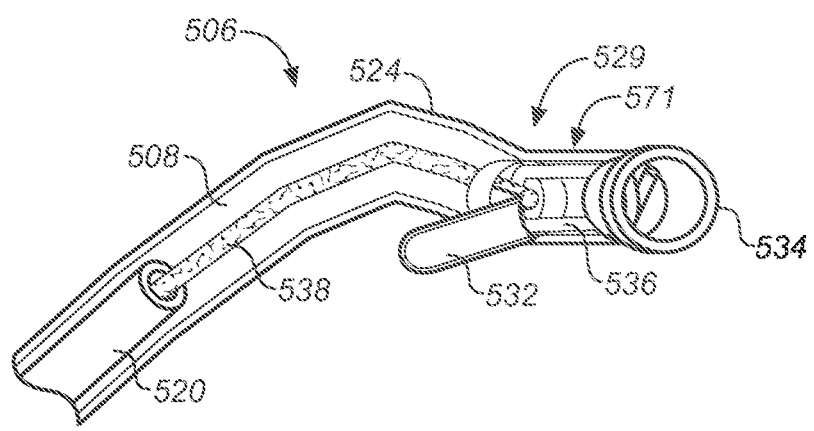
Figure 5H:
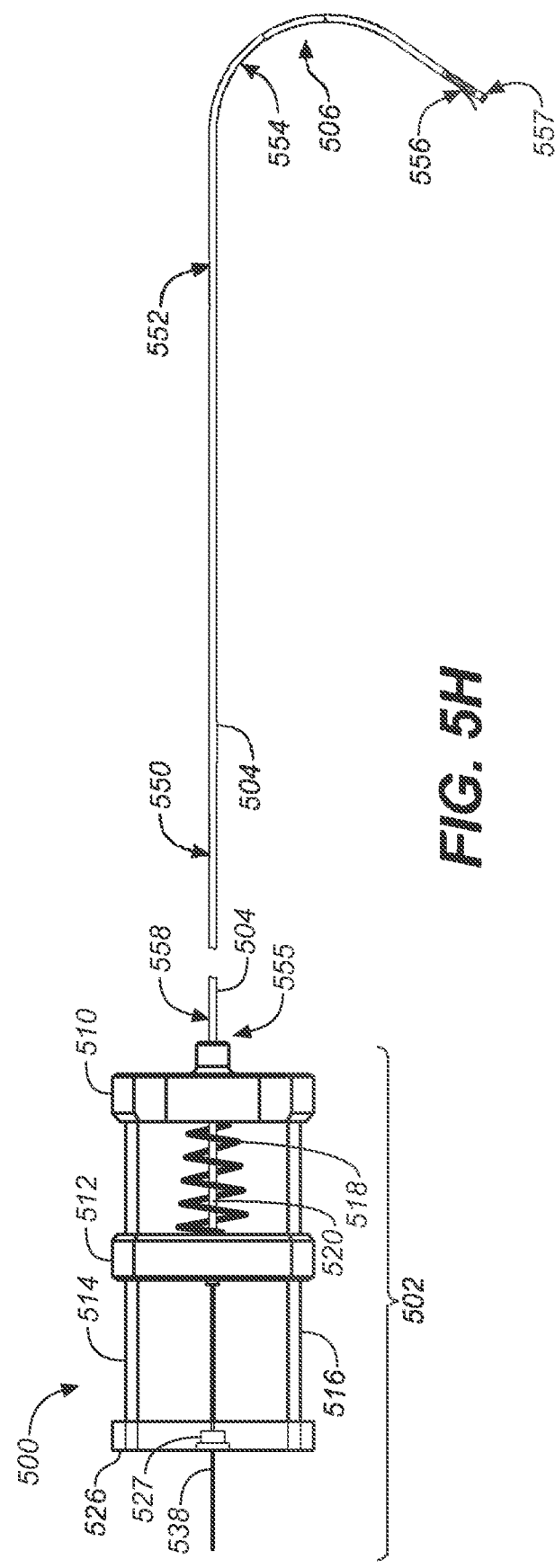

Referring now to FIGS. 5B, 5H, and 5I, proximal operating portion (502), which may be used to deploy one or more anchors from primary anchor deployment catheter (500), comprises a handle collar (510) and an actuator (512). Handle collar (510) is fixedly coupled to two slide pins (514) and (516), and actuator (512) is slidably coupled to the slide pins. A compression spring (518) is disposed between handle collar (510) and actuator (512). Compression spring (518) may have a spring constant of, for example, about 0.25 lb/inch to about 1.5 lb/inch, and/or may be formed of, for example, stainless steel. Compression spring (518) is coaxially disposed about a pushing member (520) that is fixedly coupled to actuator (512) and slidably disposed within an aperture (522) (FIG. 5B) of handle collar (510). Pushing member (520), actuator (512), and compression spring (518) may be formed as a single integral unit, or may be formed of at least two parts that are then interconnected.

Pushing member (520) passes through a sheath (524) of shaft (504) (FIG. 5J), to distal anchor deployment portion (506) of shaft (504). As shown in FIG. 5K, pushing member (520) comprises a distal tip portion (521). Distal tip portion (521) is tapered, such that its cross-sectional diameter at its distal end is smaller than its cross-sectional diameter at its proximal end, During use, pushing member (520) may be advanced within lumen (508), toward a tubular internal stop (530) (FIG. 5L) disposed within the lumen. Distal tip portion (521) may then be advanced into the lumen (not shown) of internal stop (530), thereby engaging the internal stop. The distal tip portion may continue to be advanced into the lumen of the internal stop, until the tapered shape of the distal tip portion prevents it from being able to move any further distally. Thus, the presence of internal stop (530) prevents pushing member (520) from being advanced too far distally during use. It may also thereby provide a tactile indication that the advancement of the pushing member is complete.

As shown in FIG. 5D, internal stop (530) also includes notches (597) for temporary coupling with an anchor, such as anchor (536). For example, the anchor may be aligned within notches (597), which may be used to orient the anchor for deployment. The anchor may be loosely seated within the notches or may have a tighter fit within the notches. It should be understood that while the anchor and the internal stop may be temporarily coupled in this way, the anchor and the internal stop generally are separate components, and are not integral with each other.

While pushing member (520) comprises a tapered distal portion (521) that limits its distal advancement, in some variations, a pushing member may alternatively or additionally comprise one or more other features that may be used to limit its distal advancement (or even proximal withdrawal). For example, while not being tapered, a pushing member may still have a varying cross-sectional dimension (e.g., a varying cross-sectional diameter) along at least a portion of its length.

Figure 5M:
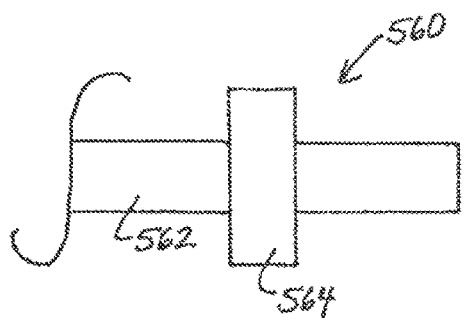
FIGS. 5M-5R depict different variations of pushing members for anchor deployment devices.
Figure 5N:
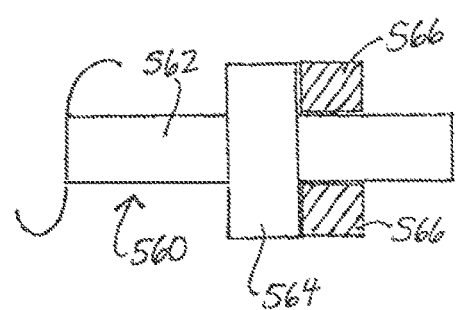

As an example, FIG. 5M shows a pushing member (560) comprising an elongated portion (562) and a ring (564)

surrounding the elongated portion. As shown in FIG. 5N, when pushing member (560) is advanced into a tubular internal stop (566), ring (564) contacts the tubular internal stop, preventing further distal movement by the pushing member. While a ring is shown, other configurations that essentially function as a shoulder may alternatively or additionally be used.

Figure 5O:
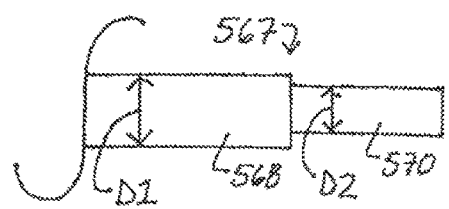
Figure 5P:
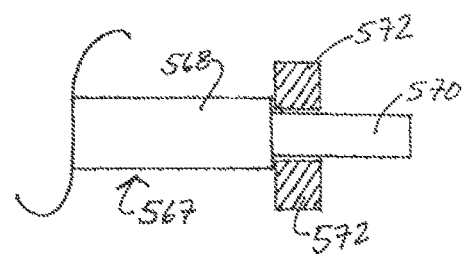

As another example, FIG. 5O shows a pushing member (567) comprising a first elongated member (568) coupled to a second elongated member (570). First elongated member (568) has a cross-sectional diameter (D1) that is larger than the cross-sectional diameter (D2) of second elongated member (570). As shown in FIG. 5P, when pushing member (567) is advanced into a tubular internal stop (572), cross-sectional diameter (D2) is small enough for second elongated member (570) to pass through tubular internal stop (572). However, cross-sectional diameter (D1) is too large for first elongated member (568) to be able to pass through tubular internal stop (572). As a result, tubular internal stop (572) prevents pushing member (567) from being advanced any further distally.

Figure 5Q:
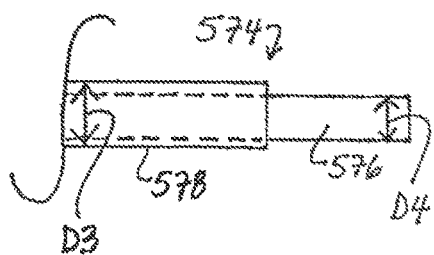
Figure 5R:
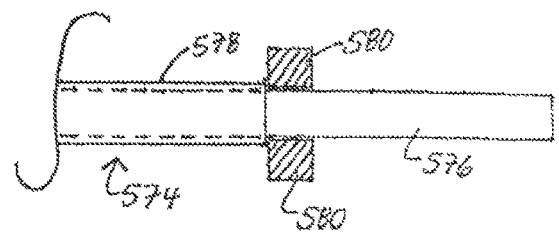

As an additional example, FIG. 5Q shows a pushing member (574) comprising an elongated member (576) slidably disposed within a tubular member (578). Tubular member (578) has an outer diameter (D3), while elongated member (576) has a smaller cross-sectional diameter (D4). Referring now to FIG. 5R, during use, pushing member (574) may be advanced toward a tubular internal stop (580), until tubular member (578) contacts tubular internal stop (580) and is prevented from being advanced any further distally. However, elongated member (576), with its smaller cross-sectional diameter (D4), may be able to continue being advanced distally through tubular internal stop (580). Elongated member (576) may, for example, be long enough to push an anchor out of an anchor deployment catheter during use, without being so long as to extend out of the anchor deployment catheter.

Other variations of pushing members are also contemplated for use with the devices described here. For example, in some variations, a pushing member may comprise one or more shoulders and/or angled regions that may be used to limit or control distal advancement of the pushing member during use. Moreover, in certain variations, a pushing member may not comprise any features for limiting its distal advancement.

Referring back to FIGS. 5C, 5E-5G, 5J, and 5K, pushing member (520) is also tubular. Additionally, in some variations, pushing member (520) may have a spiral cut (not shown) in its distal end. The spiral cut may, for example, provide the pushing member with enhanced flexibility, pushability, and/or maneuverability (e.g., thereby enhancing the ability of the pushing member to be advanced through an aortic arch). In some variations, pushing member (520) may be in the form of a hypotube having a spiral cut in its distal end (e.g., formed by a laser). While a spiral cut is described, certain variations of pushing members may include cuts with different configurations. For example, in some variations, a pushing member may include slits that are transverse to a longitudinal axis of the pushing member. In certain variations, a pushing member may comprise a coiled wire or ribbon at its distal end (e.g., rather than a spiral cut, or in addition to a spiral cut). Moreover, some pushing members may include one or more of these features in a different location, either as an alternative to, or in addition to, including the features in their distal ends.

Because pushing member (520) is tubular, one or more coupling members may pass through the center of pushing member (520), For example, and as shown in FIG. 5J, a coupling member (as shown, a tether (538)) passes through the center of pushing member (520). Pushing member (520) comprises a liner (540) that may be formed of one or more materials that enhance the advancement of the pushing member along a coupling member. For example, liner (540) may be formed of high-density polyethylene (HDPE) or polytetrafluoroethylene (PTFE), such as etched polytetrafluoroethylene, or flattened polyimide. While one variation of a pushing member has been described, other suitable variations of pushing members may be used, such as pushing members that do not comprise liners, that are not spiral cut, and/or that are not tubular. Moreover, in some variations of devices and/or methods, more than one pushing member may be employed. As an example, a device may be configured to deploy two anchors simultaneously, and may comprise two pushing members, with one pushing member to be used for each anchor.

Referring again to FIGS. 5B, 5H, and 5I, proximal operating portion (502) also comprises an O-ring housing (526) including an O-ring (527). Tether (538), which is coupled to an anchor (536) and runs through the entirety of primary anchor deployment catheter (500) (as discussed in additional detail below), passes through O-ring (527). O-ring (527) may be used to help maintain tension on tether (538), thereby limiting the likelihood that tether (538) will bunch up during use (e.g., toward the distal end of primary anchor deployment catheter (500)). O-ring (527) may be made of, for example, silicone, ethylene propylene terpolymer rubber, butyl rubber, polyisoprene, one or more thermoplastic elastomers (e.g., one or more KRATON® thermoplastic elastomers), or a combination thereof. While primary anchor deployment catheter (500) is described as including an O-ring, in some variations, a primary anchor deployment catheter may not include an O-ring. Additionally, in certain variations, a secondary anchor deployment catheter may include an O-ring. Moreover, some variations of catheters may include an element that has a different configuration from an O-ring, but that can also be used to maintain tension on a tether.

During use of primary anchor deployment catheter (500), an operator may depress actuator (512), thereby causing compression of compression spring (518) and slidable movement of pushing member (520) within lumen (508) of shaft (504). This allows pushing member (520) to contact an anchor disposed within lumen (508) of shaft (504), and push the anchor out of the lumen so that the anchor is deployed into a target site. It should be understood that while FIGS. 5A, 5B, 5H, and 5I show actuator (512) as having a particular geometry or shape, any suitable shape may be used. It may be desirable, however, for actuator (512) to have an ergonomic shape, so that it is comfortable for operation by depression with a user's thumb, for example. It should also be noted that in some variations, different actuation mechanisms may alternatively or additionally be used.

While the mechanism for deploying an anchor distally from the shaft lumen depicted in FIGS. 5C, 5E-5G, and 5K includes a slidable anchor, a spring, and a pushing member slidably disposed within the shaft lumen, any suitable deployment mechanism may be used with the devices, methods, and kits described here. As an example, some variations of anchor deployment devices may not comprise a spring, while other variations of anchor deployment devices may comprise more than one spring. Moreover, while a pushing member is shown, other appropriate mechanisms may be used, including but not limited to hydraulic mechanisms, pressurized air mechanisms, or any other mechanisms capable of providing an axial force on an anchor that is sufficient to deploy the anchor distally from a lumen of a shaft. Similarly, all or a portion of the anchor may be made from, or coated or embedded with, one or more magnetic materials, and a corresponding magnet (e.g., a magnet on the tip of a catheter) may be placed distally of the anchor to withdraw the anchor from the lumen. Additionally, any suitable component may be used as part of such a mechanism (e.g., pistons, plungers, cables, pumps, etc.), and the mechanism for deploying the anchor may be made from any suitable material or materials, such as one or more metal alloys (e.g., stainless steel, nickel titanium alloy), polymers (e.g., nylon, polyetheretherketone (PEEK), polyether block amides, polytetrafluoroethylene (PTFE)), mixtures or combinations thereof, and the like. In one variation, the mechanism for deploying the anchor may comprise a pushing member made of stainless steel and coated at least in part with polytetrafluoroethylene, which may help to reduce friction when sliding within the lumen of the catheter shaft.

The mechanism for deploying anchors may also be reinforced along those sections that do not traverse curves within the device shaft (e.g., in the case of a pushing member, the pushing member may be reinforced along its straight length). The mechanism may be reinforced with any suitable material or materials. As an example, in some variations, a metal or polymer tubing may be used, such as a metal hypotube. Similarly, the distal end of the mechanism may be reinforced with an element that helps to impart the axial force transmitted from the actuation onto the collapsed anchor.

Referring now to FIGS. 5A, 5C-5G, 5K, and 5L, distal anchor deployment portion (506) of shaft (504) is the location from which one or more anchors may be deployed. As shown, distal anchor deployment portion (506) includes a curved region (528) (FIG. 5A), as well as an inflection point (529) (FIGS. 5C and 5G). In some variations, distal anchor deployment portion (506) may further comprise one or more additional curves. For example, distal anchor deployment portion (506) may comprise another curved region (571) (FIGS. 5E and 5G) that is distal to inflection point (529). Curved region (571) may, for example, curve away from external stop (532), which is described in further detail below.

The curvature of an anchor deployment device may depend, for example, on the characteristics of the target anatomy. Having at least one preformed curve near the distal end of the shaft may help a catheter to access areas that may otherwise be difficult to reach. For example, curved region (528) and/or curved region (571) may help primary anchor deployment catheter (500) to point toward tissue and/or to contact tissue upon exiting through an opening in a guide tunnel, and/or to point away from the guide tunnel. Inflection point (529) may also help to position the distal end of primary anchor deployment catheter (500) with respect to tissue. Curved region (528) forms an arc that may have any suitable or desirable central angle. For example, the central angle may be from about 15 degrees to about 270 degrees, from about 45 degrees to about 180 degrees, or from about 50 degrees to about 120 degrees. It should be noted that some variations of anchor deployment devices may not include any curved regions or inflection points, or may include multiple (i.e., at least two) curved regions and/or inflection points. Variations of curved anchor deployment devices are discussed in additional detail below.

In some variations in which the flexible percutaneous devices described here are used in the repair of a heart valve (e.g., a mitral valve), and particularly when the valve is approached subannularly, the catheter shaft may have a radius of curvature that is larger than that of the annulus of the valve. In this way, when the catheter is situated in the subannular groove, the tip of the catheter may point outward against the annulus and the ventricular wall. In certain variations, the tip of the catheter may be beveled. For example, the tip may have one or more diagonal cuts and/or other various shapes on its edge, rather than having a square-cut edge. This may, for example, help to direct the anchors outward upon deployment. Of course, some variations of anchor deployment catheters may include tips without any beveling (e.g., having a square-cut edge).

As shown in FIGS. 5C-5G, 5K, and 5L, distal anchor deployment portion (506) includes sheath (524), internal stop (530) disposed within sheath (524), and an external stop (532). Distal anchor deployment portion (506) also comprises the distal tip (534) of primary anchor deployment catheter (500). External stop (532) is coupled to (e.g., welded to) or integral with internal stop (530), and extends through an opening (not shown) in sheath (524), The opening in the sheath may have any appropriate size and configuration. For example, the opening may be circular or oval, or may be in the form of a slot. External stop (532) is in the form of an elongated flap and may, for example, have a width of about 0.05 inch to about 0.2 inch (e.g., about 0.08 inch), and/or a length of about 0.1 inch to about 0.3 inch (e.g., about 0.2 inch).

Internal stop (530) and/or external stop (532) may be made from, for example, one or more metal alloys (e.g., stainless steel and/or Nitinol), and/or one or more polymers (e.g., PEBAX® 7233 polymer). The internal and external stops may be made of the same material or materials, or may be made of different materials. In some variations, the internal and/or external stops may be laser-cut. While external stop (532) is coupled to or integral with internal stop (530), in some variations, an external stop may not be coupled to or integral with an internal stop. For example, an external stop may be formed of a piece of material (e.g., a polymer) that is formed separately from an anchor deployment catheter and then is thermally fused to the outer surface of the anchor deployment catheter. Additionally, while an anchor deployment catheter including one internal stop and one external stop is shown, some variations of anchor deployment catheters may not comprise an internal stop and/or may not comprise an external stop. Moreover, certain variations of anchor deployment catheters may comprise multiple internal stops and/or external stops.

During use, as anchor (536) is being deployed from primary anchor deployment catheter (500), internal stop (530) helps to prevent pushing member (520) from being pushed too far distally. More specifically, and as described above, as pushing member (520) is pushed distally, distal tip portion (521) enters the lumen of internal stop (530). Distal tip portion (521) may be tapered, such that its proximal end has a larger cross-section than its distal end. This tapering may be configured so that at a certain point, the cross-sectional size of the distal tip portion is too large to fit within the lumen of the tubular internal stop. As a result, the pushing member cannot be advanced any further distally.

Figure 5S:
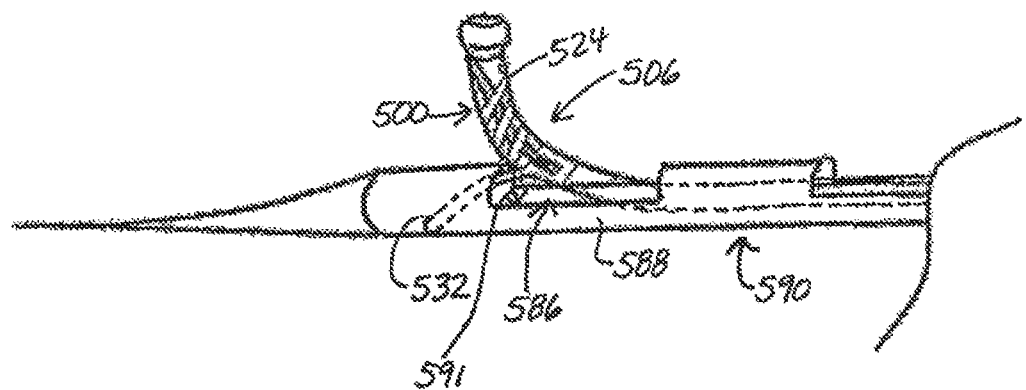
FIG. 5S is an illustrative depiction of a variation of a method for deploying anchors using the anchor deployment device of FIG. 5A.

Additionally, external stop (532) may function to prevent primary anchor deployment catheter (500) from being over-advanced through an opening in a guide tunnel during the anchor deployment process. This, in turn, may help to limit the likelihood of damage to the target site during use of the anchor deployment catheter. For example, FIG. 5S shows distal anchor deployment portion (506) of primary anchor deployment catheter (500) being advanced through an opening (586) in a wall portion (588) of a guide tunnel (590). As distal anchor deployment portion (506) is advanced through opening (586), external stop (532) remains within the lumen (591) of the guide tunnel. External stop (532) bends back as distal anchor deployment portion (506) continues to be advanced. At a certain point, distal anchor deployment portion (506) will not be able to be advanced any further. This may occur, for example, because external stop (532) is not able to bend back any more, and/or because wall portion (588) of guide tunnel (590) becomes wedged between external stop (532) and sheath (524) (as shown in FIG. 5S). Thus, external stop (532) may help prevent primary anchor deployment catheter (500) from being inadvertently advanced too far out of guide tunnel (590).

While one variation of an external stop has been shown, other suitable variations of external stops may alternatively or additionally be used. In some variations, an external stop may be relatively straight, while in other variations, an external stop may include one or more curves (e.g., to promote smooth tracking of the catheter or device of which the external stop is a part). In certain variations, an external stop may have a curvature that is designed to correspond with the curvature of the target site.

Figure 5T:
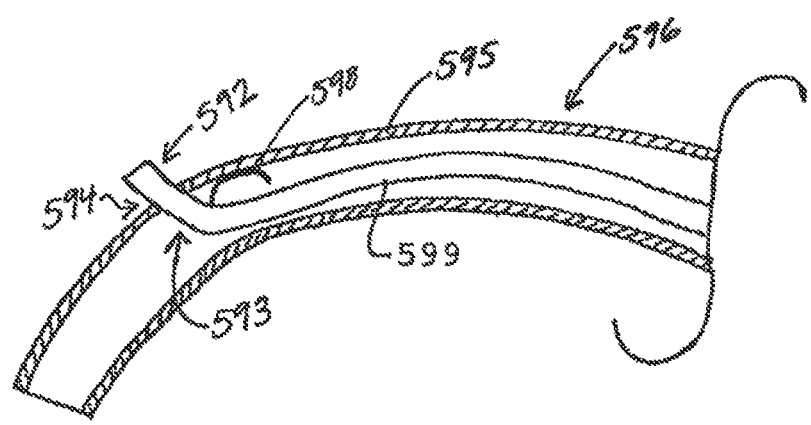
FIG. 5T is an illustrative depiction of another variation of a method for deploying anchors using another variation of an anchor deployment device.

FIG. 5T depicts another variation of an external stop. As shown there, a distal portion (592) of an anchor deployment catheter (593) is advanced through an opening (594) in a wall portion (595) of a guide tunnel (596). Anchor deployment catheter (593) comprises an elongated member (599) and an external stop (598). As distal portion (592) of anchor deployment catheter (593) is advanced through opening (594), external stop (598) bends back from elongated member (599). Eventually, the external stop will prevent the anchor deployment catheter from being advanced any further distally within the guide tunnel. Although external stop (598) is similar to external stop (532) shown above, it is oriented differently with respect to the opening in the guide tunnel during use. Moreover, as shown in FIG. 5T, external stop (598) functions primarily by bending backward until it can bend no further. External stop (532) (FIG. 5S), on the other hand, may function by bending backward until it can bend no further, and/or by providing a location (between the external stop and the wall or sheath of the anchor deployment catheter) in which the guide tunnel wall can become wedged. In some variations, external stop (598) may be formed of, for example, a flat ribbon, such as a Nitinol flat ribbon. While not shown here, other variations of devices may comprise internal and/or external stops comprising one or more flat ribbons.

Figure 5U:
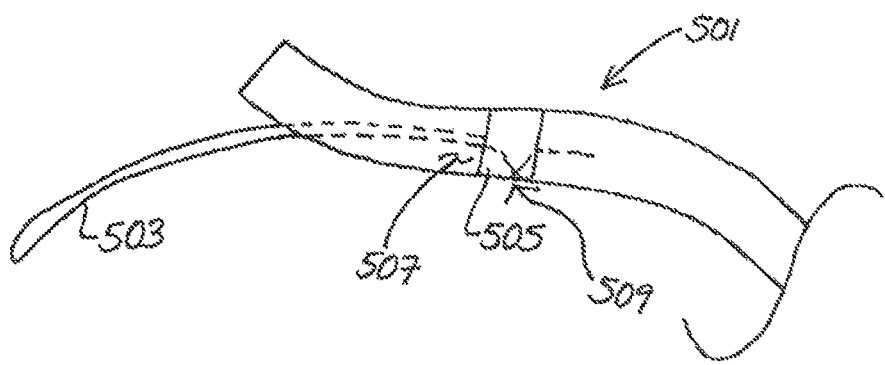
FIGS. 5U-5X depict additional variations of anchor deployment devices.

External stops may have any suitable size, shape, and configuration. In some variations, an external stop may be integrally formed or fixedly coupled to another component of a catheter or other device. For example, an external stop may be integral with, or fixedly coupled to, an internal stop, and/or one or more other components of a catheter. FIG. 5U shows a variation of a catheter (501) comprising an external stop (503) in the form of an elongated wire loop form (e.g., comprising Nitinol). As shown, a portion of external stop (503) is disposed within a lumen (507) of catheter (501), while the loop portion of external stop (503) extends externally of catheter (501). However, in some variations, an external stop comprising a wire form may include different portions that are internally or externally located relative to a catheter body. In certain variations, an external stop may even be completely external to a catheter body. External stop (503) comprises a hinge region (509) that allows external stop (503) to bend or move (e.g., when compressed against an inner wall of a catheter during use), As shown, external stop (503) is coupled to catheter (501) by a ring (505) (e.g., formed of one or more metals and/or metal alloys). However, an external stop may be coupled to a catheter body in other ways. As an example, a polymer sleeve (e.g., formed of 55D PEBAX® polymer) may be used to attach an external stop to a catheter body. As another example, an external stop may be welded to a connecting member, and the resulting assembly may be bonded to the catheter body.

Figure 5V:
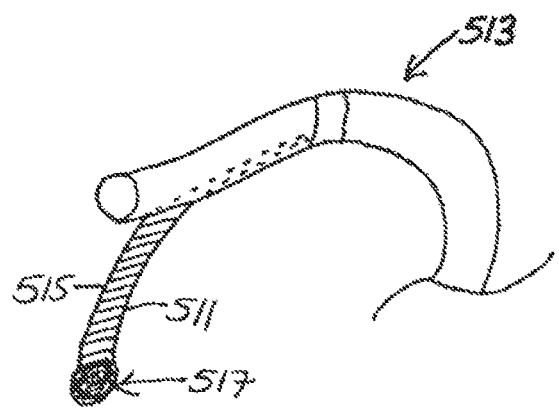
Figure 5W:
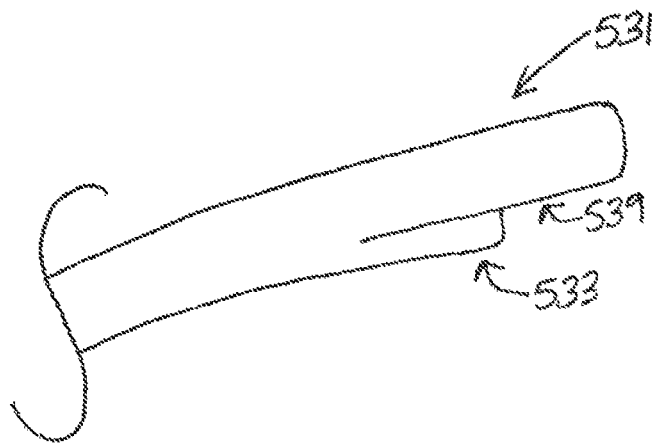
Figure 5X:
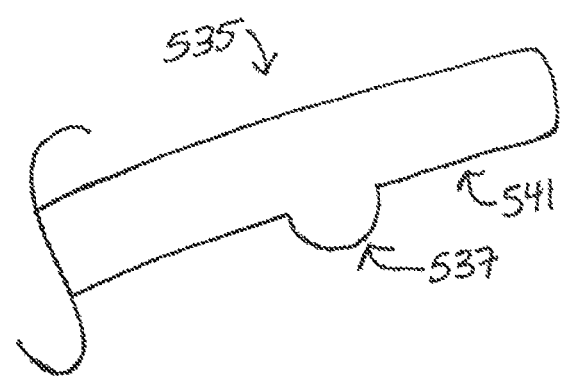

Still other variations of external stops may be used. For example, and as shown in FIG. 5V, in certain variations, an external stop (511) of a catheter (513) may comprise a leaf spring (515) (e.g., formed of stainless steel). In some variations, leaf spring (515) may have a thickness of about 0.01 inch. Leaf spring (515) has a rounded distal end (517) that may be formed, for example, by heating and molding leaf spring (515). Rounded distal end (517) may, for example, be relatively unlikely to cause damage to a guide tunnel or other device during use. It should be noted, of course, that other variations of external stops may be configured differently. For example, in some variations, an external stop may have a rounded end, but may not comprise a leaf spring, or an external stop may not have a rounded end. Additional non-limiting examples of external stops are shown in FIGS. 5W and 5X. In FIG. 5W, a catheter (531) comprises an external stop (533) in the form of a molded appendage or thumb protruding from the outer surface (539) of the catheter. Similarly, FIG. 5X shows a catheter (535) comprising an external stop (537) in the form of a protrusion extending from the outer surface (541) of the catheter.

Other appropriate internal or external stop configurations may also be used. As an example, in some variations, a catheter may comprise one or more wire formations that may function as external stops, and that are different from the elongated wire loop form depicted in FIG. 5U above. As another example, certain variations of catheters may comprise internal and/or external wings and/or bumps that may help to control the advancement of the catheters (e.g., relative to other catheters). Some variations of stops may function to slow or temporarily stop the advancement of a device. This may allow the operator an opportunity to determine whether to continue to advance the device. For example, in certain variations, a device may comprise one or more stops that essentially function as "speed bumps," providing resistance and thereby slowing the advancement of the device. This may, for example, provide the operator with a signal that it may be desirable to stop advancing the device. In some variations, the stops may comprise a round portion followed by a flattened portion, where the round portion is configured to initially provide resistance to further advancement of the device. If the operator continues to advance the device despite the resistance, then the flattened portion may allow for a normal rate of advancement to resume. In some variations, a catheter may comprise one or more visor-shaped stops that may be designed, for example, to provide increasing resistance as the catheter continues to be advanced.

External stops may be located in any suitable location of a device. In some variations, an anchor deployment catheter may comprise one or more external stops that are coupled to its distal end. As an example, a catheter may comprise a spring cone at its distal end that provides tactile feedback to the operator as to the location of the device. As another example, a device may comprise one or more friction-generating materials (e.g., a latex film) in one or more locations that are selected to result in increased resistance to device advancement when contacted. As an additional example, a catheter may comprise an expandable collar in its distal portion that may limit or prevent advancement of the catheter once expanded.

Additional non-limiting examples of stops include petals that are configured to anchor at the side of the myocardium during a heart valve repair procedure and then to retract after at least one anchor has been deployed. The surface area and/or rigidity of the petals may be selected to prevent them from permanently penetrating into the myocardium.

In some variations, a device may comprise a catheter and a sheath surrounding at least a portion of the catheter, Where the portion includes a distal portion of the catheter. The sheath may be slidable with respect to the catheter, while also being fixed to the catheter in a distal portion of the device. During use, the device may be positioned such that the catheter and sheath contact a tissue surface. As the device is pressed against the tissue surface, the sheath may become lamer in diameter (e.g., like an umbrella), and may effectively prevent or limit any further movement toward or into the tissue by the catheter. In this way, the sheath may function as a stop element for the device.

While the external stops shown above are depicted as helping to control the advancement of a primary anchor deployment catheter through an opening in a wall portion of a guide tunnel, external stops may be used with any of a number of different devices or combinations of devices. As an example, in some variations, a secondary anchor deployment catheter may comprise one or more external stops (e.g., to control its advancement through an opening in a wall portion of a guide tunnel). As another example, in certain variations, a catheter that is not an anchor deployment catheter may comprise one or more external stops. As an additional example, a device comprising one or more external stops may be advanced out of another device that is not a guide tunnel.

As depicted in FIGS. 5C-5G, 5K, and 5L, anchor (536) has been loaded into lumen (508) of shaft (504). Tether (538) is coupled to anchor (536), and extends proximally through primary anchor deployment catheter (500), exiting at the proximal end of proximal operating portion (502). For example, FIG. 5J shows a cross-sectional view of a region of shaft (504) that is substantially proximal to distal anchor deployment portion (506), and that includes sheath (524), pushing member (520), and tether (538).

Generally, a primary anchor deployment catheter will include at least one tether that is fixedly coupled to the anchor that is being deployed. Thus, deployment of the anchor also may result in deployment of the tether. As an example, tether (538) of primary anchor deployment catheter (500) may be fixedly coupled to anchor (536), For example, the tether may be knotted around an eyelet in the anchor, or in variations in which the tether comprises multiple filaments, the anchor may be threaded through the filaments. In some variations, a tether may be fused around an anchor and/or to an anchor by applying heat to the tether and/or anchor. For example, the tether may comprise multiple braided strands, and the free ends of the strands may be heat-fused together around the anchor (e.g., after the anchor has been inserted between the strands). This may, for example, provide for a strong tether-anchor coupling that may be formed in a relatively controlled fashion (e.g., such that the remaining length of tether is neither too short nor too long). In certain variations, a tether may be knotted or otherwise tied to an anchor, and the resulting coupling may be heated to weld or fuse different parts of the tether together (e.g., thereby enhancing the security of the coupling). For example, a tether may be secured to an anchor using one or more knots (e.g., overhand knots, double-overhand knots, bowline knots, figure-of-eight knots, Ashley knots, etc.). Alternatively or additionally; a tether may be secured to an anchor using one or more splices (e.g., back splices, eye splices), which may be relatively space-efficient, may be self-locking, and/or may result in relatively little stress on the tether. Heat and/or compression may be applied to the knots and/or splices after formation. In certain variations, a tether may be coupled to an anchor using one or more adhesives. Other appropriate coupling mechanisms may alternatively or additionally be used. Additional examples of coupling mechanisms are described, for example, in U.S. Provisional Application Ser. Nos. 61/083,109, filed on Jul. 23, 2008, and 61/160,018, filed on Mar. 13, 2009, and in U.S. patent application Ser. No. 12/505,332, filed on Jul. 17, 2009, all of which are hereby incorporated by reference in their entirety.

While not shown, in some variations, an anchor deployment catheter may comprise at least one ring in its distal anchor deployment portion. The ring may provide enhanced structural stability to the distal deployment portion, and may be located, for example, between an internal stop in the catheter and the distal tip of the catheter. In some variations, the ring may surround a sheath of the catheter, and may be in the form of a hypotube. Other reinforcement structures may alternatively or additionally be used, as appropriate.

Referring specifically now to FIG. 5H, shaft (504) of primary anchor deployment catheter (500) may generally be selected to have a length suitable for accessing the desired target site. As shown there, shaft (504) includes a proximal shaft region (550), a mid-shaft region (552), a first intermediate shaft region (554), a second intermediate shaft region (556), and a distal shaft region (557). Proximal shaft region (550) may be relatively long depending, for example, on the application. In some variations (e.g., some variations in which primary anchor deployment catheter (500) has to traverse a relatively long path to reach a target site), proximal shaft region (550) may have an extended length of about 100 centimeters to about 145 centimeters (e.g., about 110 centimeters to about 125 centimeters, such as about 118 centimeters), Where the "extended length" refers to the length of the region when straight. In certain variations (e.g., certain variations in which primary anchor deployment catheter (500) has to traverse a shorter path to reach a target site, such as certain variations in which the primary anchor deployment catheter enters the body via the groin), proximal shaft region (550) may have an extended length of about 10 centimeters to about 40 centimeters (e.g., about 20 centimeters to about 30 centimeters, such as about 25 centimeters).

In some variations, mid-shaft region (552) may have an extended length of about 5 centimeters to about 30 centimeters (e.g., about 10 centimeters to about 25 centimeters, such as about 17 centimeters), first intermediate shaft region (554) may have an extended length of about 3 centimeters to about 10 centimeters (e.g., about 3 centimeters to about 7 centimeters, such as about 5 centimeters), second intermediate shaft region (556) may have an extended length of about 1 centimeter to about 5 centimeters about 1 centimeter to about 3 centimeters, such as about 2 centimeters), and/or distal shaft region (557) may have an extended length of about 1 millimeter to about 10 millimeters (e.g., about 1 millimeter to about 6 millimeters, such as about 3 millimeters). In certain variations, such as when a primary anchor deployment catheter is configured for percutaneous use, the shaft of the primary anchor deployment catheter may have an overall extended length of about 110 centimeters to about 190 centimeters (e.g., about 120 centimeters to about 180 centimeters, or about 130 centimeters to about 160 centimeters, such as about 145 centimeters). Of course, primary anchor deployment catheter (500) is only one exemplary variation of an anchor deployment catheter, and other variations of anchor deployment catheters or other types of catheters may have different configurations. As an example, a catheter may comprise a shaft having a different number of regions having different lengths, or may even comprise a uniform construction along the entirety of its length. Any suitable catheter configuration may be employed.

Each of the regions of shaft (504) shown in FIG. 5H may be formed of the same material or materials, or some or all of the regions may be formed of different materials. For example, it may be desirable for a more proximal region, such as proximal shaft region (550), to be formed of one or more relatively stiff materials (e.g., for enhanced pushability), while a more distal region, such as second intermediate region (556) or distal shaft region (557), is formed of one or more relatively flexible materials (e.g., for maneuverability).

Examples of materials which may be suitable for any or all of the regions or components of a catheter or other device include polymers, such as polyether-block co-polyamide polymers (e.g., PEBAX® polyether block amide copolymer), copolyester elastomers, thermoset polymers, polyolefins (e.g., polypropylene or polyethylene, including high-density polyethylene (HDPE) and low-density polyethylene (LDPE)), polytetrafluoroethylene (e.g., TEFLON™ polymer) or other fluorinated polymers, ethylene vinyl acetate copolymers, polyamides, polyimides, polyurethanes (e.g., PGLYBLEND™ polymer), polyvinyl chloride (PVC), fluoropolymers (e.g., fluorinated ethylene propylene (FEP), perfluoroalkoxy (PFA) polymer, polyvinylidenefluoride (PVDF), etc.), polyetheretherketones (PEEKs), silicones, and copolymers and blends thereof. Examples of polyamides include Nylon 6 (e.g., ZYTEL® HTN high performance polyamides from DuPont™), Nylon 11 (e.g., RILSAN® B polyamides from Arkema Inc.), and Nylon 12 (e.g., GRILAMID® polyamides from EMS-Grivory, RILSAN® A polyamides from Arkema Inc., and VESTAMID® polyamides from Degussa Corp.).

In certain variations, a catheter or other device may comprise one or more reinforced polymers. For example, a catheter may comprise one or more polymers reinforced with one or more metals and/or metal alloys (e.g., stainless steel or a shape memory metal such Nitinol). Polymers may also be reinforced with textile and/or metal meshes, braids, and/or fibers. In some variations, a catheter may comprise one or more polymer composites comprising one or more particulate or fibrous fillers. When composites are used, the fillers may be selected to impart a variety of physical properties, such as toughness, stiffness, density, and/or radiopacity.

In some variations, a catheter or other device may be formed of multiple polymers. As an example, in certain variations, an anchor deployment catheter may be formed of a blend of different polymers, such as a blend of high-density polyethylene and low-density polyethylene. As another example, an anchor deployment catheter may be formed of different polymers having different durometers. For example, a catheter may include different durometer polymers along its length. In certain variations, a catheter may comprise a first section comprising VESTAMID® polymer, a second section comprising a blend of PEBAX® polymer and VESTAMID® polymer (e.g., 70% PEBAX® polymer and 30% VESTAMID® polymer), a third section comprising a blend of PEBAX® polymer and VESTAMID® polymer (e.g., 90% PEBAX® polymer and 10% VESTAMID® polymer), and/or a fourth section comprising 100% PEBAX® polymer. Of course, other suitable materials may also be used. In some variations, the first section may have an extended length of about 5 centimeters to about 30 centimeters (e.g., about 10 centimeters to about 25 centimeters, such as about 17 centimeters), the second section may have an extended length of about 3 centimeters to about 10 centimeters (e.g., about 3 centimeters to about 7 centimeters, such as about 5 centimeters), the third section may have an extended length of about 1 centimeter to about 5 centimeters (e.g., about 1 centimeter to about 3 centimeters, such as about 2 centimeters), and/or the fourth section may have an extended length of about 1 millimeter to about 10 millimeters (e.g., about 1 millimeter to about 6 millimeters, such as about 3 millimeters), In certain variations, a catheter may include a fifth, proximal-most section comprising, for example, GRILAMID® polymer. In some variations, such as some variations in which the catheter needs to traverse a relatively long percutaneous path to reach a target site, the fifth section may have an extended length of, for example, about 100 centimeters to about 145 centimeters (e.g., about 110 centimeters to about 125 centimeters, such as about 118 centimeters). In certain variations, such as certain variations in which the catheter needs to traverse a relatively short percutaneous path to reach a target site, the fifth section may have an extended length of, for example, about 10 centimeters to about 40 centimeters (e.g., about 20 centimeters to about 30 centimeters, such as about 25 centimeters).

While the wall of a catheter may be formed of a single layer, some variations of catheters may include walls having multiple layers (e.g., two layers, three layers). For example, a catheter may comprise an outer catheter wall comprising one or more flexible polymers and an inner reinforcing wall formed, for example, from a braided or woven mesh (e.g., a polymer or metal braided or woven mesh). The inner reinforcing wall may help to provide stiffness to selected regions of the catheter. Some variations of catheters may include at least two sections that are formed of different materials and/or that include different numbers of layers. Additionally, certain variations of catheters may include multiple (e.g., two, three) lumens. The lumens or walls may, for example, be lined and/or reinforced (e.g., with braiding or winding). The reinforcing structures, if any, may be metallic or may comprise one or more non-metals or polymers having a higher durometer.

As shown in FIG. 5H, shaft (504) also comprises a strain relief region (558). Strain relief region (558) may, for example, prevent high strain in the area between the port (555) of proximal operating portion (502) and shaft (504). This, in turn, may decrease the likelihood of breakage occurring in this area. In certain variations, strain relief region (558) may provide additional support (e.g., increasing the overall maneuverability of the catheter). In some variations, strain relief region (558) may be in the form of a shrink tube with a friction fit, or a metal and/or coil structure. In certain variations, strain relief region (558) may be in the form of an extra polymer layer over shaft (504). The extra polymer layer may or may not chemically bond to the shaft. In some variations, the extra polymer layer may comprise 100% PEBAX® polymer, or may comprise a mixture of polymers, such as a mixture of a PEBAX® polymer with one or more other polymers.

As described above, in some variations, after a primary anchor deployment catheter has been used to deploy an anchor that is fixedly coupled to a tether, one or more secondary anchor deployment catheters may be used to deploy one or more additional anchors over the tether. The additional anchors may, for example, be slidably deployed over the tether.

Figure 6B:
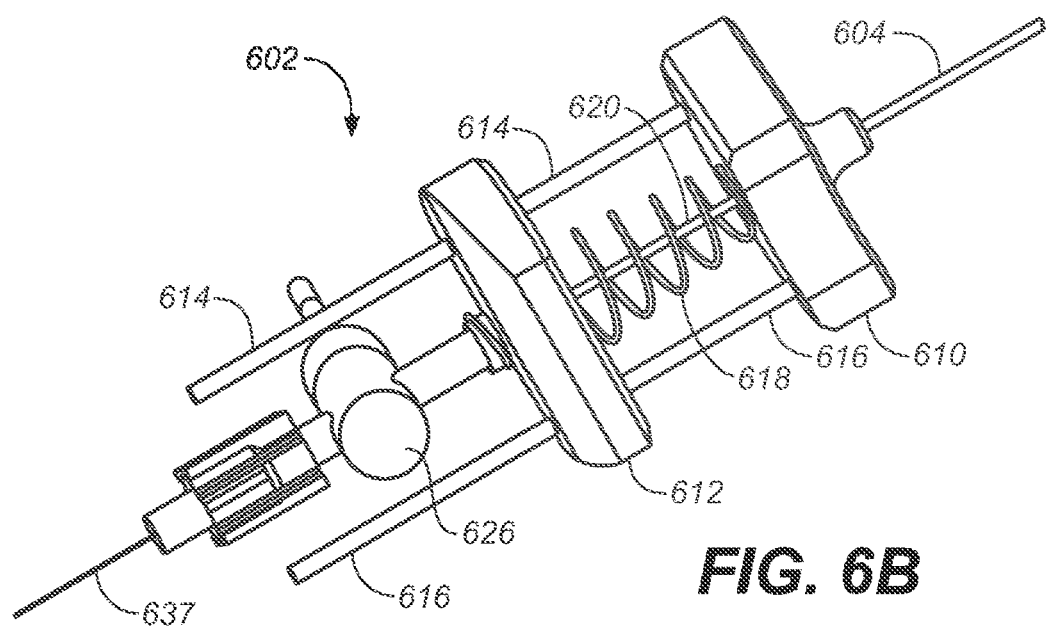
FIG. 6B is an enlarged view of region 6B of FIG. 6A.

FIGS. 6A-6N provide an illustrative depiction of a variation of a secondary anchor deployment catheter (600). First, and referring specifically to FIGS. 6A-6I, secondary anchor deployment catheter (600) comprises a proximal operating portion (602) and an elongated shaft (604) including a distal anchor deployment portion (606). Shaft (604) defines a lumen (608) (FIG. 6E), and a mechanism for deploying an anchor distally from the lumen, described in further detail below.

Referring now to FIGS. 6B-6D, 6J, and 6K, proximal operating portion (602), which may be used to deploy one or more anchors from secondary anchor deployment catheter (600), comprises a handle collar (610) and an actuator (612). Handle collar (610) is fixedly coupled to two slide pins (614) and (616), and actuator (612) is slidably coupled to the slide pins. A compression spring (618) is disposed between handle collar (610) and actuator (612). Compression spring (618) is coaxially disposed about a pushing member (620) that is fixedly coupled to actuator (612) and slidably disposed within an aperture (622) (FIG. 6C) of handle collar (610). It should be noted that features described above with respect to compression spring (518), such as the spring constant, may also be applied to compression spring (618), as appropriate. Pushing member (620), actuator (612), and compression spring (618) may be formed as a single integral unit, or may be formed of at least two parts that are then interconnected.

Pushing member (620) passes through a sheath (624) of shaft (604) (FIG. 6L), to distal anchor deployment portion (606) of shaft (604). As shown in FIG. 6E, pushing member (620) comprises a tapered distal tip portion (621) that may be advanced into a tubular internal stop (632) located in lumen (608) of secondary anchor deployment catheter (600). Internal stop (632) prevents over-advancement of the pushing member during deployment, as described above with reference to primary anchor deployment catheter (500). It should be noted that while a tapered distal tip portion is described, other variations of secondary anchor deployment catheters may comprise pushing members with different configurations, such as one or more of the pushing members described above with reference to FIGS. 5M-5R. Internal stop (632) comprises notches (697) (FIG. 6F) that help to hold an anchor (e.g., anchor (636), as shown) in place prior to deployment.

Pushing member (620) is tubular and comprises a liner (640) (FIG. 6L). Liner (640) may, for example, be made of one or more materials that enhance the slidability of the pushing member over a coupling member. In some variations, pushing member (620) may be in the form of a laser-cut hypotube, although other suitable variations may alternatively be used. A retrieval tether (637) (FIG. 6L) passes through pushing member (620), and will be described in additional detail below. While one variation of a pushing member has been described, other variations of pushing members may be used in secondary anchor deployment catheters, as appropriate.

During an anchor deployment procedure, a tether may be threaded into lumen (608) of shaft (604), and may be coupled to an anchor (e.g., anchor (636), shown in FIGS. 6E-6I and 6N). For example, the tether may be coupled to the anchor by being threaded through an eyelet of the anchor. In some variations, a tether may be threaded through a relatively small portion of lumen (608) of shaft (604). As an example, in certain variations, a tether may be threaded only through a portion of lumen (608) in distal anchor deployment portion (606). For example, FIG. 6O shows a tether (660) threaded through openings (662) and (664) in distal anchor deployment portion (606). Tether (660) crosses a short section of lumen (608), passing through the eyelet of anchor (636). Of course, the routing shown in FIG. 6O is only one variation of a tether routing, and tethers may be routed through a catheter in any appropriate manner.

After the tether has been coupled to the anchor, the anchor may be deployed over the tether. An operator may depress actuator (612), thereby causing compression of compression spring (618) and slidable movement of pushing member (620) axially within lumen (608) of shaft (604). This allows pushing member (620) to contact anchor (636) and push the anchor out of the lumen, thereby deploying the anchor into a target site. Internal stop (632) prevents pushing member (620) from being pushed too far distally. Thus, the pushing member may be pushed a sufficient amount to deploy anchor (636), without being pushed out of shaft (604). In some variations, internal stop (632) may be radiopaque. This may, for example, allow internal stop (632) to be aligned with a corresponding radiopaque band or marker on a guide tunnel when secondary anchor deployment catheter (600) is being advanced through the guide tunnel. Such alignment may be used to control the advancement of the secondary anchor deployment catheter through the guide tunnel.

Referring now to FIGS. 6A, 6E-6I, 6M, and 6N, distal anchor deployment portion (606) of shaft (604) is the location from which one or more anchors may be deployed. As shown, distal anchor deployment portion (606) includes a curved region (628) (FIG. 6A). Curved region (628) forms an arc that may have any suitable or desirable central angle. For example, the central angle may be from about 15 degrees to about 270 degrees, from about 45 degrees to about 1.80 degrees, or from about 50 degrees to about 120 degrees. As also depicted in FIG. 6E, distal anchor deployment portion (606) includes an inflection point (699). The curved region and inflection point may allow for enhanced positioning of the anchor deployment portion. Of course, while not shown, a secondary anchor deployment catheter or another type of catheter may also comprise more than one curved region and/or inflection point, or may not comprise any curved regions or inflection points. The curved region(s) and/or inflection point(s) in a catheter may be located in any appropriate region of the catheter.

Distal anchor deployment portion (606) includes sheath (624) and internal stop (632), and also comprises the distal tip (634) of secondary anchor deployment catheter (600). Additionally, and as shown, distal anchor deployment portion (606) may comprise a spiral-cut tubular member (630) disposed within sheath (624). Spiral-cut tubular member (630) may help to limit or prevent kinking in distal anchor deployment portion (606), and may be formed of, for example, one or more metal alloys, such as stainless steel. While a spiral-cut tubular member is shown, in some variations, a tubular member having a different configuration may be used. As an example, a tubular member having a sawtooth cut may be used. As another example, reinforcement rings (e.g., that are transverse to a longitudinal axis of the distal anchor deployment portion) and/or longitudinal reinforcement wires and/or ribbon may be used. As a further example, in some variations, a distal anchor deployment portion may comprise a tubular member with transverse slits. Additionally, it should be noted that while spiral-cut tubular member (630) is depicted as a component of secondary anchor deployment catheter (600), other types of catheters may include a spiral-cut tubular member or similar feature, as appropriate.

As depicted in FIGS. 6E-6I and 6N, anchor (636) has been loaded into lumen (608) of shaft (604), such that it is positioned within spiral-cut tubular member (630). Spiral-cut tubular member (630) may, for example, provide protection to anchor (636) prior to deployment. A tether may then be slidably coupled to anchor (636), as described above. Additionally, retrieval tether (637) is coupled to anchor (636), and extends proximally through secondary anchor deployment catheter (600), exiting at the proximal end of proximal operating portion (602). As shown, the retrieval tether is looped through an eyelet of the anchor. Retrieval tether (637) may be used, for example, to retrieve anchor (636) if anchor (636) has been deployed incorrectly (e.g., to a non-target site). More specifically, pulling the two strands of the retrieval tether proximally may cause the anchor to be pulled proximally, as well, and to thereby re-enter the lumen of the secondary anchor deployment catheter. The retrieval tether is also, of course, capable of being disengaged from the anchor after appropriate placement of the anchor. In some variations, the retrieval tether may be disengaged from the anchor by pulling on a proximal end of a single strand of the retrieval tether and withdrawing the retrieval tether from the anchor eyelet and the catheter. Retrieval tether (637) may be formed of any of the coupling member materials described herein, as appropriate. Furthermore, while a secondary anchor deployment catheter including a single retrieval tether has been described, in some variations, a secondary anchor deployment catheter may include multiple retrieval tethers, or may not include a retrieval tether at all Additional anchor retrieval mechanisms are described below.

Figure 6C:
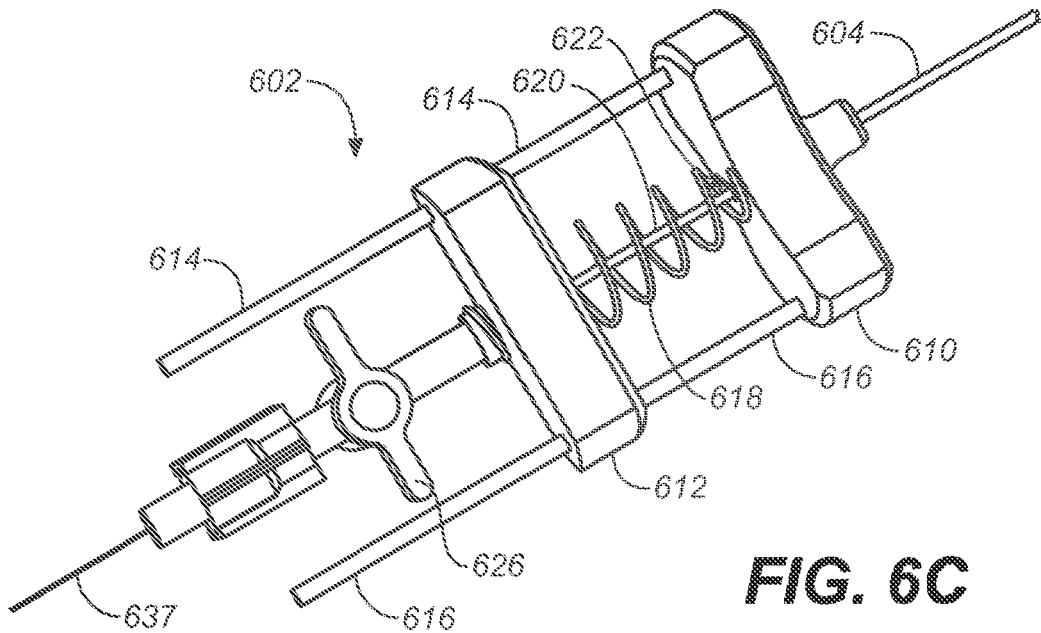
FIGS. 6C and 6D depict the enlarged view of FIG. 6B after it has been rotated.
Figure 6D:
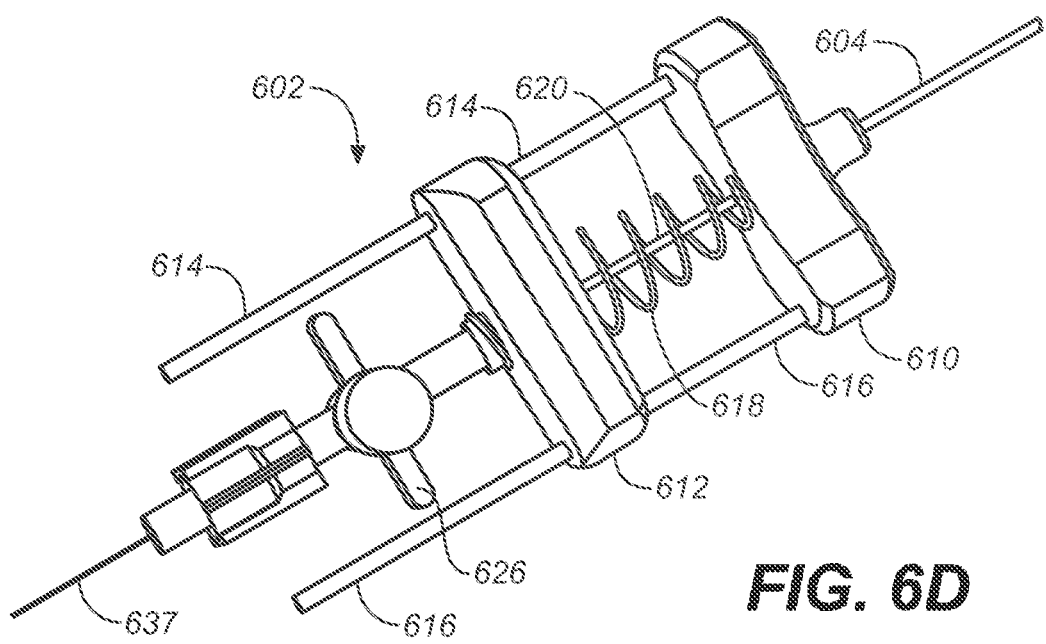
Figure 6E:
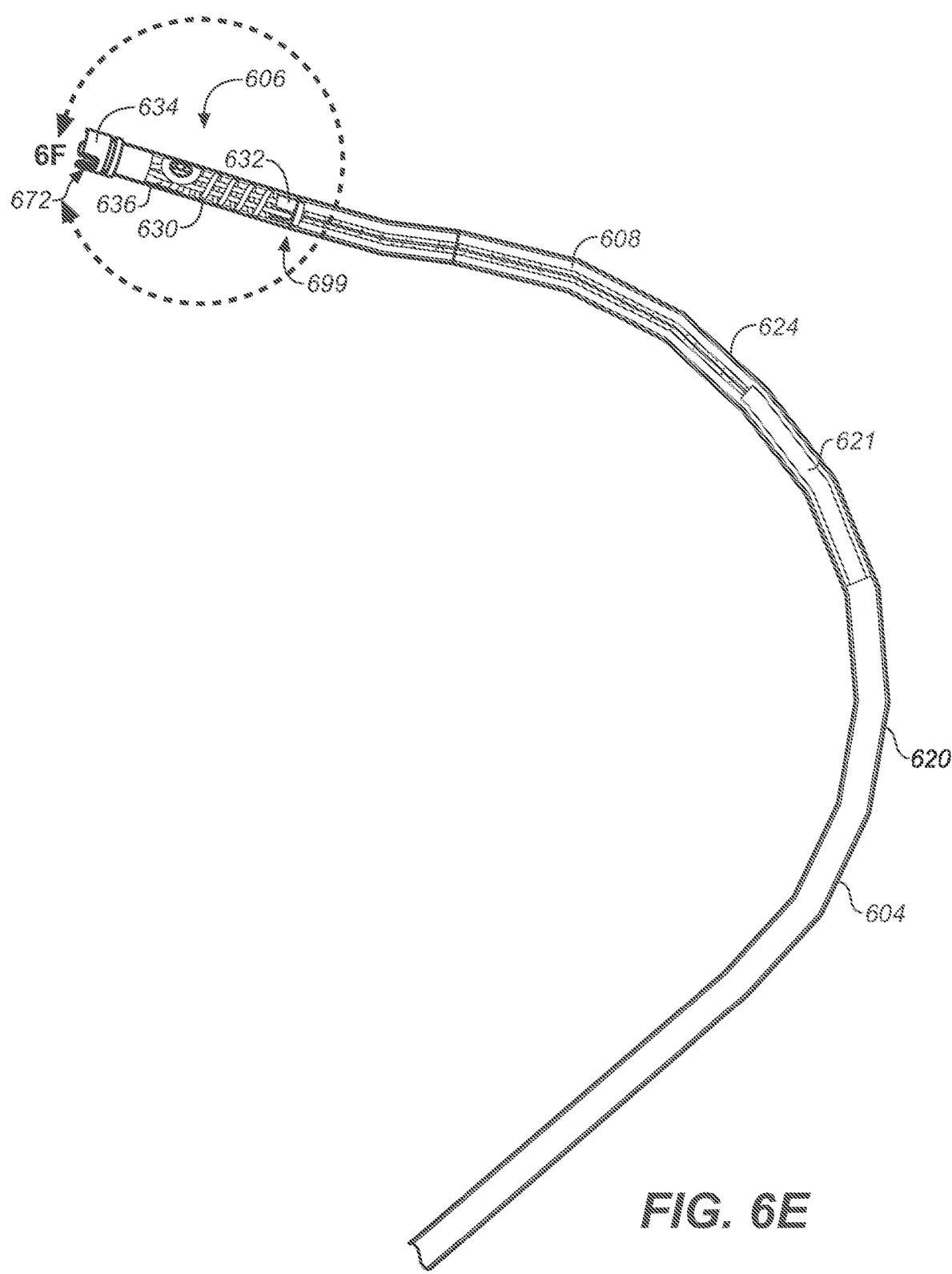
FIG. 6E is an enlarged view of region GE of FIG. 6A.
Figure 6G:
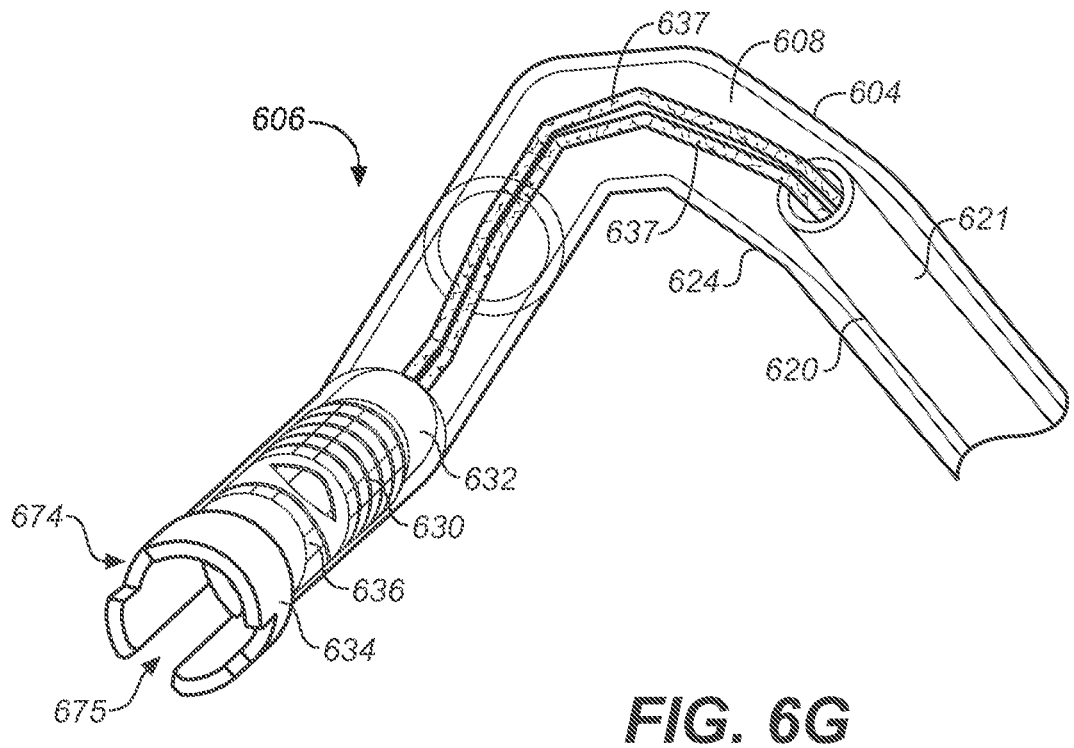
FIGS. 6G-6I are different perspective views of a distal portion of the anchor deployment device of FIG. 6A.
Figure 6H:
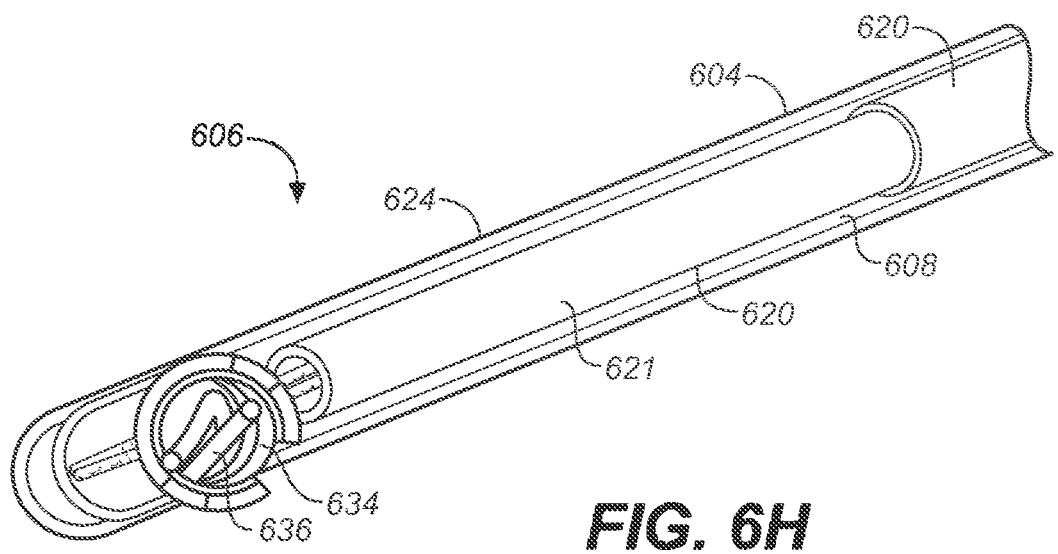
Figure 6I:
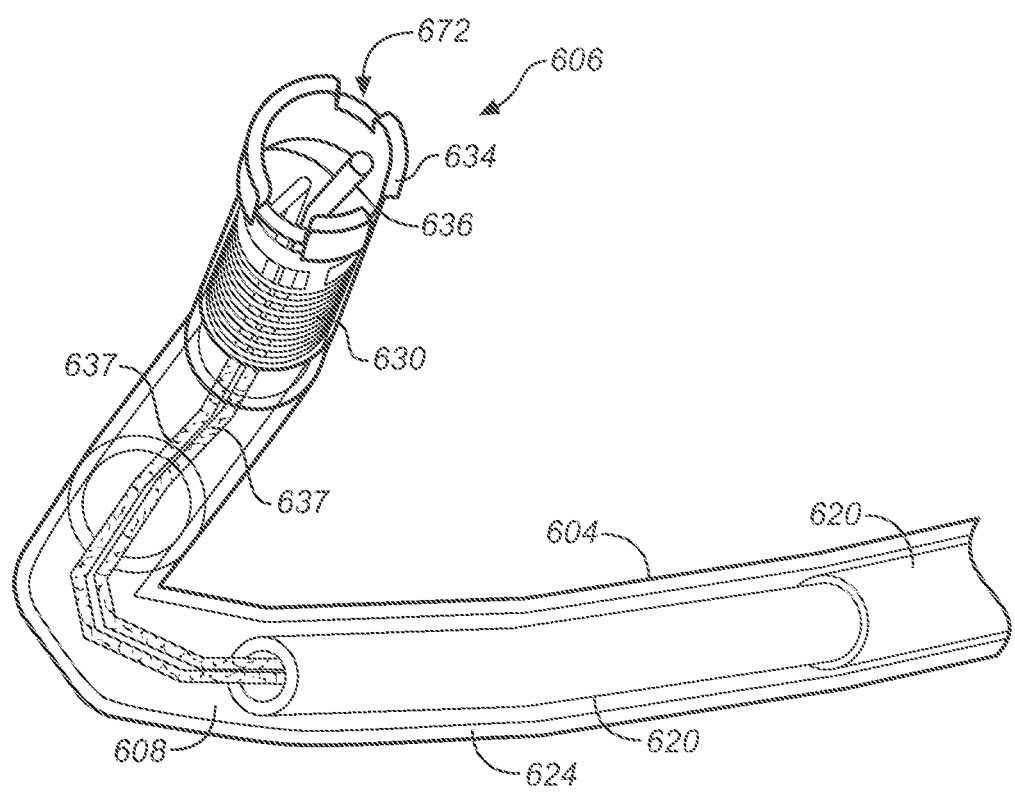

As shown in FIGS. 6B-6D, proximal operating portion (602) of secondary anchor deployment catheter (600) comprises a locking mechanism (626) that may be used to tension retrieval tether (637). This may, for example, limit the likelihood of retrieval tether (637) experiencing undesirable bunching and/or excessive slackness during use of secondary anchor deployment catheter (600). Locking mechanism (626) may be adjusted either to apply tension to retrieval tether (637), or not to apply tension to retrieval tether (637). While secondary anchor deployment catheter (600) includes locking mechanism (626), in some variations, a secondary anchor deployment catheter may alternatively or additionally include one or more other tether-tensioning components (e.g., an O-ring). Moreover, in certain variations, a primary anchor deployment catheter or another type of catheter may include a locking mechanism. In some variations, a catheter, such as an anchor deployment catheter, may not include any tether-tensioning components.

Referring now to FIGS. 6E-6I and 6N, distal tip (634) of distal anchor deployment portion (606) includes notches (672) and (674), as well as a tether-routing slot (675). Notches (672) and (674), and/or tether-routing slot (675), may, for example, be cut (e.g., laser-cut) or molded into the distal tip. Moreover, while two notches are shown, some variations of catheters may comprise just one notch or more than two notches, or may not comprise any notches. Similarly, certain variations of catheters may comprise more than one tether-routing slot, or may not comprise any tether-routing slots. Additionally, notches and tether-routing slots or other openings may have different shapes from those shown, and the notches or tether-routing slots on a catheter may all have the same shape, or may have different shapes.

Notches (672) and (674) may be used, for example, to help align and orient anchor (636) during deployment and/or for retrieval. For example, immediately after anchor (636) has been deployed from distal anchor deployment portion (606), the proximal portion of anchor (636) may be seated in notches (672) and (674). The operator may then choose to withdraw the catheter, thereby leaving the anchor behind or, if the anchor has been deployed incorrectly (e.g., to a non-target site), the operator may withdraw the anchor back into the catheter (e.g., using the retrieval tether). The positioning of the proximal portion of the anchor in the notches of the distal tip may make it relatively easy to withdraw the anchor back into the catheter. Moreover, the positioning of the proximal portion of the anchor in the notches may help to maintain a desired orientation and alignment of the anchor for future re-deployment.

Tether-routing slot (675) may be used, for example, to help load and position a tether within secondary anchor deployment catheter (600) (e.g., so that the tether can be coupled to an anchor within the catheter, such as anchor (636)).

Figure 6J:
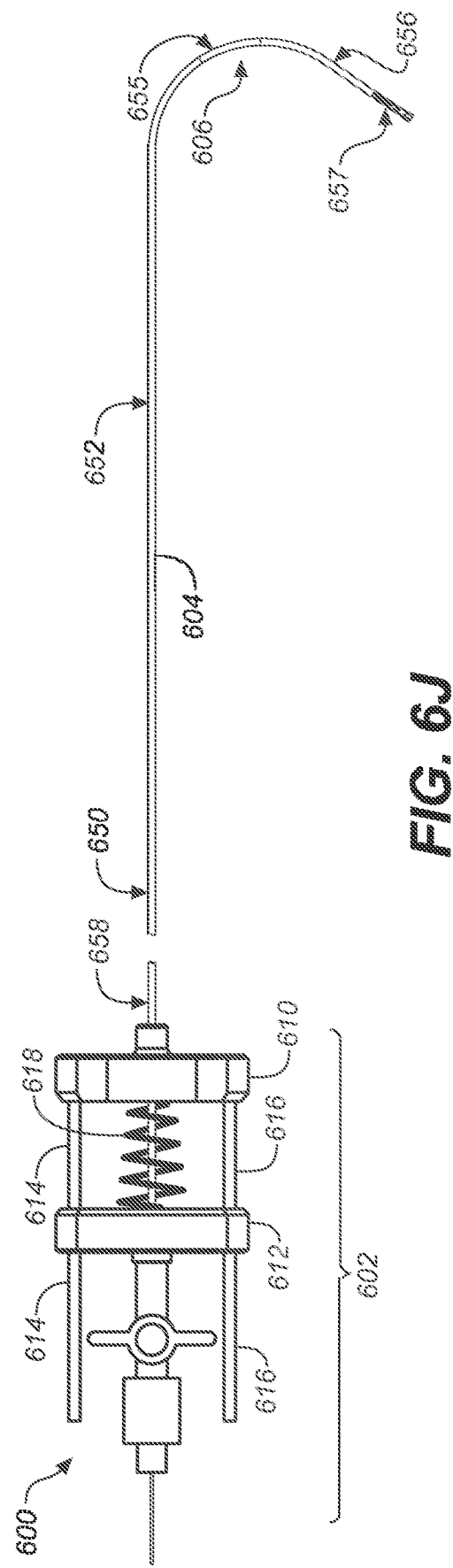
Figure 60:
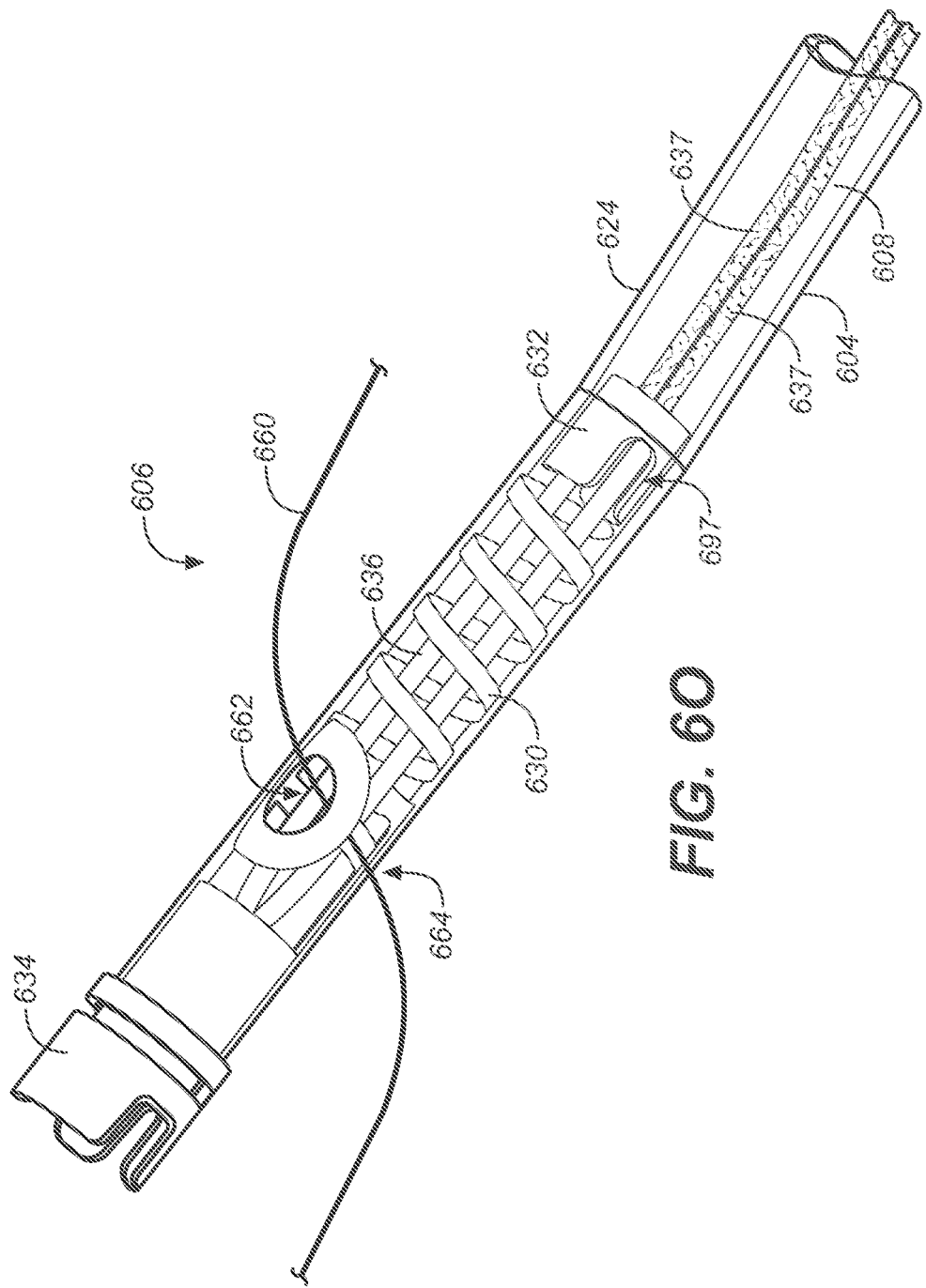

Referring specifically now to FIG. 6J, shaft (604) of secondary anchor deployment catheter (600) generally has a length selected for accessing the desired target site, and includes a proximal shaft region (650), a mid-shaft region (652), a first intermediate shaft region (655), a second intermediate shaft region (656), and a distal shaft region (657). In some variations, proximal shaft region (650) may be relatively long (e.g., depending on the application). In certain variations (e.g., certain variations in which secondary anchor deployment catheter (600) has to traverse a relatively long path to reach a target site), proximal shaft region (650) may have an extended length of about 100 centimeters to about 145 centimeters (e.g., about 110 centimeters to about 125 centimeters, such as about 118 centimeters). In some variations (e.g., some variations in which secondary anchor deployment catheter (600) has to traverse a shorter path to reach a target site, such as certain variations in which the secondary anchor deployment catheter enters the body via the groin), proximal shaft region (650) may have an extended length of about 10 centimeters to about 40 centimeters (e.g., about 20 centimeters to about 30 centimeters, such as about 25 centimeters).

In some variations, mid-shaft region (652) may have an extended length of about 5 centimeters to about 30 centimeters (e.g., about 10 centimeters to about 25 centimeters, such as about 17 centimeters), first intermediate shaft region (655) may have an extended length of about 3 centimeters to about 10 centimeters (e.g., about 3 centimeters to about 7 centimeters, such as about 5 centimeters), second intermediate shaft region (656) may have an extended length of about 1 centimeter to about 5 centimeters (e.g., about 1 centimeter to about 3 centimeters, such as about 2 centimeters), and/or distal shaft region (657) may have an extended length of about 1 millimeter to about 10 millimeters (e.g., about 1 millimeter to about 6 millimeters, such as about 3 millimeters).

Each of the regions of shaft (604) shown in FIG. 6J may be formed of the same material or materials, or some or all of the regions may be formed of different materials. For example, it may be desirable for a more proximal region (e.g., proximal shaft region (650)) to be formed of one or more relatively stiff materials (e.g., for enhanced pushability), while a more distal region (e.g., second intermediate shaft region (656) and/or distal shaft region (657)) is formed of one or more relatively flexible materials (e.g., for maneuverability). Examples of materials which may be suitable for any or all of these regions include those provided above with reference to primary anchor deployment catheter (500), as well as any other appropriate materials.

As shown in FIG. 6J, shaft (604) also comprises a strain relief region (658). Strain relief region (658) may, for example, have one or more of the features and/or advantages of strain relief region (558) of primary anchor deployment catheter (500), described above.

As described above, in some variations, the shaft of an anchor deployment catheter may be relatively flexible (e.g., for use in percutaneous procedures). In some cases in which an anchor deployment catheter is intended for use in percutaneous procedures, the anchor deployment catheter may comprise a shaft that is longer than it would be in cases in which an anchor deployment catheter is intended for use in surgical procedures. Any suitable material or materials may be used to construct a catheter shaft to render the shaft relatively flexible. For example, the flexible shaft may be made of one or more polymers (e.g., nylon, polyethylene, polyetheretherketone (PEEK), polyether block amides, polytetrafluoroethylene (PTFE), fluorinated ethylene propylene copolymer), one or more polymer blends (e.g., nylon blends), one or more metal alloys (e.g., nickel titanium alloys, stainless steel), or combinations thereof.

As described above, in some variations, an anchor deployment catheter may comprise one or more relatively rigid materials. Such a device may be particularly useful, for example, in surgical applications, where an incision is used to access the site for anchor deployment. Any suitable rigid material or materials may be used. For example, the catheter may comprise a shaft that is made from one or more metal alloys (e.g., stainless steel, nickel titanium alloys), one or more polymer composites (e.g., carbon-filled nylon, carbon-filled polyetheretherketone), one or more polymers (e.g., polypropylene, high density polyethylene), or combinations thereof.

While secondary anchor deployment catheter (600) is depicted as having a certain configuration, it should be noted that other secondary anchor deployment catheters may have different configurations depending, for example, on the characteristics of the target site and/or the preferences of the operator.

As discussed above, certain variations of anchor deployment catheters may comprise shafts having one or more curves. The curve or curves in a catheter shaft may be used, for example, to help properly position and align the catheter shaft at a particular target site. In some variations, a region of the shaft that is distal to a curve in the shaft may define the same plane as a region of the shaft that is proximal to the curve, or may even define the same plane as the rest of the shaft. In certain variations, however, a device may comprise a shaft having a curve, and a region of the shaft that is distal to the curve may define a plane that is different from a plane defined by a region of the shaft that is proximal to the curve. The planes may be angled relative to each other.

Figure 7A:
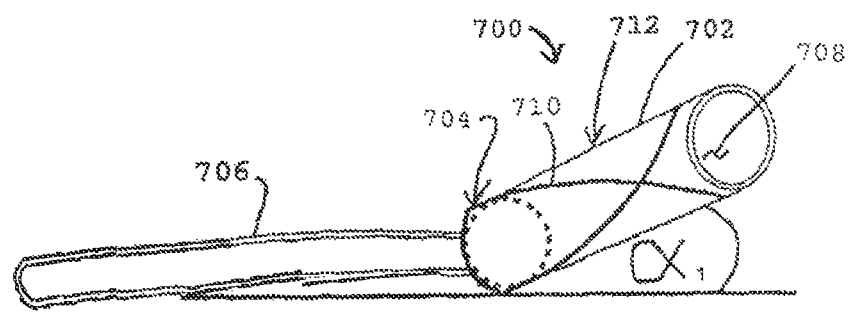
FIG. 7A is an illustrative depiction of a front view of a variation of an anchor deployment device.

For example, FIG. 7A shows a primary anchor deployment catheter (700) comprising an elongated shaft (702) comprising a lumen (708). Elongated shaft (702) has a curve (704) and includes a region (712) that is distal to the curve and a region (714) (FIG. 7B) that is proximal to the curve. As shown in FIG. 7A, primary anchor deployment catheter (700) also comprises an external stop (706), as well as an anchor (710) disposed within lumen (708) in region (712) of elongated shaft (702).

Figure 7B:
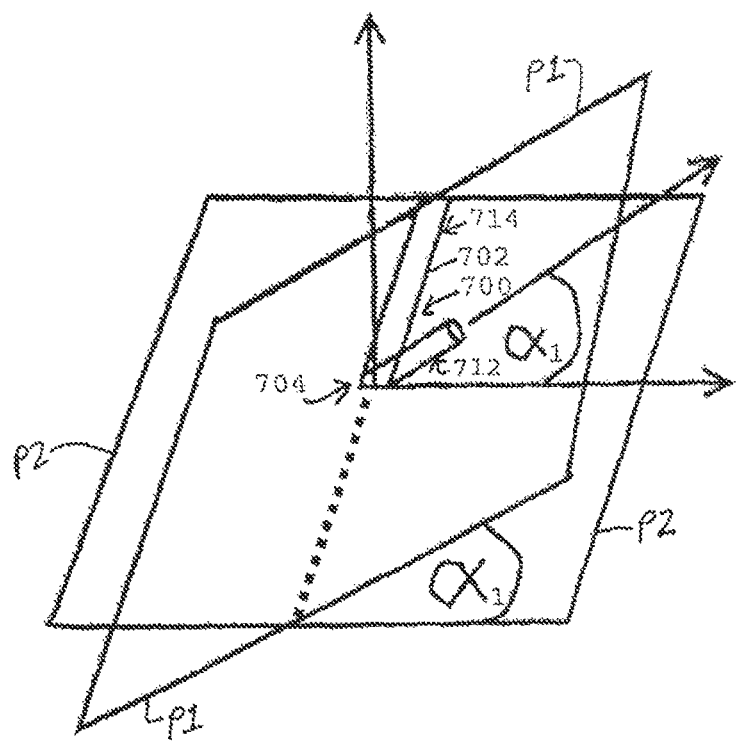
FIG. 7B is schematic illustration of the geometry of the anchor deployment device of FIG. 7A.

As shown both in FIGS. 7A and 7B, region (712) of elongated shaft (702) defines a plane (P1), and region (714) of elongated shaft (702) defines a different plane (P2). The planes have an angle ($\alpha_1$) therebetween. In some variations, angle ($\alpha_1$) may be from about 10 degrees to about 90 degrees (e.g., about 20 degrees to about 80 degrees, about 30 degrees to about 75 degrees, about 40 degrees to about 70 degrees, about 40 degrees to about 60 degrees, about 50 degrees to about 70 degrees, or about 50 degrees to about 60 degrees). For example, in certain variations, angle ($\alpha_1$) may be about 60 degrees.

Figure 7C:
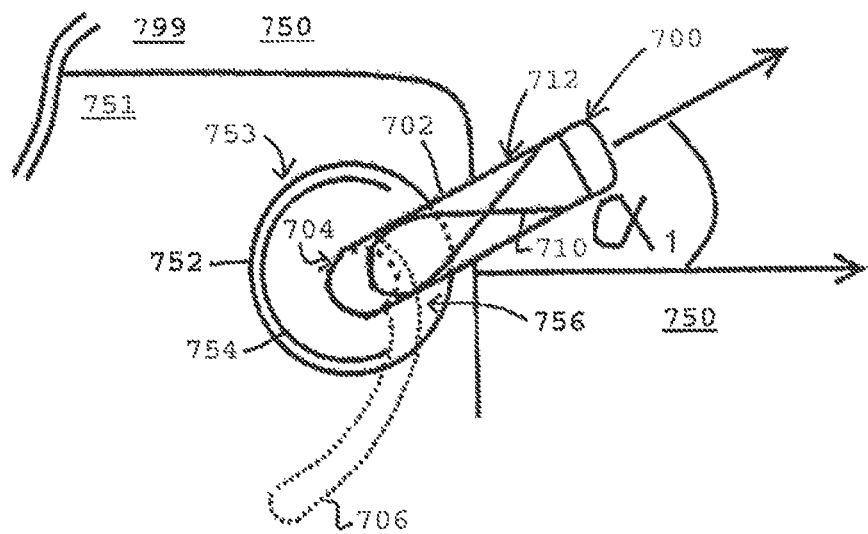
FIG. 7C is an illustrative depiction of a variation of a method of using the anchor deployment device of FIG. 7A in heart tissue of a subject.

Angle ($\alpha_1$) may be selected, for example, to help with the positioning and alignment of region (714) of elongated shaft (702) at a target site. For example, FIG. 7C is an illustrative depiction of primary anchor deployment catheter (700) being positioned to deploy an anchor into heart tissue. As shown there, a guide tunnel (753) is positioned within a subvalvular space (751) of a left ventricle of a heart, below a mitral valve (799). Guide tunnel (753) comprises an outer catheter (752) and an inner catheter (754) located within a lumen of the outer catheter. Primary anchor deployment catheter (700) is positioned within a lumen of inner catheter (754), and region (712) is advanced through a window region (756) of guide tunnel (753) and embedded into heart tissue (750). Primary anchor deployment catheter (700) may then be used to deploy anchor (710) into mitral valve tissue (750). Angle ($\alpha_1$) between regions (712) and (714) of shaft (702) of primary anchor deployment catheter (700) may, for example, help an operator to relatively easily deploy anchor (710) into the desired target site and at the desired location.

Figure 8A:
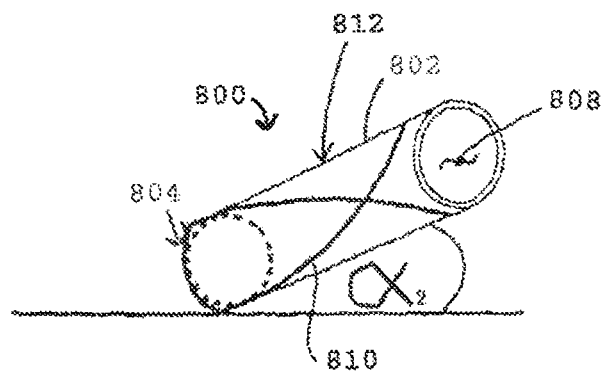
FIG. 8A is an illustrative depiction of a front view of another variation of an anchor deployment device.

Of course, other types of catheters and indeed, other types of devices, may include regions defining planes that are angled with respect to each other. For example, FIG. 8A shows a secondary anchor deployment catheter (800) comprising an elongated shaft (802) comprising a lumen (808). Elongated shaft (802) has a curve (804) and includes a region (812) that is distal to the curve and a region (814) (FIG. 8B) that is proximal to the curve. As shown in FIG. 8A, secondary anchor deployment catheter (800) also comprises an anchor (810) disposed within lumen (808) in region (812) of elongated shaft (802).

Figure 8B:
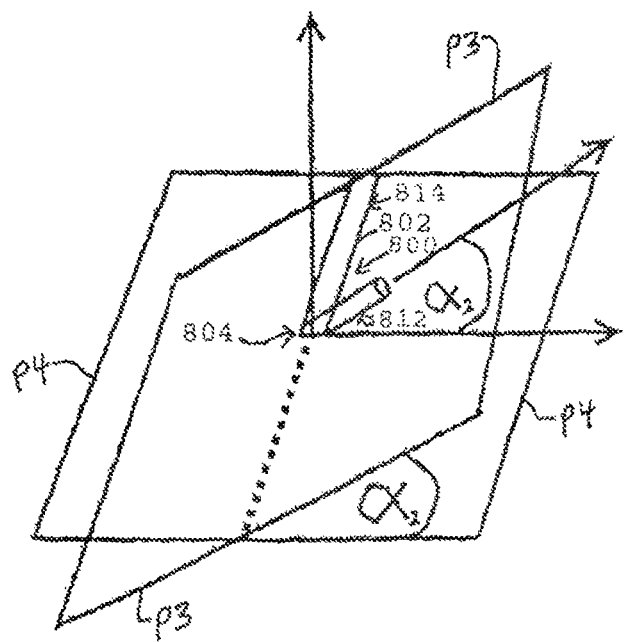
FIG. 8B is schematic illustration of the geometry of the anchor deployment device of FIG. 8A.

As shown both in FIGS. 8A and 8B, region (812) of elongated shaft (802) defines a plane (P3), and region (814) of elongated shaft (802) defines a different plane (P4). The planes have an angle ($\alpha_2$) therebetween. In some variations, angle ($\alpha_2$) may be from about 10 degrees to about 90 degrees (e.g., about 20 degrees to about 80 degrees, about 30 degrees to about 75 degrees, about 40 degrees to about 70 degrees, or about 50 degrees to about 60 degrees) For example, in certain variations, angle ($\alpha_2$) may be about 50 degrees.

Figure 8C:
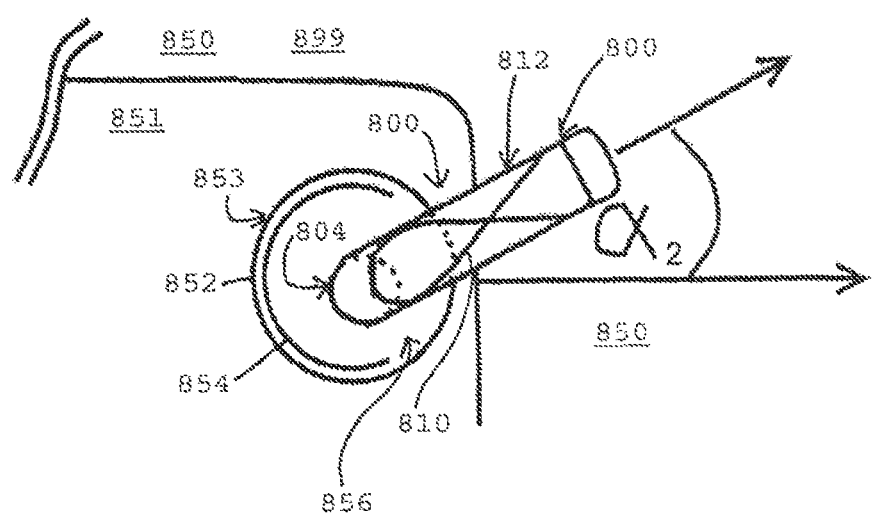
FIG. 8C is an illustrative depiction of a variation of a method of using the anchor deployment device of FIG. 8A in heart tissue of a subject.

Angle ($\alpha_2$) may be selected, for example, to help with the positioning and alignment of region (814) of elongated shaft (802) at a target site. For example, FIG. 8C is an illustrative depiction of secondary anchor deployment catheter (800) being positioned to deploy an anchor into heart tissue. As shown there, a guide tunnel (853) is positioned within a subvalvular space (851) of a left ventricle of a heart, below a mitral valve (899), Guide tunnel (853) comprises an outer catheter (852) and an inner catheter (854) located within a lumen of the outer catheter. Secondary anchor deployment catheter (800) is positioned within a lumen of inner catheter (854), and region (812) is advanced through a window region (856) of guide tunnel (853) and embedded into heart tissue (850). Secondary anchor deployment catheter (800) may then be used to deploy anchor (810) into mitral valve tissue (850). Angle ($\alpha_2$) between the planes defined by regions (812) and (814) of shaft (802) of secondary anchor deployment catheter (800) may, for example, help an operator to relatively easily deploy anchor (810) into the desired target site and at the desired location.

While anchor deployment catheters having one shaft have been described, some variations of anchor deployment catheters may comprise more than one shaft (e.g., two shafts, three shafts, etc.). In certain variations, the multiple shafts of an anchor deployment catheter may be used to deploy multiple anchors from the catheter simultaneously. Similarly, multiple anchors may be pre-loaded into a single catheter shaft and deployed therefrom, serially or sequentially. In a like manner, an anchor deployment catheter may also comprise an additional shaft, or an additional lumen within a single shaft, which may be configured to inflate a balloon. This may, for example, aid in the deployment of the tissue anchors as the inflation of the balloon presses the anchors against the tissue to provide greater apposition. The balloon may be made from any appropriate material, such as nylon, polyethylene, polyurethane, or a combination (e.g., a mixture) thereof.

While certain variations of anchor deployment devices and methods have been described, other variations may also be employed to deploy one or more anchors at a target site. For example, as discussed above, in some variations, multiple (i.e., at least two) anchors may be housed within a single anchor deployment device, and may be deployed from the device at a target site.

Figure 9A:
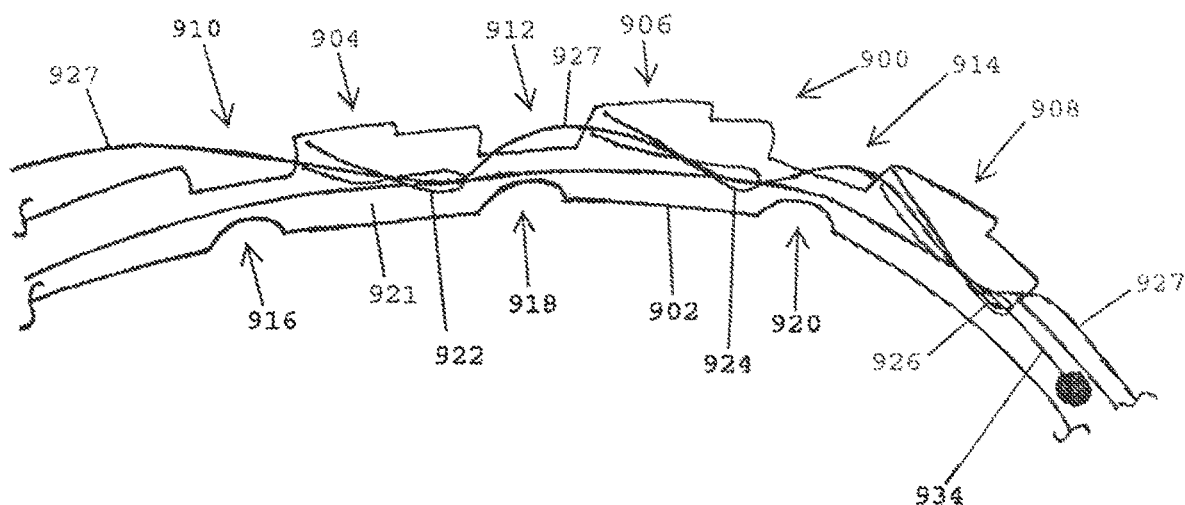
FIG. 9A is an illustrative side view of a variation of an anchor deployment device that may be used to deploy multiple anchors.

As an example, FIG. 9A is an illustrative depiction of a distal portion of an anchor deployment catheter (900) that may be used to house and deploy multiple anchors. During use, the anchors may be deployed from the side of the catheter. As shown in FIG. 9A, anchor deployment catheter (900) comprises an elongated member (902) comprising three anchor-housing segments (904), (906) and (908) and three flexible segments (910), (912) and (914), where each of the flexible segments comprises a notch (916), (918) or (920). While three anchor-housing segments and three flexible segments are shown, other variations of devices may have a different number of anchor-housing segments and/or flexible segments, as appropriate. Moreover, the number of anchor-housing segments may be different from the number of flexible segments.

Catheter (900) also includes a lumen (921) therethrough. While not shown, in some variations, a spine, such as a wire (e.g., a Nitinol wire that is 0.009 inch in cross-sectional diameter, or a 302/304 stainless steel wire that is 0.005 inch in cross-sectional diameter) may be disposed within lumen (921). In some such variations, the spine may help to control the catheter's orientation during use (e.g., by biasing the catheter). This may, for example, allow the catheter to be curved and/or to track along a certain curvature during use. Anchor-housing segment (904) contains a collapsed anchor (922), anchor-housing segment (906) contains a collapsed anchor (924), and anchor-housing segment (908) contains a collapsed anchor (926). A tether (927) passes into and out of anchor deployment catheter (900), and is looped through the eyelets of each of anchors (922), (924) and (926). In some cases, tether (927) may be fixedly coupled to at least one of the anchors, such as distal-most anchor (926).

Figure 9B:
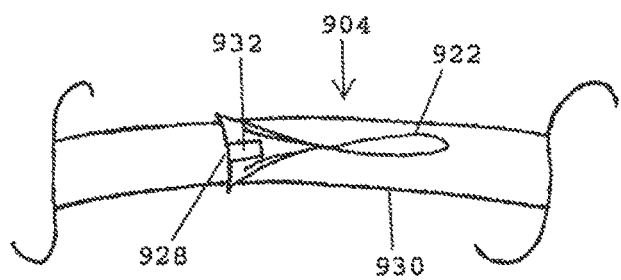
FIG. 9B is an illustrative top view of a portion of the anchor deployment device of FIG. 9A.

Referring now to FIG. 9B, a top view of anchor-housing segment (904) is depicted. As shown there, anchor-housing segment (904) comprises a protective shield (928) that may, for example, prevent anchor (922) from accidentally puncturing through the wall (930) of elongated member (902) at that location. However, shield (928) includes an aperture (as shown, a slit (932)) that allows for deployment of anchor (922) therethrough. While shield (928) includes only one aperture, some variations of shields may include multiple apertures. Moreover, certain variations of devices may not include any shields.

Figure 9C:
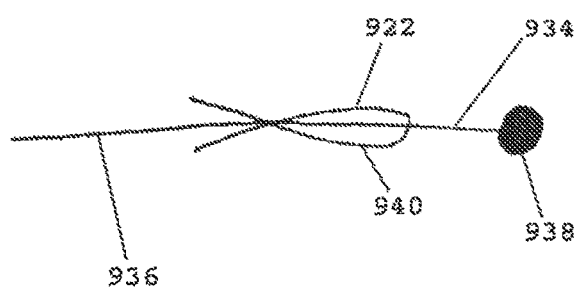
FIG. 9C is an illustrative depiction of a component of the anchor deployment device of FIG. 9A.

Referring additionally now to FIG. 9C, the anchors in anchor deployment catheter (900) may be deployed using a pulling member (934) comprising an elongated portion (936) and a bulbous portion (938) at one end of the elongated portion. Elongated portion (936) is looped through the eyelets of each of anchors (922), (924) and (926) (as shown, for example, with respect to eyelet (940) of anchor (922) in FIG. 9C). During use, an operator may pull on elongated portion (936), so that bulbous portion (938) contacts each anchor and forces it out through the corresponding aperture in the anchor deployment catheter (e.g., slit (932) in shield (928), for anchor (922)). In some variations, an aperture may be configured to direct anchor legs in an orientation that is relatively perpendicular to the target tissue surface during deployment. Tether (927) may also be released as the anchors are being released, or after the anchors have been released. In certain variations, anchor-housing segments (904), (906) and (908) may be configured for tether (927) to be released therethrough (e.g., the anchor-housing segments may be actuated to open like doors), Alternatively or additionally, tether (927) may be routed in a configuration (not shown) such that deployment of the anchors also results in deployment of the tether. As an example, tether (927) may be routed into each anchor-housing segment, through the eyelet of the anchor housed within the segment, and back out of the anchor-housing segment in the same location at which the tether entered the segment.

The presence of flexible segments (910), (912) and (914) may provide anchor deployment catheter (900) with flexibility during use, such that the anchor deployment catheter may, for example, be relatively easily advanced along a tortuous pathway. In some variations, flexible segments (910), (912) and (914) may be formed of one or more relatively flexible materials (e.g., GRILAMID® L-25 nylon 12 plastic), while anchor-housing segments (904), (906) and (908) are formed of relatively stiff materials (e.g., GRILAMID® TR 55 nylon 12 plastic). Additionally, the presence of the relatively stiff anchors within the anchor-housing segments may enhance the stiffness of those segments.

"Anchors," for the purposes of this application, are defined to mean any fasteners. The anchors may be made of any suitable material, may be any suitable size, and may be of any suitable shape. The size of an anchor may depend largely upon the end use of the anchor. For example, anchors to be used in the repair of cardiac valves generally will be much smaller in dimension than those anchors used to repair large wounds or to reduce the circumference of a large hollow body organ. The anchors may be made of one material or more than one material, such as one or more polymers (e.g., biodegradable polymers), metals, alloys, and/or combinations or mixtures thereof. The anchors may comprise C-shaped or semicircular hooks, curved hooks of other shapes, straight hooks, barbed hooks, single or multiple loop anchors, clips of any kind, T-tags, rivets, plication elements (e.g., local plication elements such as staples), non-plication elements, or any other suitable fastener(s). In one variation, anchors may comprise two tips that curve in opposite directions upon deployment, forming two intersecting semi-circles, circles, ovals, helices or the like. In some variations, the tips may be sharpened or beveled. Certain variations of anchors may comprise fibrous and/or porous materials in the shape of bars, rods or pledgets. In some cases, the fibrous or porous materials may expand in volume during use.

In certain variations, the anchors may be self-deforming. By "self-deforming," it is meant that the anchors are biased to change from a first undeployed shape to a second deployed shape upon release of the anchors from a restraint. Such self-deforming anchors may change shape as they are released from a housing or deployed from a lumen or opening to enter annular tissue, and secure themselves to the tissue. Self-deforming anchors may be made of any suitable material such as spring stainless steel, or super-elastic or shape-memory material such as nickel-titanium alloy (e.g., Nitinol). The anchors may be configured to self-expand and self-secure into tissue, but need not be configured in such a fashion.

In certain variations, anchors may comprise one or more bioactive agents, including biodegradable metals and polymers. In some variations, anchors may comprise electrode components. Such electrodes may, for example, sense various parameters including but not limited to impedance, temperature and electrical signals. In certain variations, such electrodes may be used to supply energy to tissue at ablation or sub-ablation amounts. Anchors are described, for example, in U.S. patent application Ser. No. 11/202,474 (published as US 2005/0273138 A1), which is hereby incorporated by reference in its entirety.

While anchors have been described, other types of implants may be used with the devices, methods, and kits described here, as appropriate. For example, an implant may include one or more leads or electrodes (e.g., pacing electrodes, diagnostic electrodes, active electrodes), In some variations, an implant may include a fabric implant or an annuloplasty ring, alone or in combination with one or more anchors. Additional examples of implants include implants that deliver therapy, such as drug-delivery implants, and implants that provide telemetry of information, such as information about a target site. For example, implants may be used to deliver growth factors and/or genetic regenerative factors. Other types of suitable implants may also be used.

Coupling members may be made from any suitable or desirable biocompatible material, and may be made of a single material or a combination of materials (e.g., a coupling member may be in the form of one long piece of material, or may comprise two or more pieces). Moreover, coupling members may be braided or not braided, woven or not woven, and/or reinforced and/or impregnated with one or more additional materials. As non-limiting examples, a coupling member may be made from (1) a suture material (e.g., absorbable suture materials such as polyglycolic acid and polydioxanone, natural fibers such as silk, and artificial fibers such as polypropylene, polytetrafluoroethylene (PTFE), polyester, polyester impregnated with polytetrafluoroethylene, nylon, a KEVLAR® brand fiber, a VECTRAN® brand fiber, etc.), (2) a suture-like material, (3) a metal (absorbable or non-absorbable), (4) a metal alloy (e.g., stainless steel), (5) a shape-memory material, such as a shape-memory alloy (e.g., a nickel titanium alloy), (6) other biocompatible material, or (7) any combination thereof. In some variations, a coupling member may be in the form of a DACRON® polyester strip. In certain variations, a coupling member may comprise polyethylene, such as high-density polyethylene (HDPE) or ultra-high molecular weight polyethylene (UHMWPE). Some variations of coupling members may have a braided textile construction (e.g., including a minimum of four strands on one side of a braid). In certain variations, free ends of the braid strands may be heat-fused together. Some variations of coupling members may be in the form of a wire, tether, thread, or string.

In certain variations, a coupling member may include multiple layers, and/or may include one or more coatings. For example, a coupling member may be in the form of a polymer-coated wire. In some variations, a coupling member may comprise a combination of one or more sutures and one or more wires. As an example, a coupling member may be formed of a suture that is braided with a wire. Certain variations of coupling members may be in the form of monofilament or multifilament textile yarns or fibers.

In some variations, a coupling member may be formed of one or more electrode materials. In certain variations, a coupling member may be formed of one or more materials that provide for the telemetry of information (e.g., regarding the condition of a target site).

While procedures for tightening or compressing tissue using one coupling member have been described, other procedures for modifying tissue may involve the use of multiple coupling members, such as 2, 3, 4, 5, or 10 coupling members. When multiple coupling members are used, at least some of the coupling members may be associated with (e.g., fixedly attached to) different anchors, and/or at least some of the coupling members may be associated with (e.g., fixedly attached to) the same anchor. The devices and methods described herein may apply to single coupling member procedures, or to multiple coupling member procedures.

Some variations of coupling members may include one or more therapeutic agents (e.g., drugs, such as time-release drugs). As an example, a coupling member may be partially or entirely coated with one or more therapeutic agents. In certain variations, a coupling member may be used to deliver one or more growth factors and/or genetic regenerative factors. In some variations, a coupling member may be coated with a material (e.g., a polymer) that encapsulates or controls the release rate of one or more therapeutic agents, or in which one or more therapeutic agents are embedded. The therapeutic agents may be used, for example, to treat a target site to which the coupling member is fixedly attached or otherwise secured. In certain variations, a coupling member may include one or more lumens through which one or more therapeutic agents may be delivered.

In some variations, a coupling member may be marked to help with proper placement. For example, in some procedures, it may be desirable for deployed anchors to be evenly spaced apart (e.g., 1 millimeter to 5 millimeters apart). In such procedures, the coupling member may be marked periodically to indicate to the operator where the next anchor should be deployed.

In addition to deploying anchors, some variations of the methods described here may comprise loading one or more anchors into an anchor deployment device, such as an anchor deployment catheter (e.g., prior to deploying the anchors). As an example, an anchor may be loaded within a lumen of a shaft of an anchor deployment catheter. In some variations, the anchor may be loaded through a distal opening in the anchor deployment catheter, such as an opening located at the distal end of the anchor deployment catheter. In certain variations, the anchor may comprise an eyelet, and the method may also comprise passing a coupling member into the lumen of the anchor deployment catheter, and through the eyelet of the anchor. In some variations, an anchor may be pre-coupled to a coupling member prior to being loaded into an anchor deployment device. Once the target site has been reached, the anchor may be deployed. It should be noted that an anchor may be loaded into a catheter at any point prior to deployment of the anchor. Thus, for example, in some variations, an anchor deployment catheter may be provided with one or more pre-loaded anchors therein, ready for deployment.

The manner in which an anchor is loaded into a device may depend, for example, on the particular configuration of the anchor used. In some variations, one or more anchors may be back-loaded into an anchor deployment catheter. That is, the anchors may be aligned and pulled and/or pushed into the distal tip of the catheter. In certain variations in which the anchors comprise at least two legs, the anchor legs may be aligned parallel to the shaft so that the tips of the anchor legs are flush with the tip of the catheter. A loading tool (e.g., a lasso) may be useful in this respect.

In some variations, a distal anchor deployment portion of an anchor deployment catheter may have one or more slots therethrough. In this way, one or more anchors may be loaded through the slot or slots and compressed into the lumen of the shaft. As described above, a slot or slots may also be useful in allowing a coupling member to pass therethrough and through the eyelet(s) of the anchor(s).

After an anchor has been loaded into an anchor deployment catheter, a coupling member may be passed into the shaft of the catheter and through the eyelet of the anchor, as described above. Typically, this may occur with a secondary anchor deployment catheter, since a primary anchor deployment catheter generally includes an anchor that is fixedly coupled to a coupling member, and that is loaded into the primary anchor deployment catheter together with the coupling member. However, in some variations, a coupling member may be coupled to an anchor after the anchor has already been loaded into a primary anchor deployment catheter. Methods for threading a coupling member into a catheter, such as a primary anchor deployment catheter or a secondary anchor deployment catheter (e.g., after an anchor has been loaded into the catheter) are provided below.

Figures 10A, 10B:
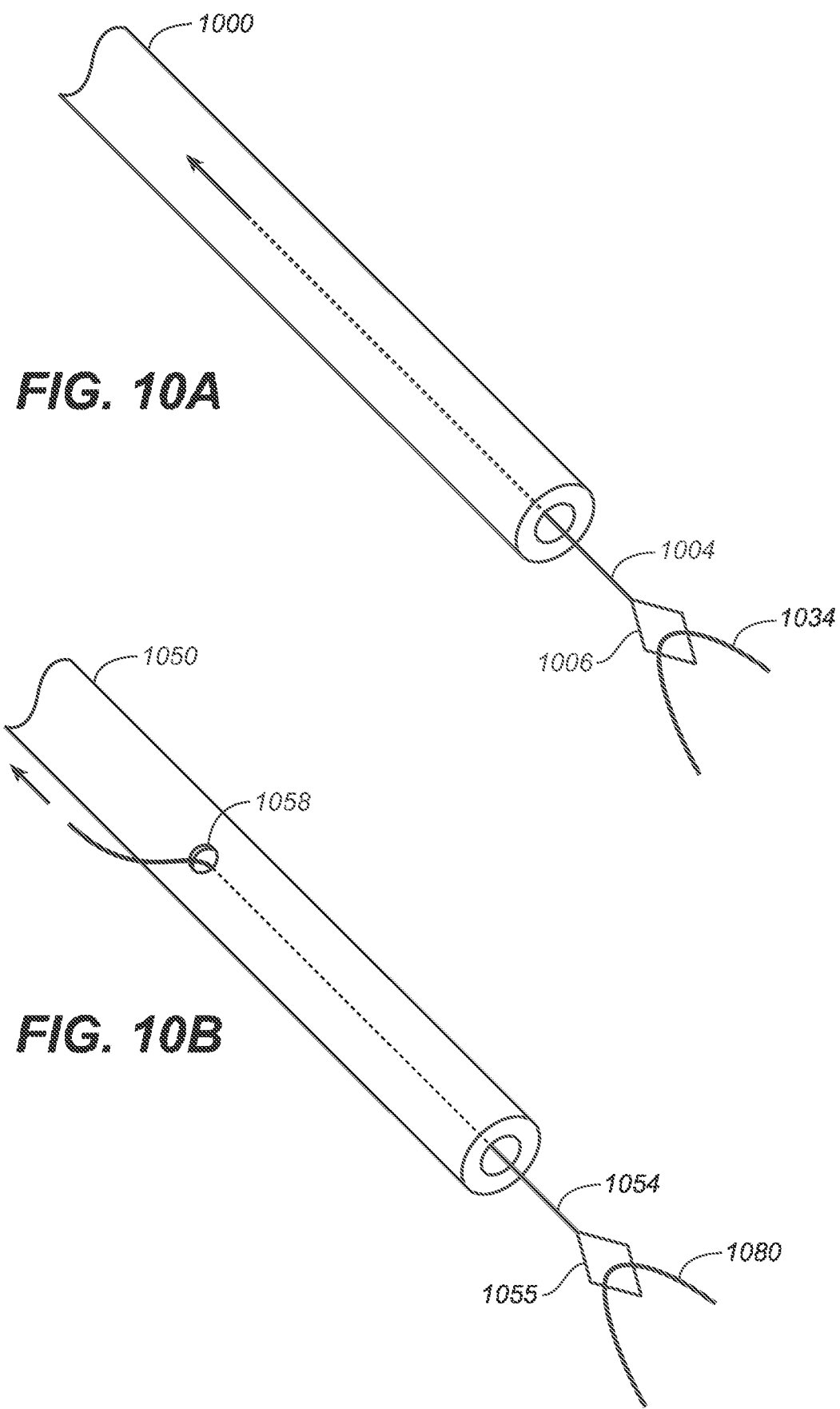
FIGS. 10A and 10B are illustrative variations of devices for loading tethers into devices or device components, such as catheters.

Any of a number of different variations of methods may be used to load a coupling member into a catheter. For example, FIGS. 10A and 10B depict exemplary variations of lassos that may be used to load a coupling member (e.g., a tether) into a device, such as an anchor deployment catheter. As shown there, in some variations, a tether (1034) may be loaded into a device (1000) using a lasso (1004) comprising a loop (1006) at one end. First, one end of tether (1034) may be threaded through loop (1006) of lasso (1004). Lasso (1004) may then be pulled along the longitudinal axis of device (1000) (FIG. 10A), to load tether (1034) into device (1000). In alternative implementations, shown in FIG. 10B, a lasso (1054) having a loop (1055) may be pulled through a side hole (1058) in a device (1050) to load a tether (1080) into the device. Lassos may be made from, for example, conventional materials such as wire, suture, cable, string, or a monofilament. A lasso may comprise a loop (as show in FIGS. 10A and 10B), a hook, a coil, a tube, an elongate element with a hole, or any other structure or material that can "grab" a tether.

Figure 11A:
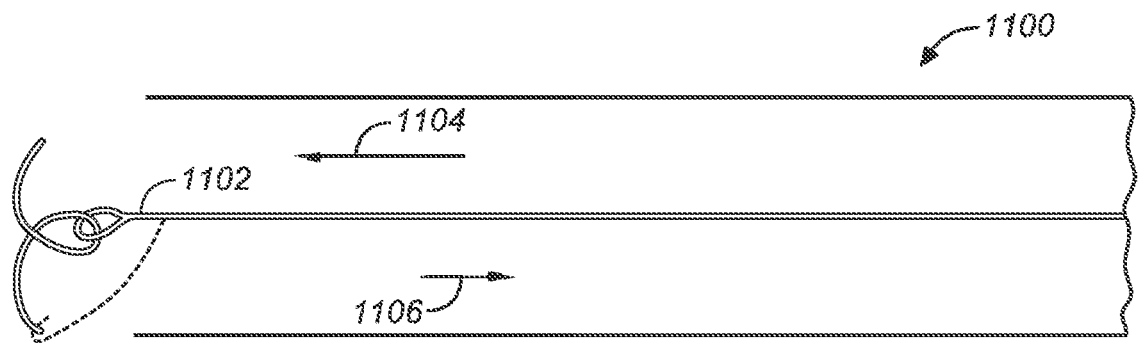
FIGS. 11A and 11B depict exemplary illustrations of variations of anchor retrieval mechanisms and methods.

As described above, some variations of methods and devices described here may be used to retrieve an anchor that has been incorrectly deployed (e.g., an anchor that has been deployed into a non-target site). For example, in certain variations, an anchor deployment catheter may be capable of retrieving an anchor. As an example, an anchor retrieval method may comprise compressing an anchor or anchors down to a collapsed configuration, and drawing the anchor or anchors back into a lumen of the catheter shaft. Any number of suitable devices or component parts may be useful in the retrieval process. For example, as shown in FIG. 11A, in some variations an anchor retrieval process may comprise coupling an anchor to a looped string or suture (1102) and loading the anchor into the anchor deployment catheter (1100). In this variation, the looped string (1102) is pulled distally (1104) out of catheter (1100), threaded onto one leg of the anchor (shown in FIG. 11A by dashed lines), and then slid around the anchor until it reaches, or is positioned about, the eyelet. Once looped string (1102) has been properly threaded, the anchor may be loaded into the anchor deployment catheter by pulling proximally (1106) on looped string (1102). Here, proximal pulling on the looped string can cause the anchor's legs to collapse against the anchor deployment catheter (1100), thereby allowing the anchor to be pulled therein. The looped string may also function to help with proper alignment and/or loading of the anchor into the anchor deployment catheter.

Figure 11B:
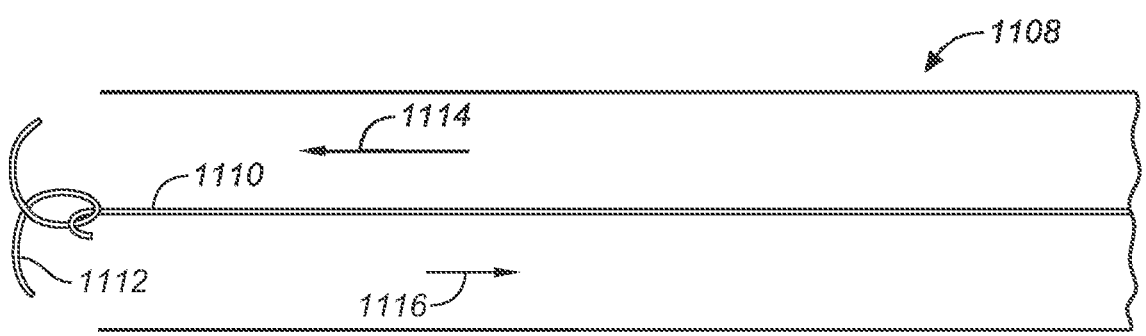

In another variation, shown in FIG. 11B, an anchor deployment catheter (1108) comprises a pull-push wire (1110). In a manner similar to that described with respect to FIG. 11A above, an anchor (1112) is first loaded or threaded onto push-pull wire (1110). This may be accomplished, for example, by pushing push-pull wire (1110) distally (1114) out of catheter (1108), and then loading anchor (1112) onto push-pull wire (1110) such that the distal hook of the push-pull wire (1110) is threaded through the eyelet of anchor (1112). The anchor may then be loaded into catheter (1108) by proximal pulling (1116) of push-pull wire (1110). As with the variation described above, the push-pull wire may also function to help with proper alignment and/or loading of the anchor into the anchor deployment catheter.

As described above, in certain variations, a procedure may be performed to deploy coupled anchors (e.g., tethered anchors) to a mitral valve region. FIGS. 12A-12D illustrate provide additional detail on a variation of such an anchor deployment method.

Figure 12A:
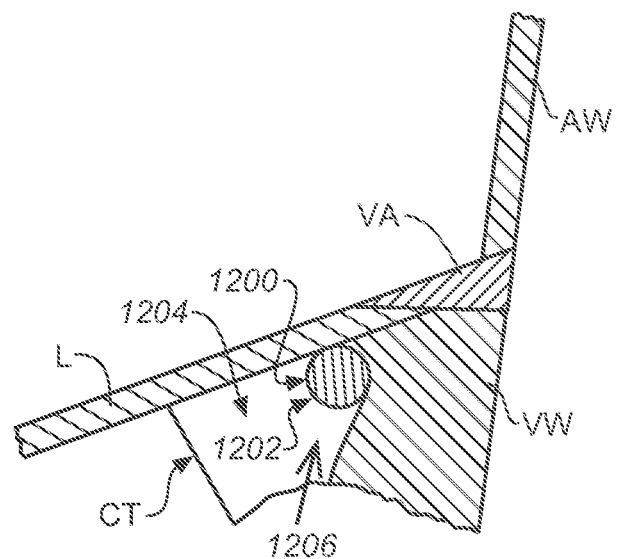
FIGS. 12A-12D are cross-sectional views of a portion of a heart, schematically illustrating the positioning and deployment of a variation of a tissue anchor into a region of a mitral valve annulus.

As shown in FIG. 12A, in one variation, a distal portion (1202) of an anchor deployment catheter (1200) may be positioned in a desired location under a valve leaflet (L) and adjacent a ventricular wall (VW). The valve annulus (VA) generally comprises an area of heart wall tissue at the junction of the ventricular wall (VW) and the atrial wall (AW) that is relatively fibrous and, thus, significantly stronger than leaflet tissue and other heart wall tissue. It is noted, however, that considerable structural variations of the annulus exist within patient populations and that attempted delivery of an implant to the valve annulus (VA) may instead result in the implant contacting or attaching to the tissue adjacent to the valve annulus. The term "annular tissue" as used herein shall include the valve annulus and the tissue adjacent to or surrounding the valve annulus.

Distal portion (1202) of anchor deployment catheter (1200) may be advanced into position generally under valve annulus (VA) by any suitable technique, such as one of the techniques described herein. Distal portion (1202) of anchor deployment catheter (1200) may be used to deploy anchors to the valve annular tissue, to stabilize and/or expose the annulus, or both. In one variation, using anchor deployment catheter (1200) having a flexible elongate body, flexible distal portion (1202) may be positioned in the left ventricle (LV) at the level of the mitral valve leaflets using any of a variety of access routes described herein. Distal portion (1202) may be advanced under the posterior valve leaflet into a space such as the subannular groove region (1204) or in the subvalvular space (1206) (FIG. 12A). It has been found that when anchor deployment catheter (1200) is passed, for example, under the mitral valve via an intravascular approach, anchor deployment catheter (1200) may be inserted into the subannular groove region (1204) or the subvalvular space (1206) and advanced either partially or completely around the circumference of the valve. Once in subannular groove region (1204) or the subvalvular space (1206), distal portion (1202) of anchor deployment catheter (1200) may be positioned proximate to the intersection of the valve leaflet(s) and ventricular wall (VW), which is near valve annulus (VA). These are but examples of possible access routes of a catheter to a valve annulus, and any other appropriate access routes may be used.

In some variations, it may be advantageous to provide anchor deployment catheter (1200) with a curvable portion having a radius in an expanded/curved state that is greater than a radius of the valve annulus, the subannular groove region or the ventricular chamber. The relative size of this portion of anchor deployment catheter (1200), when positioned within the smaller sized ventricle, may exert a radially outward force that can improve the surface contact between anchor deployment catheter (1200) and left ventricle (LV). For example, in one variation, anchor deployment catheter (1200) in the expanded state may have a radius about 10% to about 50% larger than that of the valve annulus. Additionally, certain variations of anchor deployment catheters may further include one or more expandable members (e.g., balloons) that may expand to urge or press or wedge the anchor deployment catheter into a target site (e.g., in the subvalvular space).

Figure 12B:
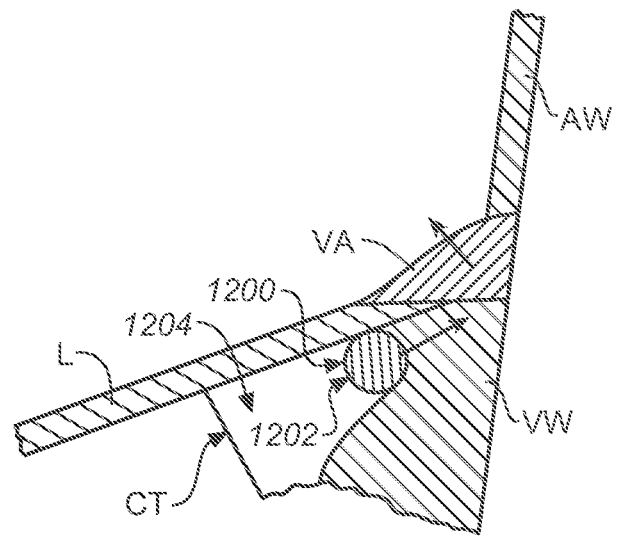
Figure 12C:
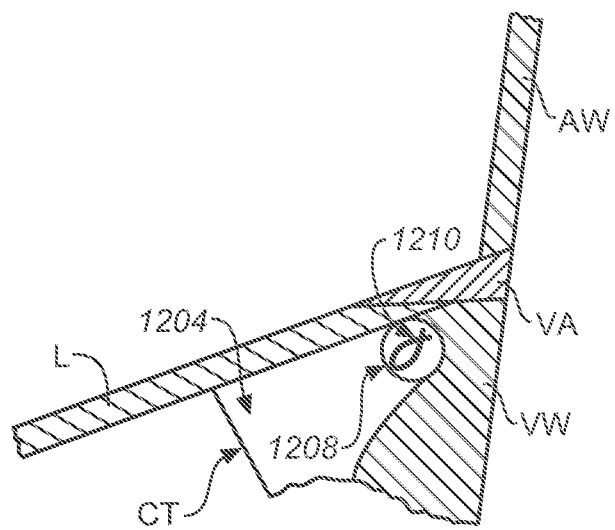

In addition to deploying anchors to the annular tissue, anchor deployment catheter (1200) (and specifically distal portion (1202)) may be used to stabilize and/or expose the valve annulus or annular tissue. Such stabilization and exposure are described, for example, in U.S. patent application Ser. No. 10/656,797 (published as US 2005/0055087 A1), which is hereby incorporated by reference in its entirety. For example, once distal portion (1202) is positioned generally under the annular tissue, force may be applied to distal portion (1202) to stabilize valve annulus (VA) or annular tissue, as shown in FIG. 12B. Such force may be directed in any suitable direction to expose, position and/or stabilize the annulus or annular tissue. In another example, an upward and lateral force is shown in FIG. 12B by the solid-headed arrow drawn from the center of distal portion (1202). In other examples, only upward, only lateral, or any other suitable force(s) may be applied. With application of force to distal portion (1202), the annular tissue may rise or project outwardly, such that the annulus is exposed for easier viewing and/or access. The applied force may also facilitate surgical procedures and visualization by stabilizing valve annulus (VA) or valve annular tissue.

Figure 12D:
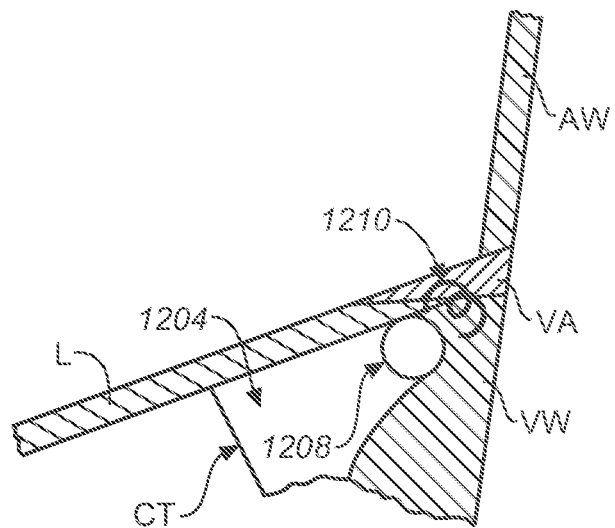

In some variations, additional force may be exerted by an anchor deployment device after the first anchor is engaged to body tissue. The first anchor may provide additional leverage and stability for manipulating the anchor deployment device. For example, referring to FIGS. 12C and 12D, an anchor deployment device (1208) is schematically shown deploying an anchor (1210) to a valve annulus (VA) or annular tissue. Anchor (1210) is shown first housed within anchor deployment device (1208) in FIG. 12C, and then deployed to annulus (VA) or annular tissue, as depicted in FIG. 12D. Of course, although the deployment and positioning of anchor (1210) is described with respect to valve annulus (VA), one or more anchors (1210) may miss valve annulus (VA) and attach to other structures or tissues accessible from subannular groove region (1204) (or subvalvular space (1206)).

As shown, in some variations, anchors (1210) may have a relatively straight configuration when housed in anchor deployment device (1208), with two penetrating tips and a loop in between the tips. Upon deployment from anchor deployment device (1208), the tips of an anchor (1210) may curve in opposite directions to form two semi-circles, circles, ovals, overlapping helices or the like. This is but one example of a type of self-securing anchor which may be deployed to annular tissue. Additional anchor variations are described, for example, in U.S. patent application Ser. No. 11/202,474 (published as US 2005/0273138 A1), which was previously incorporated by reference in its entirety. Multiple coupled anchors (1210) may be deployed, and the anchors (1210) may be drawn together to tighten the valve annulus.

Although the subannular groove region or subvalvular space of heart may be reached using a retrograde route through the aorta to the heart, other access routes may also be used. For example, access to the heart may also be transthoracic, with a delivery device being introduced into the heart via an incision or port in the heart wall. Even open heart surgical procedures may benefit from the methods and devices described herein. In some variations, hybrid access involving a combination of access methods described herein may be used. In one specific example, dual access to a valve may be achieved with a combination of venous and arterial access sites. User manipulation of both ends of a guidewire placed across a valve may improve positioning and control of the catheter and the implants. In other examples of hybrid access, both minimally invasive and surgical access may be used to implant one or more cardiac devices.

Other variations of methods may also include treatment of the tricuspid valve annulus, tissue adjacent the tricuspid valve leaflets, or any other cardiac or vascular valve. Thus, although the description herein discloses specific examples of devices and methods for mitral valve repair, the devices and methods may be used in any suitable procedure, both cardiac and non-cardiac. For example, in certain variations, the mitral valve reshaping devices and procedures may also be used with the tricuspid valve, and some variations may be adapted for use with the pulmonary and/or aortic valves. Likewise, the devices and methods truly be used in the left ventricle, the right ventricle, or either atrium, with any appropriate adaptations for a particular location being within the ability of a person of ordinary skill in the art. The devices and methods may also be used with the eat vessels of the cardiovascular system, for example, to treat aortic root dilatation.

Figure 13:
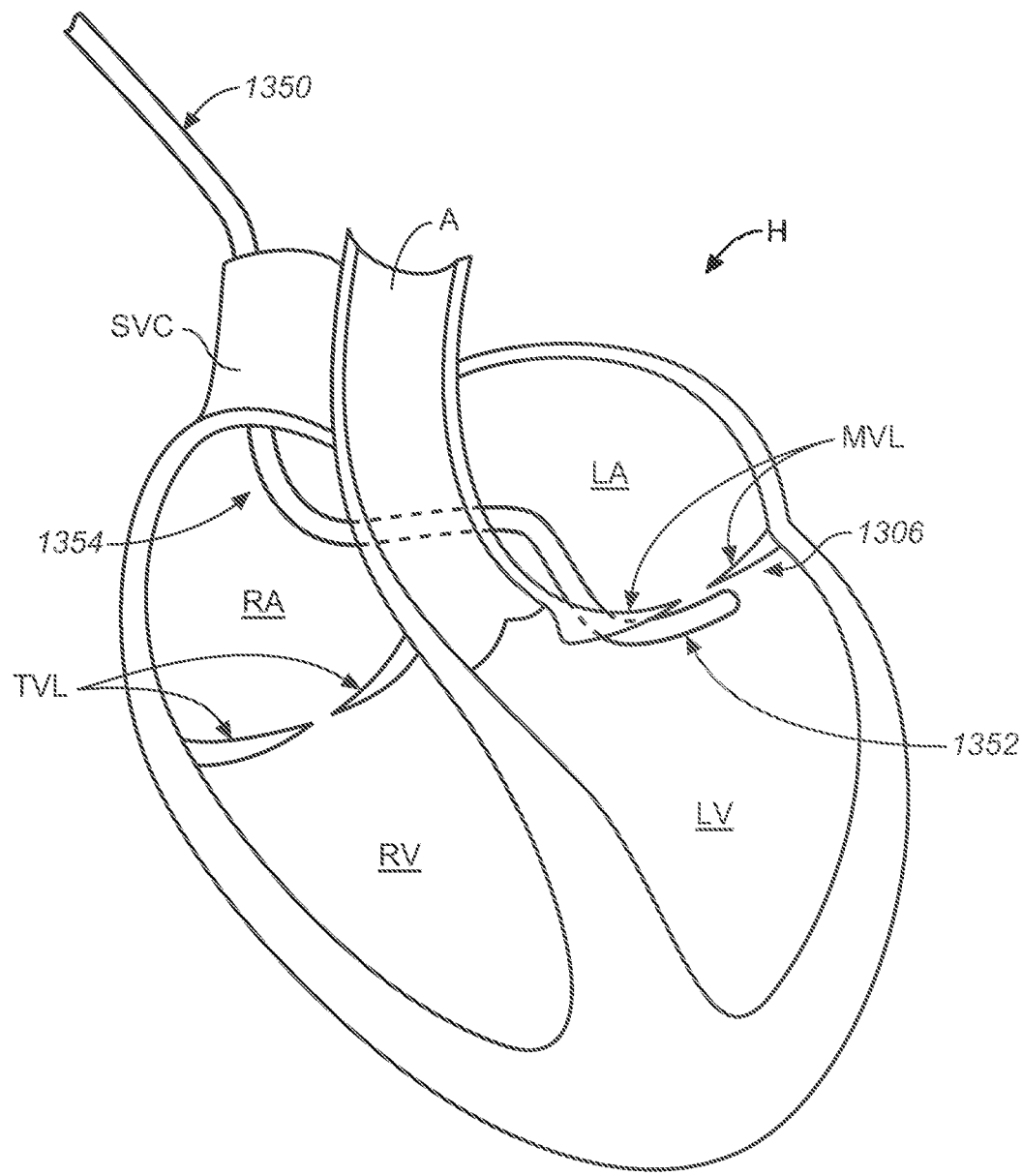
FIG. 13 shows a transseptal approach to the left ventricle of a heart

Access to the other chambers of the heart may be performed through percutaneous or venous cut-down access, including but not limited to transjugular, subclavicular, and femoral vein access routes. When venous access is established, access to the right atrium, the right ventricle, the tricuspid valve and other right-sided cardiac structures can occur. Furthermore, access to left-sided heart structures, such as the left atrium, left ventricle, mitral valve and the aortic valve, may be subsequently achieved by performing a transseptal puncture procedure. Referring to FIG. 13 with a heart (H) shown in cross-section, transseptal puncture is traditionally performed using a Mullins introducer sheath with a Brockenbrough curved needle through the interatrial septum to access the left atrium (LA), but any of a variety of other transseptal puncture devices or kits may also be used. After puncturing through left atrium (LA), supravalvular access to the mitral valve may be achieved by a guide catheter (1350) having a tubular body (1354), with the distal portion (1352) of the guide catheter entering the subvalvular space (1306). Antegrade access to the left ventricle (LV) can also occur by crossing the mitral valve. Similarly, access from the right ventricle (RV) to left ventricle (LV) may be obtained by transseptal puncture of the ventricular septum. In still other variations, a catheter device may access the coronary sinus and a valve procedure may be performed directly from the sinus.

Figure 14:
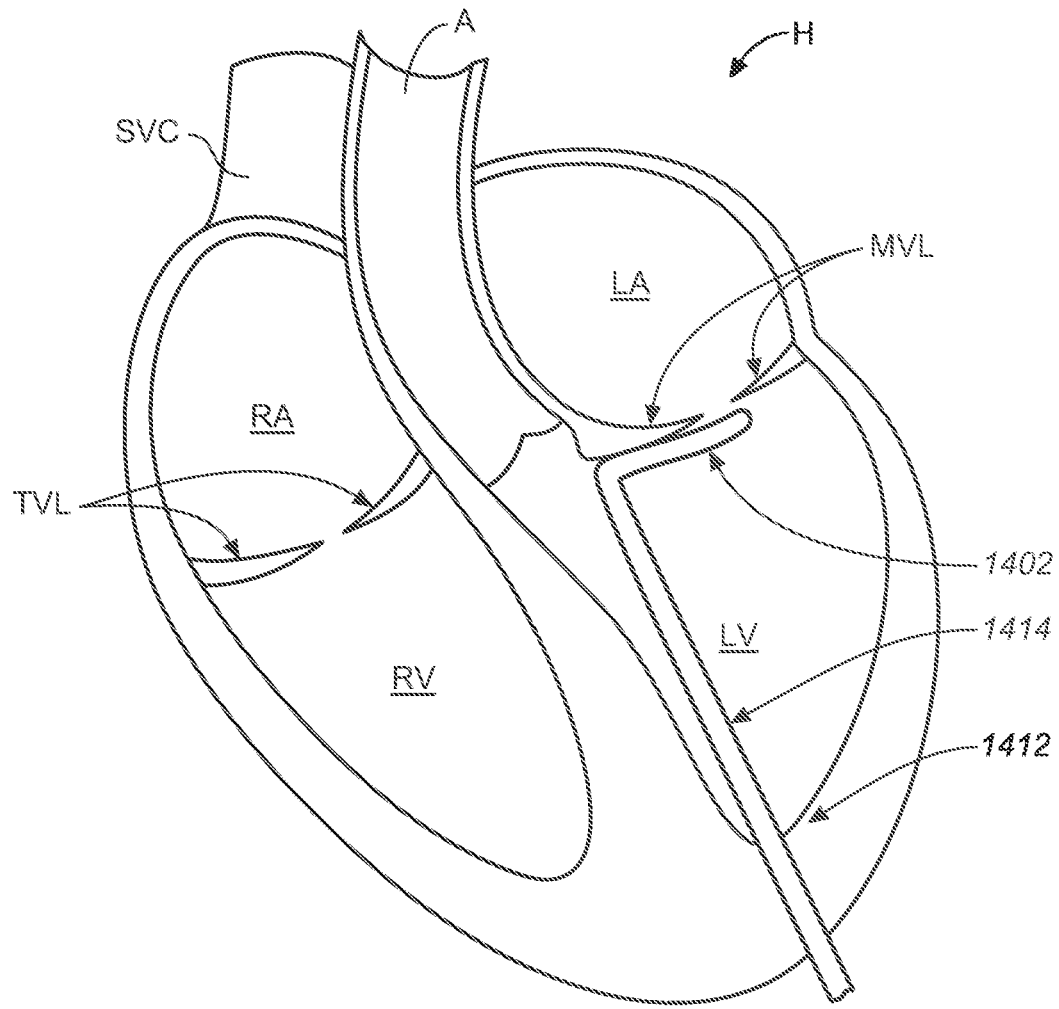
FIG. 14 shows a transapical approach to the left ventricle of a heart.

Surgical approaches that may be used include, but are not limited to, transcatheter procedures made through surgical incisions in the aorta or myocardium. In one particular variation, depicted in FIG. 14, a transapical approach with a surgical delivery device (1414) is utilized, to provide a guide catheter (1402) with a more linear route to the subvalvular space. The transapical approach also reduces potential effects of a myocardial incision on cardiac output, as the apical wall (1412) typically contributes less mechanical effect on left ventricular ejection fraction compared to other sections of the myocardial wall.

While heart valve repair has been described, in certain variations, the devices, methods, and/or kits described here may be used in a heart reshaping procedure, such as a ventricular remodeling procedure that is used to repair a heart experiencing valve dysfunction. Heart repair procedures, including heart reshaping procedures, are described, for example, in U.S. patent application Ser. No. 12/253,792 (published as US 2009/0234318 A1), which is hereby incorporated by reference in its entirety. Moreover, as discussed above, the devices, methods, and/or kits described herein may be used, as appropriate, in any of a number of different sites within the body and/or to assist with any of a number of different types of procedures. As an example, the devices, methods, and/or kits described herein may be used in NOTES procedures. As another example, the devices, methods, and/or kits described herein may be used in heart procedures other than those involving mitral valve repair. For example, they may be used to repair an aortic valve or a tricuspid valve, or to secure a prosthetic heart valve, or they may be used in heart ports. As an additional example, the devices, methods, and kits may be employed in a procedure in which one or more tethers are used to reinforce an annuloplasty ring.

Kits are also described here. In some variations, the kits may include at least one anchor deployment catheter. In certain variations, the kits may further include at least one guide catheter and/or at least one guide tunnel. In some variations, a kit may include multiple (e.g., 2, 3, 4, 5) different anchor deployment catheters. For example, a kit may include at least one primary anchor deployment catheter and at least one secondary anchor deployment catheter, or may include multiple secondary anchor deployment catheters. Additional examples of anchor deployment devices (and related methods) are disclosed, for example, in U.S. patent application Ser. No. 11/201,949 (published as US 2007/0055206 A1) and Ser. No. 11/583,627 (published as US 2008/0172035 A1), both of which are hereby incorporated by reference in their entirety. Anchor deployment devices and related methods are also disclosed in U.S. Provisional Application Ser. Nos. 61/160,230, filed on Mar. 13, 2009, and 61/178,910, filed on May 15, 2009, both of which were previously incorporated by reference in their entirety. In certain variations, a kit may include one or more cinching devices and/or one or more termination devices (e.g., locking devices, cutting devices, or combination locking and cutting devices). Cinching devices are described, for example, in U.S. Provisional Application Ser. No. 61/104,686, filed on Oct. 10, 2008, and U.S. patent application Ser. No. 12/576,955, filed on Oct. 9, 2009, both of which are hereby incorporated by reference in their entirety. Termination devices are described, for example, in U.S. patent application Ser. No. 11/232,190 (published as US 2006/0190030 A1); Ser. No. 11/270,034 (published as US 2006/0122633 A1); and Ser. No. 12/577,044 (filed on Oct. 9, 2009), each of which is hereby incorporated by reference in its entirety. Termination devices are also described in U.S. Provisional Application Ser. No. 61/104,681, filed on Oct. 10, 2008, which is hereby incorporated by reference in its entirety. Of course, instructions for use may also be provided with the kits. Moreover, the components of the kit may be packaged together or separately.

While the devices, methods, and kits have been described in some detail here by way of illustration and example, such illustration and example is for purposes of clarity of understanding only. It will be readily apparent to those of ordinary skill in the art in light of the teachings herein that certain changes and modifications may be made thereto without departing from the spirit and scope of the appended claims.

What is claimed is:

1. An anchor delivery catheter comprising:
   a tubular elongated member having a proximal end, a distal end, a side portion therebetween and a lumen therethrough;
   an elongated wire extending from the side portion, wherein a bend in the elongated wire signals to an operator when to stop advancing the tubular elongate member;
   an anchor located within the lumen;
   a first anchor-retaining notch located within the lumen of the tubular elongated member; and
   a second anchor-retaining notch, wherein retaining the anchor within the first and second notches orients the anchor for deployment.

2. The catheter of claim 1, wherein the anchor-retaining notches are configured to temporarily retain the anchor.

3. The catheter of claim 1, further comprising an internal stop element and the first anchor-retaining notch is located on the internal stop element.

4. The catheter of claim 3, wherein the internal stop element is radiopaque.

5. The catheter of claim 3, wherein the internal stop element comprises a tubular member having a sidewall, and the first anchor-retaining notch is extends along a length of the sidewall.

6. The catheter of claim 5, further comprising a pushing member that is configured to be advanced into a lumen of the tubular member.

7. The catheter of claim 3, wherein the internal stop element is separate from the elongated wire.

8. The catheter of claim 1, further comprising a coupling member coupled to the anchor.

9. The catheter of claim 8, wherein the coupling member is a tether.

10. The catheter of claim 1, wherein the tubular elongated member comprises a preformed shape having a first region defining a first plane and a second region defining a second plane at an angle with respect to the first plane.

11. The catheter of claim 10, wherein the angle is from about 10 degrees to about 90 degrees.

12. The catheter of claim 1, wherein the bend in the elongated wire is a backward bend.

13. The catheter of claim 1, wherein the second anchor-retaining notch is located within the lumen of the tubular elongated member.

* * * * *